United States Patent
Dunn et al.

(10) Patent No.: US 7,625,949 B2
(45) Date of Patent: *Dec. 1, 2009

(54) METHODS FOR TREATING RETROVIRAL INFECTIONS

(75) Inventors: James Patrick Dunn, Los Altos, CA (US); Donald Roy Hirschfeld, Mountain View, CA (US); Tania Silva, Sunnyvale, CA (US); Zachary Kevin Sweeney, Redwood City, CA (US); Harit Vora, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 796 days.

This patent is subject to a terminal disclaimer.

(21) Appl. No.: 11/112,590

(22) Filed: Apr. 22, 2005

(65) Prior Publication Data

US 2005/0239880 A1 Oct. 27, 2005

Related U.S. Application Data

(60) Provisional application No. 60/565,116, filed on Apr. 23, 2004.

(51) Int. Cl.
| | |
|---|---|
| A61K 31/18 | (2006.01) |
| A61K 31/165 | (2006.01) |
| A61K 31/33 | (2006.01) |
| A61K 31/497 | (2006.01) |
| A61K 31/435 | (2006.01) |
| A61K 31/44 | (2006.01) |
| A61K 31/40 | (2006.01) |
| A61K 31/405 | (2006.01) |

(52) U.S. Cl. .................. 514/601; 514/602; 514/603; 514/617; 514/183; 514/252.1; 514/277; 514/334; 514/344; 514/345; 514/415; 514/422; 514/423; 514/424; 514/425; 514/426; 514/427

(58) Field of Classification Search .................. 514/601, 514/602, 603, 617, 183, 252.1, 277, 334, 514/344, 345, 415, 422–427
See application file for complete search history.

(56) References Cited

U.S. PATENT DOCUMENTS

| 6,028,080 | A | 2/2000 | Ackermann et al. |
|---|---|---|---|
| 6,710,205 | B2 | 3/2004 | Tani et al. |
| 2003/0114435 | A1 | 6/2003 | Tani et al. |
| 2003/0187068 | A1 | 10/2003 | Miyachi et al. |
| 2003/0220241 | A1 | 11/2003 | Defeo-Jones et al. |

FOREIGN PATENT DOCUMENTS

| JP | 2-218654 | 8/1990 |
|---|---|---|
| WO | WO 92/00952 | 1/1992 |
| WO | WO 93/15043 | 8/1993 |
| WO | WO 96/22990 | 8/1996 |
| WO | WO 97/26244 | 7/1997 |
| WO | WO 98/50346 | 11/1998 |
| WO | WO 99/17777 A1 | 4/1999 |
| WO | WO 99/55663 | 11/1999 |
| WO | WO 99/65874 | 12/1999 |
| WO | WO 00/64876 | 11/2000 |
| WO | WO 01/17982 | 3/2001 |
| WO | WO 01/19788 A2 | 3/2001 |
| WO | WO 01/21596 | 3/2001 |
| WO | WO 01/64642 A2 | 9/2001 |
| WO | WO 02/057236 A1 | 7/2002 |
| WO | WO 02/070494 A1 | 9/2002 |

OTHER PUBLICATIONS

Milton et al. Biaryl acids: Novel non-nucleoside inhibitors of HIV reverse transcriptase types 1 and 2, Bioorganic & Medicinal Chemistry Letters, 1998, vol. 8, pp. 2623,2628.*
W. Buckheit, Jr., Non-nucleoside reverse transcriptase inhibitors: perspectives for novel therapeutic compounds and strategies for treatment of HIV infection, *Expert Opin. Investig.* Drugs 2001 10(8):1423-1442.
R. W. Carling et al., 4-Substituted-3-phenylquinolin-2(1H)-ones: Acidic and Nonacidic Glycine Site N-Methyl-D-aspartate Antagonists with in Vivo Activity, *J. Med. Chem.*, 1997 40:754-765.
J. H. Chan et al., Novel Benzophenones as Non-nucleoside Reverse Transcriptase Inhibitors of HIV-1. *J. Med Chem.* 2004 47(5):1175-1182.
E. De Clercq, New Developments in Anti-HIV Chemotherap. *Curr. Med. Chem.* 2001 8:1543-1572.
M. C. Iles et al., Carbonic Anhydrase Inhibitors. Inhibition of Tumor-Associated Isozyme IX by Halogenosulfanilamide and Halogenophenylaminobenzolamide Derivatives, *J. Med. Chem.* 2003 46(11):2187-2196.
A. Kreimeyer et al., Evaluation and Biological Properties of Reactive Ligands for the Mapping of the Glycine Site on the N-Methyl-D-aspartate (NMDA) Receptor, *J. Med. Chem.* 1999 42:4394-4404.
J. J. Kulagowski et al., 3'-(Arylmethyl)- and 3'-(Aryloxy)-3-phenyl-4-hydroxyquinolin-2(1H)-ones: Orally Active Antagonists of the Glycine Site on the NMDA Receptor, *J. Med. Chem.* 1994 37:1402-1405.

(Continued)

*Primary Examiner*—Shengjun Wang
(74) *Attorney, Agent, or Firm*—Brian L. Buckwalter

(57) ABSTRACT

The present invention provides compounds for treating or preventing an HIV infection, or treating AIDS or ARC comprising administering a compound according to formula I where Ar, $R^1$-$R^5$, $R^{11c}$ and $X^1$ are as defined herein.

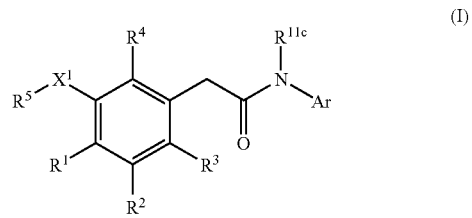

(I)

13 Claims, No Drawings

OTHER PUBLICATIONS

M. Rowley et al., Effect of Plasma Protein Binding on in Vivo Activity and Brain Penetration of Glycine/NMDA Receptor Antagonists, *J. Med. Chem.* 1997 40:4053-4068.

P. G. Wyatt et al., Benzophenone Derivatives: A Novel Series of Potent and Selective Inhibitors of Human Immunodeficiency Virus Type 1 Reverse Transcriptase, *J. Med. Chem.* 1995 38(10):1657-1665).

* cited by examiner

METHODS FOR TREATING RETROVIRAL INFECTIONS

CROSS REFERENCE TO RELATED APPLICATIONS

This application claims the benefit of priority to U.S. Ser. No. 60/565,116 filed Apr. 23, 2004 and which is hereby incorporated by reference in its entirety.

FIELD OF THE INVENTION

The invention relates to the field of antiviral therapy and, in particular, to non-nucleoside compounds that inhibit HIV reverse transcriptase and are useful for treating Human Immunodeficiency Virus (HIV) mediated diseases. The invention provides novel N-phenyl phenylacetamide compounds according to formula I, for treatment or prophylaxis of HIV mediated diseases, ADS or ARC, employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the $CD4^+$ T-cell, with attendant susceptibility to opportunistic infections. HIV infection is also associated with a precursor AIDs-related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase. (J. S. G. Montaner et al. *Antiretroviral therapy: 'the state of the art'* Biomed & Pharmacother. 1999 53:63-72; R. W. Shafer and D. A. Vuitton, *Highly active retroviral therapy (HAART) for the treatment of infection with human immunodeficiency virus type*, Biomed. & Pharmacother. 1999 53 :73-86; E. De Clercq, *New Developments in Anti-HIV Chemotherap. Curr. Med. Chem.* 2001 8:1543-1572). Two general classes of RTI inhibitors have been identified: nucleoside reverse transcriptase inhibitors (NRTI) and non-nucleoside reverse transcriptase inhibitors.

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV reverse transcriptase thereby altering the shape of the active site or blocking polymerase activity (R. W. Buckheit, Jr., *Non-nucleoside reverse transcriptase inhibitors: perspectives for novel therapeutic compounds and strategies for treatment of HIV infection*, Expert Opin. Investig. Drugs 2001 10(8):1423-1442; E. De Clercq *The role of non-nucleoside reverse transcriptase inhibitors (NNRTIs) in the therapy of HIV infection*, Antiviral Res. 1998 38:153-179; E. De Clercq *New Developments in Anti-HIV Chemotherapy*, Current medicinal Chem. 2001 8(13):1543-1572; G. Moyle, *The Emerging Roles of Non-Nucleoside Reverse Transcriptase Inhibitors in Antiviral Therapy*, Drugs 2001 61 (1): 19-26). Although over thirty structural classes of NNRTIs have been identified in the laboratory, only three compounds have been approved for HIV therapy: efavirenz, nevirapine and delavirdine.

Initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT. While combination therapy with NRTIs, PIs and NNRTIs has, in many cases, dramatically lowered viral loads and slowed disease progression, significant therapeutic problems remain. (R. M. Gulick, *Eur. Soc. Clin. Microbiol. and Inf. Dis.* 2003 9(3):186-193) The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV.

Certain N-phenyl phenylacetamide compounds have been found to have a variety of pharmacological properties.

US 20030187068 (H. Miyachi et al.) discloses N-phenyl phenylacetamide compounds which are peroxisome proliferators-activated receptor (PPARα) ligands.

US 20030220241 (D. Defoe-Jones et al.) disclose N-phenyl phenylacetamide compounds use to prepare protein conjugates with a prenyl protein transferase which are cleaved by prostate-specific antigen and are useful for treating cancer. WO9917777 (J. S. Desolms et al.) teach prenyl protein transferase compounds which include N-phenyl phenylacetamides.

N-(substituted)phenyl 3-phenoxy-phenylacetamide compounds have been disclosed in WO01/21596 (A. A. Mortlock et al.) as inhibitors of aurora 2 kinase which are potentially useful in the treatment of proliferative diseases.

N-phenyl 3-(substituted)phenoxy-phenylacetamide compounds have be disclosed in WO2000059930 as inhibitors of prenyl protein transferase.

N-(substituted)phenyl 3-phenoxy-phenylacetamide compounds have been disclosed in US 2003011435 (K. Tani et al.) as EP4 receptor antagonists which are potentially useful in the suppression of TNF-α production and induction of IL-10 production.

Benzanilide compounds have been disclosed in WO9965874 (Y. Ohtake et al.) as vasopressin antagonists.

N-phenyl phenylacetamide compounds 1 wherein $R^1$ can be substituted aryl, $X^1$ can be O, n can be 0, $R^4$ and $R^5$ can be hydrogen have been disclosed in WO9315043 (T. Oe et al.) as acetyl CoA cholesterol O-acyltransferase inhibitors useful for reducing blood lipid levels and for treating arteriosclerosis.

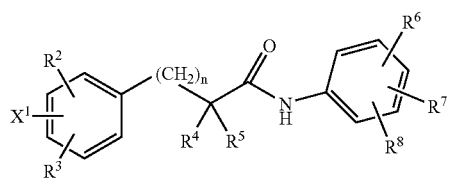

N-Phenyl phenylacetamides have also been used as synthetic intermediates for the preparation of pharmacologically active compounds. N-(2-carboalkoxy-5-chloro-phenyl) phenylacetamides (A. Kreimeyer et al., *J. Med. Chem.* 1999 42:43944404; J. J. Kulagowski et al., *J. Med. Chem.* 1994 37:1402-1405 K. Ackermann et al., WO 97/26244), N-(2-cyano-5-chloro-phenyl) phenylacetamides (M. Rowley et al., *J. Med. Chem.* 1997 40:4053-4068; R. W. Carling et al., *J. Med. Chem.*, 1997 40:754-765 and N-(2-nitrophenyl) phenylacetamides (J. F. W. Keana et al., WO 96/22990) have been disclosed and utilized as intermediates for the synthesis of ligands for the glycine site on the N-methyl-D-aspartate (NMDA) receptor. NMDA ligands have been investigated for treating CNS disorders thought to be related neuronal death caused by over-stimulation of the post synaptic receptor sensitive to N-methyl-D-aspartic acid. Such disorders include Alzheimer's disease, epilepsy and cerebral ischemia. These compounds and indications are unrelated to the present invention.

2-Benzoyl phenyl-N-[phenyl]-acetamide compounds 2a and 2b have been shown to inhibit HIV-1 reverse transcriptase (P. G. Wyatt et al., *J. Med. Chem.* 1995 38(10):1657-1665). Further screening identified related compounds, e.g. 2-benzoyl phenyloxy-N-[phenyl]-acetamide, 3a, and a sulfonamide derivative 3b which also inhibited reverse transcriptase (J. H. Chan et al., *J. Med Chem.* 2004 47(5): 1175-1182; C. L. Webster et al., WO01/17982).

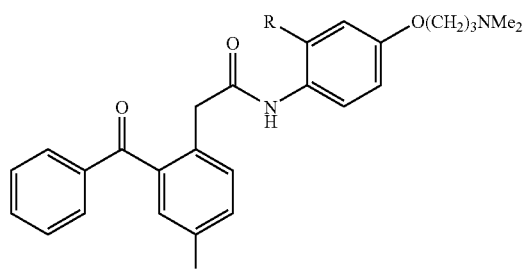

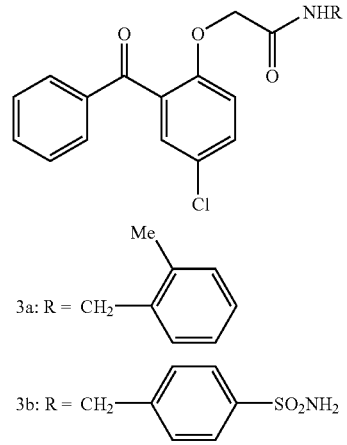

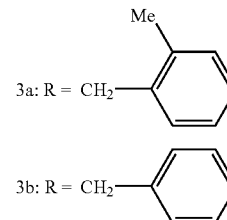

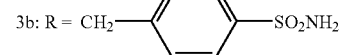

SUMMARY OF THE INVENTION

The present invention related to methods for treating an HIV infection and the treatment of AIDS and/or ARC using compounds according to formula I. HIV undergoes facile mutations of its genetic code resulting in strains with reduced susceptibility to therapy with current therapeutic options. The invention also relates to methods of treating HIV infections resistant to, or with reduced susceptibility to, currently available non-nucleoside reverse transcriptase inhibitors. The present invention further relates to compounds of formula I which are useful in mono therapy or combination therapy with other anti-viral agents. The present invention further relates to new pharmaceutical compositions for treating HIV containing compounds according to formula I:

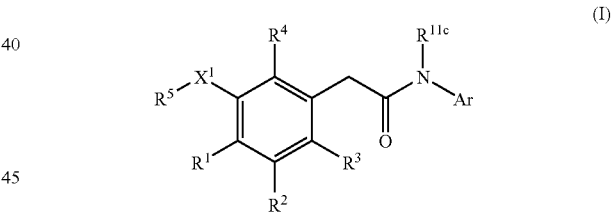

wherein
$X^1$ is selected from the group consisting of —O—, —S—, —CH$_2$—, —C(O)—;
$R^1$ and $R^2$ are (i) each independently selected from the group consisting of hydrogen, $C_{1-6}$alkyl, $C_{1-6}$haloalkyl, $C_{3-8}$cycloalkyl, $C_{1-6}$alkoxy, $C_{1-6}$alkylthio, $C_{1-6}$alkylsulfinyl, $C_{1-6}$sulfonyl, $C_{1-6}$haloalkoxy, $C_{1-6}$haloalkylthio, halogen, amino, alkylamino, dialkylamino, acylamino, nitro and cyano; or, (ii) together $R^1$ and $R^2$ are —O—CH=CH— or —O—CH$_2$CH$_2$—
$R^3$ and $R^4$ are independently selected from the group consisting of hydrogen, $C_{1-6}$ alkyl, $C_{1-6}$ haloalkyl, $C_{1-6}$ alkoxy, $C_{1-6}$ haloalkoxy $C_{1-6}$ alkylthio, $C_{1-6}$ haloalkylthio, halogen, amino, nitro and cyano;
$R^5$ is selected from the group consisting of $C_{1-6}$ alkyl, $C_{1-6}$ haloalkyl, $C_{3-8}$ cycloalkyl, aryl or heteroaryl selected from the group consisting of pyridinyl, N-hydroxypyridine, pyrimidinyl, indole, pyrazinyl and pyrrolyl; wherein, said aryl and said heteroaryl are optionally substituted with one to three substituents independently selected from the group consisting of $C_{1-6}$ alkyl, $C_{2-6}$ alkenyl, $C_{2-6}$ alkynyl, —C≡CCH$_2$OH, —C≡CCH$_2$NMe$_2$, $C_{1-6}$ haloalkyl, $C_{3-8}$ cycloalkyl, $C_{1-6}$alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-6}$ alkylamino, $C_{1-6}$ dialkylamino, acylamino, acyl, $C_{1-6}$ alkoxycarbonyl, carbamoyl, $C_{1-6}$ N-alkylcarbamoyl, $C_{1-6}$ N,N-dialkylcarbamoyl, nitro and cyano, said alkyl and said cycloalkyl are optionally substituted with one or two substituents independently selected from the group consisting of alkyl, hydroxy, alkoxy, thiol, alkylthio, halogen, amino, alkylamino, dialkylamino, amino alkyl, alkylaminoalkyl, and dialkylamino;

Ar is (i) phenyl optionally substituted with 1 to 3 substituents independently selected each incidence is from the group consisting of $C_{1-6}$ alkyl, $C_{3-8}$ cycloalkyl, $C_{1-3}$ haloalkyl, $C_{1-6}$ alkoxy, $C_{1-6}$ haloalkoxy, halogen, cyano, $C_{1-6}$ alkylthio, $C_{1-6}$ alkylsulfinyl, $C_{1-6}$ sulfonyl, amino $C_{1-6}$ alkylsulfonyl, $C_{1-6}$ haloalkoxy, $C_{1-6}$ haloalkylthio, $C_{1-6}$ acyl, nitro, $C_{1-6}$ heteroalkyl, $C_{1-6}$ heteroalkoxy, hydroxyl, —X$^2$(CH$_2$)$_p$S(O)$_n$NR$^8$R$^9$; —(CH$_2$)$_p$COOR$^{11}$, —X$^2$(CH$_2$)$_p$ NHC(O)NHR$^8$R$^9$, X$^2$(CH$_2$)$_p$CONR$^8$R$^9$,—SO$_2$R$^{13}$, —NR$^{8a}$R$^{9a}$, X$^2$(CH$_2$)$_p$NR$^{11}$S(O)$_2$NR$^8$R$^9$, —X$^2$(CH$_2$)$_p$NHCOOR$^{10}$, —X$^6$(CH$_2$)$_p$COOR$^{10}$, —X$^2$(CH$_2$)$_p$CN, —OR$^{15}$ and C(=O)CH$_2$N[(CH$_2$)$_2$]$_2$X$^4$; or, (ii) a heteroaryl ring selected from the group consisting of pyridinyl, pyrazolyl and triazolyl said heteroaryl ring optionally substituted with one to three substituents selected from the group consisting of $C_{1-6}$ alkyl, $C_{1-6}$ alkoxy, $C_{1-6}$ alkylthio, halogen, $C_{1-6}$ aminoacyl and NR$^{8b}$R$^{9b}$;

R$^8$ and R$^9$ (i) taken independently, one of R$^8$ and R$^9$ is hydrogen or $C_{1-6}$ alkyl and the other of R$^8$ and R$^9$ is selected from the group consisting of hydrogen, —C(=O)R$^{14}$, —C(=O)CHR$^{12}$NH$_2$, —(CH$_2$)$_2$N[(CH$_2$)$_2$]$_2$O, COCO$_2$Me, $C_{3-8}$ cycloalkyl said cycloalkyl optionally substituted with one or two hydroxyl substituents, pyranyl, $C_{1-6}$ alkyl and aryl said alkyl and said aryl groups optionally substituted with one or two substituents independently selected from the group consisting of hydroxy, $C_{1-6}$ alkoxy, thiol, $C_{1-6}$ alkylthio, $C_{1-6}$ alkylsulfinyl, $C_{1-6}$ sulfonyl, and halogen; or, (ii) R$^8$ and R$^9$ taken together are (CH$_2$)$_2$—X$^5$—(CH$_2$)$_2$ or —(CH$_2$)$_o$— optionally substituted with one or two substituents selected from the group consisting of halogen, hydroxyl and NR$^{11a}$R$^{11b}$;

R$^{8a}$ and R$^{9a}$ (i) taken independently are selected from the group consisting of hydrogen, $C_{1-6}$ alkyl, C(=O) CO$_2$R$^{11}$ and SO$_2$R$^{10}$, or (ii) taken together are (CH$_2$)$_r$SO$_2$, (CH$_2$)$_2$S(O)$_p$(CH$_2$)$_2$;

R$^{10}$ is $C_{1-6}$ alkyl;

R$^{11}$ is hydrogen or $C_{1-6}$ alkyl;

R$^{11a}$, R$^{11b}$ and R$^{11c}$ are independently R$^{11}$;

R$^{12}$ is the side chain of a naturally occurring α-amino acid;

R$^{13}$ is $C_{1-6}$ alkyl; —(CH$_2$),CO$_2$R$^{11}$, —(CH$_2$)$_2$CN, —(CH$_2$)$_2$NH$_2$, —(CH$_2$)$_u$OH;

R$^{14}$ is $C_{1-6}$ alkyl, —(CH$_2$)$_s$NHR$^{11a}$R$^{11b}$, (CH$_2$)$_s$OR$^{11}$, —CH$_2$CH(OH)CH$_3$, CH$_2$N[(CH$_2$)$_2$]$_2$O, —(CH$_2$)$_2$CO$_2$R$^{11}$, optionally substituted phenyl or pyridinyl;

R$^{15}$ is $C_{1-6}$ alkyl optionally substituted with one to three hydroxyl groups;

X$^2$ is —O— or a bond;

X$^4$ is —O— or —NMe—;

X$^5$ is —O—, —S(O)$_n$—or NR$^{11}$;

X$^6$ is O— or —S(O)$_n$—;

n is an integer from 0 to 2;

o is an integer from 4 to 6;

p is an integer from 0 to 6;

r is an integer from 3 to 4 s is an integer from 1 to 2;

u is an integer from 2 to 3; and, hydrates, solvates and salts thereof

DETAILED DESCRIPTION OF THE INVENTION

In one embodiment of the present invention there is provided a method for treating an HIV infection, or preventing an HIV infection, or treating AIDS or ARC, comprising administering to a host in need thereof a therapeutically effective amount of a compound of formula I wherein R$^1$, R$^2$, R$^3$, R$^4$, R$^5$, R$^8$, R$^{8a}$, R$^9$, R$^{9a}$, R$^{10}$, R$^{11}$, R$^{11a, R11b}$, R$^{11c}$, R$^{12}$, R$^{13}$, R$^{14}$, R$^{15}$, Ar, X$^1$, X$^2$, X$^4$, X$^5$, X$^6$, n, o, p, r, s and u are as defined herein above; and, hydrates, solvates and salts thereof.

In one embodiment of the present invention there is provided a method for treating an HIV infection, or treating AIDS or ARC, comprising administering to a host in need thereof a therapeutically effective amount of a compound of formula I wherein R$^1$, R$^2$, R$^3$, R$^4$, R$^5$, R$^8$, R$^{8a}$, R$^9$, R$^{9a}$, R$^{10}$, R$^{11}$, R$^{11a}$, R$^{11b}$, R$^{11c}$, R$^{12}$, R$^{13}$, R$^{14}$, R$^{15}$, Ar, X$^1$, X$^2$, X$^4$, X$^5$, X$^6$, n, o, p, r, s and u are as defined herein above; and hydrates, solvates and salts thereof.

In another embodiment of the present invention there is provided a method for treating an HIV infection, or treating AIDS or ARC, comprising administering to a host in need thereof a therapeutically effective amount of a compound of formula I wherein X$^1$ is O and X$^2$ is a bond; R$^3$ is hydrogen or halogen; R$^4$ is hydrogen, halogen or $C_{1-6}$ alkyl; R$^5$ is optionally substituted aryl; R$^{11c}$ is hydrogen; p is 0; and, R$^1$, R$^2$, R$^8$, R$^{8a}$, R$^9$, R$^{9a}$, R$^{10}$, R$^{11}$, R$^{11a}$, R$^{11b}$, R$^{12}$, R$^{13}$, R$^{14}$, R$^{15}$, Ar X$^4$, X$^5$, X$^6$, n, o, r, s and u are as defined herein above; and hydrates, solvates and salts thereof.

In another embodiment of the present invention there is provided a method for treating an HIV infection, or treating AIDS or ARC, comprising administering to a host in need thereof a therapeutically effective amount of a compound of formula I wherein X$^1$ is O and X$^2$ is a bond; Ar is optionally substituted aryl; R$^1$ and R$^2$ are each independently hydrogen, $C_{1-6}$ alkyl, $C_{1-6}$ haloalkyl, $C_{3-8}$ cycloalkyl, $C_{1-6}$ alkoxy, $C_{1-6}$ haloalkoxy, $C_{1-6}$ haloalkylthio, halogen, nitro and cyano; R$^3$ is hydrogen or fluoro; R$^4$ is hydrogen, fluoro, chloro or $C_{1-6}$ alkyl; R$^5$ is optionally substituted aryl; R$^{11c}$ is hydrogen; p is 0; and, R$^8$, R$^{8a}$, R$^9$, R$^{9a}$, R$^{10}$, R$^{11}$, R$^{11a}$, R$^{11b}$, R$^{12}$, R$^{13}$, R$^{14}$, R$^{15}$, X$^4$, X$^5$,X$^6$, n, o, r, s and u are as defined herein above; and, hydrates, solvates and salts thereof.

In another embodiment of the present invention there is provided a method for treating an HIV infection, or treating AIDS or ARC, comprising administering to a host in need thereof a therapeutically effective amount of a compound of formula I wherein X$^1$ is O and X$^2$ is a bond; Ar is optionally substituted aryl; R$^1$ and R$^2$ are each independently hydrogen, $C_{1-6}$ alkyl, $C_{1-6}$ haloalkyl, $C_{3-8}$ cycloalkyl, $C_{1-6}$ alkoxy, $C_{1-6}$ haloalkoxy, $C_{1-6}$ haloalkylthio, halogen, nitro and cyano; R$^3$ is hydrogen or fluoro; R$^4$ is hydrogen, fluoro, chloro or $C_{1-6}$ alkyl; R$^5$ is 2,4-disubstituted phenyl, 2,5-disubstituted phenyl, 3,5-disubstituted phenyl or 2,3,5-trisubstituted phenyl; R$^{11c}$ is hydrogen; p is 0; and, R$^8$, R$^{8a}$, R$^9$, R$^{9a}$, R$^{10}$, R$^{11}$, R$^{11a}$, $R^{11b}$, $R^{12}$, $R^{13}$, $R^{14}$, $R^{15}$, $X^4$, $X^5$, $X^6$, n, o, r, s and u are as defined herein above; and, hydrates, solvates and salts thereof.

In another embodiment of the present invention there is provided a method for treating an HIV infection, or treating AIDS or ARC, comprising administering to a host in need thereof a therapeutically effective amount of a compound of formula I wherein $X^1$ is O and $X^2$ is a bond; Ar is optionally substituted aryl; $R^1$ is chloro, bromo, $C_{1-6}$ alkyl or $C_{1-6}$ alkoxy, $R^2$ is hydrogen, $C_{1-6}$ alkyl or bromo, $R^3$ is H, $R^4$ is hydrogen or fluoro; $R^5$ is 2,4-disubstituted phenyl, 2,5-disubstituted phenyl, 3,5-disubstituted phenyl or 2,3,5-trisubstituted phenyl optionally substituted in each incidence with a substituents selected from the group consisting of halogen, cyano, $C_{1-6}$ alkyl, $C_{1-6}$ haloalkyl; Ar is phenyl substituted according to formula II

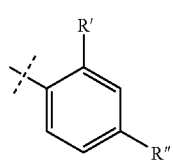

(II)

wherein $R^1$ is hydrogen $C_{1-6}$ alkyl, or chloro and $R^{11}$ is hydrogen, $X^2(CH_2)_pS(O)_nNR^8R^9$, $X^2$ is a bond; $R^{11c}$ is hydrogen; p is 0; n is 2; and, $R^8$, $R^9$, $R^{11}$, $R^{11a}$, $R^{11b}$, $R^{12}$, $R^{14}$, $X^5$, n, o, r, s and u are as defined herein above; and, hydrates, solvates and salts thereof.

In another embodiment of the present invention there is provided a method for treating an HIV infection, or treating AIDS or ARC, comprising administering to a host in need thereof a therapeutically effective amount of a compound of formula I wherein $X^1$ is O and $x^2$ is a bond; Ar is optionally substituted aryl; $R^1$ is chloro, bromo, $C_{1-6}$ alkyl or $C_{1-6}$ alkoxy, $R^2$ is hydrogen, $C_{1-6}$ alkyl or bromo, $R^3$ is H, $R^4$ is hydrogen or fluoro; $R^5$ is 2,4-disubstituted phenyl, 2,5-disubstituted phenyl, 3,5-disubstituted phenyl or 2,3,5-trisubstituted phenyl optionally substituted in each incidence with a substituents selected from the group consisting of halogen, cyano, $C_{1-6}$ alkyl, $C_{1-6}$ haloalkyl; $R^{11c}$ is hydrogen; Ar is phenyl substituted according to formula II; $R^1$ is hydrogen $C_{1-6}$ alkyl, or chloro and $R^{11}$ is hydrogen, $X^2(CH_2)_pS(O)_nNR^8R^9$, $R^8$ is hydrogen, $R^9$ is hydrogen, $C(=O)R^{14}$ or $C(=O)R^{12}NH_2$; $R^{14}$ is $C_{1-6}$ alkyl; $X^2$ is a bond; p is 0; n is 2; and, $R^{12}$ is as defined herein above.

In another embodiment of the present invention there is provided a method for treating an HIV infection, or treating AIDS or ARC, comprising administering to a host in need thereof a therapeutically effective amount of a compound of formula I wherein $X^1$ and $X^2$ are O; $R^3$ is hydrogen or halogen; $R^4$ is hydrogen, halogen or $C_{1-6}$ alkyl; $R^5$ is optionally substituted aryl; $R^{11c}$ is hydrogen; p is 1 to 6; and, $R^1$, $R^2$, $R^8$, $R^{8a}$, $R^9$, $R^{9a}$, $R^{10}$, $R^{11}$, $R^{11a}$, $R^{11b}$, $R^{12}$, $R^{13}$, $R^{14}$, $R^{15}$, Ar, $X^4$, $X^5$, $X^6$, n, o, r, s and u are as defined herein above.

In another embodiment of the present invention there is provided a method for treating an HIV infection, or treating AIDS or ARC, comprising administering to a host in need thereof a therapeutically effective amount of a compound selected from the group consisting of:
2-[4-Chloro-3-(3-chloro-5-cyano-phenoxy)-2-fluoro-phenyl]-N-(2-chloro4-sulfamoyl-phenyl)-acetamide;
2-[4-chloro-3-(3-chloro-5-cyano-phenoxy)-2-fluoro-phenyl]-N-(2-chloro4-propionylsulfamoyl-phenyl)-acetamide; sodium salt;
2-[3-(3-chloro-5-cyano-phenoxy)-2-fluoro4-methyl-phenyl]-N-(2-chloro4-sulfamoyl-phenyl)-acetamide;
2-[4-bromo-3-(3-chloro-5-cyano-phenoxy)-2-fluoro-phenyl]-N-(2-chloro4-sulfamoyl-phenyl)-acetamide;
2-[4-bromo-3-(3-chloro-5-cyano-phenoxy)-2-fluoro-phenyl]-N-(2-chloro4-propionylsulfamoyl-phenyl)-acetamide; sodium salt;
N-(4-butyrylsulfamoyl-2-chloro-phenyl)-2-[4-chloro-3-(3-chloro-5-cyano-phenoxy)-2-fluoro-phenyl]-acetamide; sodium salt;
N-[4-((S)-2-amino-3-methyl-butyrylsulfamoyl)-2-chloro-phenyl]-2-[4-chloro-3-(3-chloro-5-cyano-phenoxy)-2-fluoro-phenyl]-acetamide; sodium salt;
N-(2-chloro4-sulfamoyl-phenyl)-2-[3-(3-cyano-5-difluoromethyl-phenoxy)4-ethyl-2-fluoro-phenyl]-acetamide;
2-[3-(3-cyano-5-difluoromethyl-phenoxy)4-ethyl-2-fluoro-phenyl]-N-(2-methyl4-sulfamoyl-phenyl)-acetamide;
2-[4-bromo-3-(3-chloro-5-cyano-phenoxy)-2-fluoro-phenyl]-N-(2-methyl4-sulfamoyl-phenyl)-acetamide;
2-[4-bromo-3-(3-cyano-5-difluoromethyl-phenoxy)-2-fluoro-phenyl]-N-(2-methyl4-sulfamoyl-phenyl)-acetamide;
2-[4-bromo-3-(3-cyano-5-difluoromethyl-phenoxy)-2-fluoro-phenyl]-N-(2-chloro4-sulfamoyl-30 phenyl)-acetamide;
2-[4-chloro-3-(3-cyano-5-difluoromethyl-phenoxy)-2-fluoro-phenyl]-N-(2-methyl4-sulfamoyl-phenyl)-acetamide;
2-[3-(3-chloro-5-cyano-phenoxy)-2-fluoro4-methoxy-phenyl]-N-(2-chloro4-sulfamoyl-phenyl)-acetamide;
2-[3-(3-chloro-5-cyano-phenoxy)-2-fluoro4-methoxy-phenyl]-N-(2-methyl4-sulfamoyl-phenyl)-acetamide; and,
2-[3-(3-chloro-5-cyano-phenoxy)-2-fluoro4-methyl-phenyl]-N-(2-chloro4-proplonylsulfamoyl-phenyl)-acetamide; sodium salt;

wherein in each case the compound can either be a salt or a neutral form of the above.

In another embodiment of the present invention there is provided a method for treating an HIV infection, or treating AIDS or ARC, comprising co-administering to a host in need thereof a therapeutically effective amount of a compound of formula I wherein $R^1$, $R^2$, $R^3$, $R^4$, $R^5$, $R^8$, $R^{8a}$, $R^9$, $R^{9a}$, $R^{10}$, $R^{11}$, $R^{11a}$, $R^{11b}$, $R^{11c}$, $R^{12}$, $R^{13}$, $R^{14}$, $R^{15}$, Ar, $X^1$, $X^2$, $X^4$, $X^5$, $x^6$, n, o, p, r, s and u are as defined herein above and at least one compound selected from the group consisting of HIV protease inhibitors, nucleoside reverse transcriptase inhibitors, non-nucleoside reverse transcriptase inhibitors, CCR5 antagonists and viral fusion inhibitors.

In another embodiment of the present invention there is provided a method for treating an HIV infection, or treating AIDS or ARC, comprising co-administering to a host in need thereof a therapeutically effective amount of a compound of formula I wherein $R^1$, $R^2$, $R^3$, $R^4$, $R^5$, $R^8$, $R^{8a}$, $R^9$, $R^{9a}$, $R^{10}$, $R^{11}$, $R^{11a}$, $R^{11b}$, $R^{11c}$, $R^{12}$, $R^{13}$, $R^{14}$, $R^{15}$, Ar, $X^1$, $X^2$, $X^4$, $X^5$, $X^6$, n, o, p, r, s and u are as defined herein above and reverse transcriptase inhibitor is selected from the group consisting of zidovudine, lamivudine, didanosine, zalcitabine, stavudine, rescriptor, sustiva, viramune, efavirenz, nevirapine or delavirdine and/or the protease inhibitor is selected from the group consisting of saquinavir, ritonavir, nelfinavir, indinavir, amprenavir, lopinavir In another embodiment of the present invention there is provided a method for inhibiting HIV reverse transcriptase comprising administering to a host in need thereof a therapeutically effective amount of a compound of formula I wherein $R^1$, $R^2$, $R^3$, $R^4$, $R^5$, $R^8$, $R^{8a}$, $R^9$, $R^{9a}$, $R^{10}$, $R^{11}$, $R^{11a}$, $R^{11b}$, $R^{11c}$, $R^{12}$, $R^{13}$, $R^{14}$, $R^{15}$, Ar, $X^1$, $X^2$, $X^4$, $X^5$, $X^6$, n, o, p, r, s and u are as defined herein above In another embodiment of the present invention there is provided a method for inhibiting HIV reverse transcriptase containing at least one mutation compared to wild type virus comprising co-administering to a host in need thereof a therapeutically effective amount of a compound of formula I wherein $R^1$, $R^2$, $R^3$, $R^4$, $R^5$, $R^8$, $R^{8a}$, $R^9$, $R^{9a}$, $R^{10}$, $R^{11}$, $R^{11a}$, $R^{11b}$, $R^{11c}$, $R^{12}$, $R^{13}$, $R^{14}$, $R^{15}$, Ar, $X^1$, $X^2$, $X^4$, $X^5$, $X^6$, n, o, p, r, s and u are as defined herein above In another embodiment of the present invention there is provided a method for treating an HIV infection, or treating AIDS or ARC, caused by a strain of HIV with reduced sensitivity to therapy with efavirenz, nevirapine or delavirdine comprising co-administering to a host in need thereof a therapeutically effective amount of a compound of formula I wherein $R^1$, $R^2$, $R^3$, $R^4$, $R^5$, $R^8$, $R^{8a}$, $R^9$, $R^{9a}$, $R^{10}$, $R^{11}$, $R^{11a}$, $R^{11b}$, $R^{11c}$, $R^{12}$, $R^{13}$, $R^{14}$, $R^{15}$, Ar, $X^1$, $X^2$, $X^4$, $X^5$, $X^6$, n, o, p, r, s and u are as defined herein above In another embodiment of the present invention there is provided a pharmaceutical composition for treating an HIV infection, or treating AIDS or ARC, comprising a compound of formula I wherein $R^1$, $R^2$, $R^3$, $R^4$, $R^5$, $R^8$, $R^{8a}$, $R^9$, $R^{9a}$, $R^{10}$, $R^{11}$, $R^{11a}$, $R^{11b}$, $R^{11c}$, $R^{12}$, $R^{13}$, $R^{14}$, $R^{15}$, Ar, $X^1$, $X^2$, $X^4$, $X^5$, $X^6$, n, o, p, r, s and u are as defined herein above admixed with at least one pharmaceutically acceptable carrier, diluent or excipient.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth.

Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl refers to either an aryl or a heteroaryl group.

The term "$C_{1-6}$ alkyl" as used herein denotes an unbranched or branched chain, saturated, monovalent hydrocarbon residue containing 1 to 6 carbon atoms. Examples of alkyl groups include, but are not limited to, lower alkyl groups include methyl, ethyl, propyl, i-propyl, n-butyl, i-butyl, t-butyl or pentyl, isopentyl, neopentyl, hexyl.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "$C_{3-8}$ cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl.

The term "aryl" as used herein means a monocyclic or polycyclic-aromatic group comprising carbon and hydrogen atoms. Examples of suitable aryl groups include, but are not limited to, phenyl, tolyl, indenyl, and 1- or 2-naphthyl, as well as benzo-fused carbocyclic moieties such as 5,6,7,8-tetrahydronaphthyl. An aryl group can be unsubstituted or substituted with one or more suitable substituents which substituents include $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, acyl, alkoxycarbonyl, carbamoyl, N-alkylcarbamoyl, N,N-dialkylcarbamoyl, nitro and cyano.

A "heteroaryl group" or "heteroaromatic" as used herein means a monocyclic- or polycyclic aromatic ring comprising up to 15 carbon atoms, hydrogen atoms, and one or more heteroatoms, preferably, 1 to 3 heteroatoms, independently selected from nitrogen, oxygen, and sulfur. As well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, pyridinyl, pyridine N-oxide, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, thienyl, isoxazolyl, indole, indole N-oxide, quinoline, quinoline N-oxide and oxazolyl. A heteroaryl group can be unsubstituted or substituted with one or more suitable substituents selected from hydroxy, oxo, cyano, alkyl, alkoxy, haloalkoxy, alkylthio, halo, haloalkyl, nitro, alkoxycarbonyl, amino, alkylamino, dialkylamino, aminoacyl, alkylsulfonyl, arylsulfinyl, alkoxycarbonyl, carbamoyl, N-alkylcarbamoyl, N,N-dialkylcarbamoyl, acyl unless otherwise indicated.

The term "heterocyclyl" means the monovalent saturated cyclic radical, consisting of one or more rings, preferably one to two rings, of three to eight atoms per ring, incorporating one or more ring heteroatoms (chosen from N, O or $S(O)_{0-2}$), and which can optionally be substituted with one or more, preferably one to three substituents selected from hydroxy, oxo, cyano, alkyl, alkoxy, haloalkoxy, alkylthio, halo, haloalkyl, nitro, alkoxycarbonyl, amino, alkylamino, dialkylamino, aminoacyl, alkylsulfonyl, arylsulfinyl, alkoxycarbonyl, carbamoyl, N-alkylcarbamoyl, N,N-dialkylcarbamoyl, acyl unless otherwise indicated. Examples of heterocyclic radicals include, but are not limited to, furanyl, tetrahydropyranyl, tetrahydrothiophenyl and the like. A nitrogen atom in the heteroaryl ring can optionally be an N-oxide.

The term "alkoxy group" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, heptyloxy including their isomers.

The term "alkylthio group" as used herein means an —S-alkyl group, wherein alkyl is as defined above such as methylthio, ethylthio, n-propylthio, i-propylthio, n-butylthio, i-butylthio, t-butylthio, pentylthio including their isomers.

The term "haloalkoxy group" as used herein means an —O-haloalkyl group, wherein haloalkyl is as defined above. Examples of haloalkoxy groups include, but are not limited to, 2,2,2-trifluoroethoxy, difluoromethoxy and 1,1,1,3,3,3-hexafluoro-iso-propoxy.

The term "haloalkthio group" as used herein means an —S-haloalkyl group, wherein haloalkyl is as defined above. An example of haloalkthio group includes, but are not limited to, 2,2,2-trifluoroeththanthiol.

The term "aryloxy group" as used herein means an O-aryl group wherein aryl is as defined above. An aryloxy group can be unsubstituted or substituted with one or more suitable substituents. Preferably, the aryl ring of an aryloxy group is a monocyclic ring, wherein the ring comprises 6 carbon atoms, referred to herein as "($C_6$) aryloxy". The term "optionally substituted aryloxy" means the aryl or group may be substituted with one to three groups selected from the group consisting of $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, acyl, alkoxycarbonyl, carbamoyl, N-alkylcarbamoyl, N,N-dialkylcarbamoyl, nitro and cyano.

The term "heteroaryloxy group" as used herein means an O-heteroaryl group, wherein heteroaryl is as defined above. The heteroaryl ring of a heteroaryloxy group can be unsubstituted or substituted with one or more suitable substituents. Examples of heteroaryl groups include, but are not limited to, 2-pyridyloxy, 3-pyrrolyloxy, 3-pyrazolyloxy, 2-imidazolyloxy, 3-pyrazinyloxy, and 4-pyrimidyloxy.

The term "acyl" or "alkylcarbonyl" as used herein denotes a radical of formula C(=O)R wherein R is hydrogen, unbranched or branched alkyl containing 1 to 6 carbon atoms or a phenyl group.

The term "alkoxycarbonyl" as used herein denotes a radical of formula C(=O)OR wherein R is, unbranched or branched alkyl as described above.

The term "acylamino" as used herein denotes a radical of formula —NH-(acyl) where acyl is as defined herein.

The term "arylboronic acid" as used herein denotes a radical of formula $ArB(OH)_2$ wherein Ar is an optionally substituted aryl group as described above.

The term "alkylene" as used herein denotes a divalent linear or branched saturated hydrocarbon radical, having from one to six carbons inclusive, unless otherwise indicated. Examples of alkylene radicals include, but are not limited to, methylene, ethylene, propylene, 2-methyl-propylene, butylene, 2-ethylbutylene.

The term "arylalkyl" or "aralkyl" as used herein denotes the radical R'R"—, wherein R' is an aryl radical as defined herein, and R" is an alkylene radical as defined herein and the arylalkyl group is attached through the alkylene radical. Examples of arylalkyl radicals include, but are not limited to, benzyl, phenylethyl, 3-phenylpropyl.

The term "halogen" as used herein means fluorine, chlorine, bromine, or iodine. Correspondingly, the meaning of the term "halo" encompasses fluoro, chloro, bromo, and iodo. The term "hydrohalic acid" refers to an acid comprised of hydrogen and a halogen.

The term "alkylsulfinyl" as used herein means the radical —S(O)R', wherein R' is alkyl as defined herein. Examples of alkylaminosulfonyl include, but are not limited to methylsulfinyl and iso-propylsulfinyl.

The term "alkylsulfonyl" as used herein means the radical —$S(O)_2R'$, wherein R' is alkyl as defined herein. Examples of alkylaminosulfonyl include, but are not limited to methylsulfonyl and iso-propylsulfonyl.

The terms "amino", "alkylamino" and "dialkylamino" as used herein refer to —$NH_2$, —NHR and —$NR_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to $NH_2(CH_2)_n$—, $RHN(CH_2)_n$—, and $R_2N(CH_2)_n$— respectively wherein n is 1 to 6 and R is alkyl as defined above The prefix "carbamoyl" as used herein means the radical —$CONH_2$. The prefix "N-alkylcabamoyl" and "N,N-dialkylcarbamoyl" means the radical CONHR' or CONR'R" respectively wherein the R' and R" groups are independently alkyl as defined herein.

The term "amino acid" as used herein refers to naturally occurring amino acids, as well as to optical isomers (enantiomers and diastereomers), synthetic analogs and derivatives thereof. α-Amino acids comprise a carbon atom bonded to a carboxyl group, an amino group, a hydrogen atom and a unique "side chain" group. The term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, omithine and lysine. The side chains of naturally occurring amino acids include: hydrogen, methyl, iso-propyl, iso-butyl, sec-butyl, —$CH_2OH$, —$CH(OH)CH_3$, —$CH_2SH$, —$CH_2CH_2SMe$, —$(CH_2)_pCOR$ wherein R is —OH or —$NH_2$ and p is 1 or 2, —$(CH_2)_q$—$NH_2$ where q is 3 or 4, —$(CH_2)_3$—NHC(=NH)$NH_2$, —$CH_2C_6H_5$, —$CH_2$-p-$C_6H_4$—OH, (3-indolinyl)methylene, (4-imidazolyl)methylene.

The term "conjugate base" as used herein means the chemical species produced when a proton is abstracted from an acid (including here a carbon acid).

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings and the present invention encompasses all tautomeric forms of the compounds.

Compounds of formula I which are basic can form pharmaceutically acceptable acid addition salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluenesulfonic acid, and the like).

A "prodrug" of a compound of formula (I) herein refers to any compound which releases an active drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the compound of Formula I. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of produgs include N-acyl-benzenesulfonamide described.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e. g., channels) that have a guest molecule (e. g., a solvent or water) trapped within.

The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system.

The term "nucleoside and nucleotide reverse transcriptase inhibitors" ("NRTI's) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename; didanosine (ddl) available under the VIDEX tradename.; zalcitabine (ddC) available under the HIVID tradename; stavudine (d4T) available under the ZERIT trademark.; lamivudine (3TC) available under the EPIVIR tradename; abacavir (1592U89) disclosed in WO96/30025 and available under the ZIAGEN trademark; adefovir dipivoxil [bis(POM)-PMEA] available under the PREVON tradename; lobucavir (BMS-180194), a nucleoside reverse transcriptase inhibitor disclosed in EP-0358154 and EP-0736533 and under development by Bristol-Myers Squibb; BCH-10652, a reverse transcriptase inhibitor (in the form of a racemic mixture of BCH-10618 and BCH-10619) under development by Biochem Pharma; emitricitabine [(−)-FTC] licensed from Emory University under U.S. Pat. No. 5,814,639 and under development by Triangle Pharmaceuticals; beta-L-FD4 (also called beta-L-D4C and named beta-L-2', 3'-dicleoxy-5-fluoro-cytidene) licensed by Yale University to Vion Pharmaceuticals; DAPD, the purine nucleoside, (−)-beta-D-2,6,-diamino-purine dioxolane disclosed in EP-0656778 and licensed to Triangle Pharmaceuticals; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc.

The term "non-nucleoside reverse transcriptase inhibitors" ("NNRTI's) as used herein means non-nucleosides that inhibit the activity of HIV-1 reverse transcriptase.

Typical suitable NNRTIs include nevirapine (BI-RG-587) available under the VIRAMUNE tradename; delaviradine (BHAP, U-90152) available under the RESCRIPTOR tradename; efavirenz (DMP-266) a benzoxazin-2-one disclosed in WO94/03440 and available under the SUSTIVA tradename; PNU-142721, a furopyridine-thio-pyrimide; AG-1549 (formerly Shionogi #S-1 153); 5-(3,5-dichlorophenyl)-thio4-isopropyl-1-(4-pyridyl)methyl-1H-imidazol-2-ylmethyl carbonate disclosed in WO 96/10019; MKC-442 (1-(ethoxymethyl)-5-(1-methylethyl)-6-(phenylmethyl)-(2,4(1 H, 3H)-pyrimidinedione); and (+)-calanolide A (NSC-67545 1) and B, coumarin derivatives disclosed in U.S. Pat. No. 5,489,697.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN as well as nonpeptide protease inhibitors e.g., VIRACEPT.

Typical suitable PIs include saquinavir available in hard gel capsules under the INVIRASE tradename and as soft gel capsules under the FORTOVASE tradename; ritonavir (ABT-538) available under the NORVIR tradename; indinavir (MK-639) available under the CRIXIVAN tradename; nelfnavir (AG-1343) available under the VIRACEPT; amprenavir (141W94), tradename AGENERASE, a non-peptide protease inhibitor; lasinavir (BMS-234475; originally discovered by Novartis, Basel, Switzerland (CGP-61755); DMP-450, a cyclic urea discovered by Dupont; BMS-2322623, an azapeptide under development by Bristol-Myers Squibb, as a 2nd-generation HIV-1 PI; ABT-378; AG-1 549 an orally active imidazole carbamate.

Other antiviral agents include hydroxyurea, ribavirin, IL-2, IL-12, pentaftiside and Yissum Project No. 11607. Hydroxyurea (Droxia), a ribonucleoside triphosphate reductase inhibitor, the enzyme involved in the activation of T-cells. Hydroxyurea was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530, 787, 4,569,790, 4,604,377, 4,748,234, 4,752,585, and 4,949, 314, and is available under the PROLEUKIN (aldesleukin) tradename as a lyophilized powder for IV infusion or sc administration upon reconstitution and dilution with water; a dose of about 1 to about 20 million 1U/day, sc is preferred; a dose of about 15 million I U/day, sc is more preferred. IL-12 is disclosed in WO96/25171 and is available as a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 and available under the FUZEON tradename; pentafuside acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein. Ribavirin, 1-.beta.-D-ribofuranosyl-1H-1,2,4-triazole-3-carboxamide, is described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include: (a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4$^+$ and HIV-1-RNA plasma levels should be monitored every 3-6 months. Should viral load plateau, a fourth drug, e.g., one PI or one NNRTI could be added.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride (BOC$_2$O), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), MeSO$_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylpyrrolidone (NMP), 1,2-dichloroethane (DCE), pyridinium chlorochromate (PCC), N,N'-dicyclohexylcarbodiitmide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), diethyl iso-propylamine (DEIPA), pyridine (pyr), di-iso-butylaluminumhydride (DIBAL-H), room temperature, rt or RT, N,N-dimethyl acetamide (DMA), tert-butyldimethylsilyl or t-BuMe$_2$Si, (TBDMS), 4-N,N-dimethylarinopyridine (DMAP), triethyl amine (Et$_3$N or TEA), N,N-di methyl formamide (DMF), triflate or CF$_3$SO$_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether (Et$_2$O), trimethylsilyl or Me$_3$Si (TMS), ethyl (Et), p-toluenesulfonic acid monohydrate (TsOH or pTsOH), lithium hexamethyl disilazane (LiHMDS), 4-Me-C$_6$H$_4$SO$_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Examples of representative compounds encompassed by the present invention and within the scope of the invention are contained in the Table 1. The compounds in Table 1 and the preparative examples which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

| Cpd. No. | NAME | MS | MP |
|---|---|---|---|
| I-1 | 2-[4-Chloro-3-(3-chloro-5-cyano-phenoxy)-phenyl]-N-(4-sulfamoyl-phenyl)-acetamide | | 210.5-214.0 |
| I-2 | 2-[4-Chloro-3-(3,5-dicyano-phenoxy)-phenyl]-N-(4-sulfamoyl-phenyl)-acetamide | | 218-219 |
| I-3 | 2-[3-(2-Bromo-5-chloro-phenoxy)-4-chloro-phenyl]-N-[2-methyl-4-(3-sulfamoyl-propoxy)-phenyl]-acetamide | | 190.1-192.2 |
| I-4 | 2-[3-(2-Bromo-5-chloro-phenoxy)-4-chloro-phenyl]-N-(4-sulfamoyl-phenyl)-acetamide | | 260.1-261.9 |
| I-5 | 2-[4-Chloro-3-(3,5-dicyano-phenoxy)-phenyl]-N-(2-chloro-phenyl)-acetamide | 422 (M + H)$^+$ | |
| I-6 | 2-[4-Chloro-3-(3,5-dicyano-phenoxy)-phenyl]-N-(4-dimethylamino-phenyl)-acetamide | 431 (M + H)$^+$ | |
| I-7 | 2-[3-(2-Chloro-5-cyano-phenoxy)-4-ethyl-2-fluoro-phenyl]-N-(4-sulfamoyl-phenyl)-acetamide | | |
| I-8 | 2-[4-Chloro-3-(2,5-dicyano-phenoxy)-2-fluoro-phenyl]-N-(4-sulfamoyl-phenyl)-acetamide | 483 (M − H)$^-$ | |
| I-9 | 2-[4-Chloro-3-(3,5-dicyano-phenoxy)-2-fluoro-phenyl]-N-(4-sulfamoyl-phenyl)-acetamide | 483 (M − H)$^-$ | 135.7-138.1 |
| I-10 | 2-[4-Chloro-2-fluoro-3-(2,3,5-trichloro-phenoxy)-phenyl]-N-(4-sulphomyl-phenyl)-acetamide | 537 (M − H)$^-$ | 247.0-249.9 |
| I-11 | 2-[3-(3-Cyano-5-fluoro-phenoxy)-4-methyl-phenyl]-N-(4-sulfamoyl-phenyl)-acetamide | 440 (M + H)$^+$ | 165.8-168.1 |

TABLE 1-continued

| Cpd. No. | NAME | MS | MP |
|---|---|---|---|
| I-12 | N-(2-Chloro-phenyl)-2-[3-(3-cyano-5-fluoro-phenoxy)-4-methyl-phenyl]-acetamide | 395 (M + H)+ | 131.1-132.2 |
| I-13 | 2-[4-Chloro-3-(3-cyano-5-difluoromethyl-phenoxy)-2-fluoro-phenyl]-N-(4-sulfamoyl-phenyl)-acetamide | | 214-218 |
| I-14 | 2-[4-Chloro-3-(3-cyano-5-difluoromethyl-phenoxy)-2-fluoro-phenyl]-N-(2-chloro-phenyl)-acetamide | | 169.5-171.0 |
| I-15 | 2-[3-(2-Bromo-5-chloro-phenoxy)-4-ethyl-phenyl]-N-(4-sulfamoyl-phenyl)-acetamide | | 193.7-195.9 |
| I-16 | 2-[3-(2-Bromo-5-chloro-phenoxy)-4-ethyl-phenyl]-N-(2-chloro-phenyl)-acetamide | | 154-155.5 |
| I-17 | 2-[3-(5-Chloro-2-cyano-phenoxy)-4-ethyl-phenyl]-N-(4-sulfamoyl-phenyl)-acetaimde | | 198.1-202.6 |
| I-18 | 2-[3-(5-Chloro-2-cyano-phenoxy)-4-ethyl-phenyl]-N-(2-chloro-phenyl)-acetamide | | 168-169.9 |
| I-19 | 2-[3-(2,5-Dichloro-phenoxy)-4-ethyl-phenyl]-N-(4-sulfamoyl-phenyl)-acetamide | | 190-193.4 |
| I-20 | 2-[3-(2,6-Dichloro-phenoxy)-4-ethyl-phenyl]-N-(4-sulfamoyl-phenyl)-acetamide | | 222.5-225 |
| I-21 | N-(2-Chloro-phenyl)-2-[3-(2,5-dichloro-phenoxy)-4-ethyl-phenyl]-acetamide | | 146.3-147.1 |
| I-22 | 2-[3-(3-Bromo-5-chloro-phenoxy)-4-ethyl-phenyl]-N-(4-sulfamoyl-phenyl)-acetamide | | 216.1-221.3 |
| I-23 | N-(2-Chloro-phenyl)-2-[3-(2,6-dichloro-phenoxy)-4-ethyl-phenyl]-acetamide | | 107.0-110.5 |
| I-24 | 2-[3-(3-Bromo-5-chloro-phenoxy)-4-ethyl-phenyl]-N-(2-chloro-phenyl)-acetamide | | 119.9-122.2 |
| I-25 | N-(2-Chloro-phenyl)-2-[3-(3,5-dicyano-phenoxy)-4-ethyl-phenyl]-acetamide | 416 (M + H)+ | |
| I-26 | 2-[3-(2-Bromo-5-chloro-phenoxy)-4-isopropyl-phenyl]-N-(4-sulfamoyl-phenyl)-acetamide | | 204.1-206.7 |
| I-27 | 2-[3-(2-Bromo-5-chloro-phenoxy)-4-isopropyl-phenyl]-N-(2-chloro-phenyl)-acetamide | | 142.9-143.6 |
| I-28 | 2-[4-Chloro-3-(3,5-dicyano-phenoxy)-2-fluoro-phenyl]-N-(2-chloro-phenyl)-acetamide | | 182.6-196.5 |
| I-29 | 2-[4-Chloro-3-(3,5-dicyano-phenoxy)-phenyl]-N-[2-methyl-4-(3-sulfamoyl-propoxy)-phenyl]-acetamide | 539 (M)+ | |
| I-30 | 2-[3-(2-Bromo-5-chloro-phenoxy)-4-methyl-phenyl]-N-(4-sulfamoyl-phenyl)-acetamide | | 236.9-239.3 |
| I-31 | 2-[3-(2-Bromo-5-chloro-phenoxy)-4-methyl-phenyl]-N-(2-methyl-4-sulfamoyl-phenyl)-acetamide | | 200.5-203.5 |
| I-32 | 2-[4-Chloro-3-(3,5-dicyano-phenoxy)-2-fluoro-phenyl]-N-(2-methyl-4-sulfamoyl-phenyl)-acetamide | 499 (M + H)+ | 248.4-250.8 |
| I-33 | 2-[3-(2-Bromo-5-chloro-phenoxy)-4-methyl-phenyl]-N-(2-chloro-phenyl)-acetamide | | 133.9-135.9 |
| I-34 | N-(2-Chloro-phenyl)-2-[3-(3,5-dicyano-phenoxy)-4-methyl-phenyl]-acetamide | | 175.1-177.5 |
| I-35 | 2-[3-(3-Bromo-2,5-dichloro-phenoxy)-4-ethyl-phenyl]-N-(4-sulfamoyl-phenyl)-acetamide | | 206.9-209.9 |
| I-36 | 2-[3-(3-Bromo-2,5-dichloro-phenoxy)-4-ethyl-phenyl]-N-(2-methyl-4-sulfamoyl-phenyl)-acetamide | | 213.2-219.6 |
| I-37 | 2-[3-(3-Bromo-2,5-dichloro-phenoxy)-4-ethyl-phenyl]-N-(2-chloro-phenyl)-acetamide | | 146.5-147.6 |
| I-38 | N-(2-Chloro-phenyl)-2-[3-(3,5-dibromo-2-chloro-phenoxy)-4-ethyl-phenyl]-acetamide | | 155.5-155.8 |
| I-39 | 2-[3-(5-Bromo-2-chloro-3-fluoro-phenoxy)-4-ethyl-phenyl]-N-(4-sulfamoyl-phenyl)-acetamide | | 209.9-211.1 |
| I-40 | 2-[3-(5-Bromo-2-chloro-3-fluoro-phenoxy)-4-ethyl-phenyl]-N-(2-methyl-4-sulfamoyl-phenyl)-acetamide | | 207.0-209.9 |
| I-41 | 2-[3-(5-Bromo-2-chloro-3-fluoro-phenoxy)-4-ethyl-phenyl]-N-(2-chloro-phenyl)-acetamide | | 146.6-147.2 |
| I-42 | 2-[4-Chloro-3-(3-chloro-5-cyano-phenoxy)-2-fluoro-phenyl]-N-(methyl-4-sulfamoyl-phenyl)-acetamide | 509 (M + H)+ | 254.7-260.0 |
| I-43 | 2-[3-(3,5-Dicyano-phenoxy)-4-methyl-phenyl]-N-(2-methyl-4-sulfamoyl-phenyl)-acetamide | 459 (M − H)− | 228.6-230.9 |
| I-44 | N-(2-Chloro-4-sulfamoyl-phenyl)-2-[3-(3,5-dicyano-phenoxy)-4-methyl-phenyl]-acetamide | 479 (M − H)− | 209.9-211.5 |
| I-45 | 2-[3-(3-Chloro-5-cyano-phenoxy)-4-ethyl-phenyl]-N-(4-sulfamoyl-phenyl)-acetamide | 468 (M − H)− | 170.7-172.4 |
| I-46 | 2-[3-(3-Chloro-5-cyano-phenoxy)-4-ethyl-phenyl]-N-(2-methyl-4-sulfamoyl-phenyl)-acetamide | 482 (M − H)− | 189.1-189.4 |

TABLE 1-continued

| Cpd. No. | NAME | MS | MP |
|---|---|---|---|
| I-47 | 2-[3-(3-Chloro-5-cyano-phenoxy)-4-ethyl-phenyl]-N-(2-chloro-4-sulfamoyl-phenyl)-acetamide | 502 (M − H)⁻ | 181.1-183.9 |
| I-48 | 2-[3-(3-Chloro-5-cyano-phenoxy)-4-ethyl-phenyl]-N-(4-methylsulfamoyl-phenyl)-acetamide | 482 (M − H)⁻ | 149.1-151.3 |
| I-49 | 2-[3-(2-Chloro-5-cyano-3-fluoro-phenoxy)-4-ethyl-phenyl]-N-(4-sulfamoyl-phenyl)-acetamide | 486 (M − H)⁻ | 167.9-170.5 |
| I-50 | 2-[3-(2-Chloro-5-cyano-3-fluoro-phenoxy)-4-ethyl-phenyl]-N-(2-methyl-4-sulfamoyl-phenyl)-acetamide | 500 (M − H)⁻ | 217.6-220.4 |
| I-51 | 2-[4-Chloro-3-(3-chloro-5-cyano-phenoxy)-2-fluoro-phenyl]-N-(2-methyl-4-propionylsulfamoyl-phenyl)-acetamide | 563 (M − H)⁻ | 163.3-205.3 |
| I-52 | 2-[3-(2-Chloro-3,5-dicyano-phenoxy)-4-ethyl-phenyl]-N-(4-sulfamoyl-phenyl)-acetamide | 493 (M − H)⁻ | 119.7-123.3 |
| I-53 | 2-[3-(2-Chloro-3,5-dicyano-phenoxy)-4-ethyl-phenyl]-N-(2-methyl-4-sulfamoyl-phenyl)-acetamide | 507 (M − H)⁻ | 199.4-205.3 |
| I-54 | 2-[3-(2-Chloro-3,5-dicyano-phenoxy)-4-ethyl-phenyl]-N-(2-chloro-4-sulfamoyl-phenyl)-acetamide | 527 (M − H)⁻ | 180.3-183.1 |
| I-55 | 2-[4-Chloro-3-(4-cyano-2,6-dimethyl-phenoxy)-phenyl]-N-(4-sulfamoyl-phenyl)-acetamide | 468 (M − H)⁻ | 227.3-231.4 |
| I-56 | 2-[4-Chloro-3-(4-cyano-2,6-dimethyl-phenoxy)-phenyl]-N-(2-methyl-4-sulfamoyl-phenyl)-acetamide | 482 (M − H)⁻ | 232.1-234.6 |
| I-57 | 2-[3-(3-Chloro-5-cyano-phenoxy)-4-methoxy-phenyl]-N-(4-sulfamoyl-phenyl)-acetamide | 472 (M + H)⁺ | 218.3-221.4 |
| I-58 | 2-[3-(3-Chloro-5-cyano-phenoxy)-4-ethyl-phenyl]-N-(2-chloro-phenyl)-acetamide | 425 (M + H)⁺ | x |
| I-59 | 2-[3-(2-Chloro-5-cyano-3-fluoro-phenoxy)-4-ethyl-phenyl]-N-(2-chloro-phenyl)-acetamide | 443 (M + H)⁺ | 142.1-142.8 |
| I-60 | 2-[3-(2-Chloro-3,5-dicyano-phenoxy)-4-ethyl-phenyl]-N-(2-chloro-phenyl)-acetamide | 450 (M + H)⁺ | 110.0-111.5 |
| I-61 | 2-[3-(3-Chloro-5-cyano-phenoxy)-4-methoxy-phenyl]-N-(2-chloro-phenyl)-acetamide | 427 (M + H)⁺ | 175.7-178.3 |
| I-62 | 2-[3-(2-Chloro-5-cyano-phenoxy)-4-methoxy-phenyl]-N-(2-chloro-phenyl)-acetamide | 427 (M + H)⁺ | 194.0-197.8 |
| I-63 | 2-[4-Bromo-3-(3-chloro-5-cyano-phenoxy)-2-fluoro-phenyl]-N-(2-chloro-4-propionylsulfamoyl-phenyl)-acetamide; sodium salt | 630 (M + H)⁺ | 164.8-166.2 |
| I-64 | 2-[3-(3-Chloro-5-cyano-phenoxy)-4-methoxy-phenyl]-N-(2-chloro-4-sulfamoyl-phenyl)-acetamide | 505 (M)⁺ | 186.3-189.7 |
| I-65 | 2-[3-(2-Chloro-5-cyano-phenoxy)-4-methoxy-phenyl]-N-(4-sulfamoyl-phenyl)-acetamide | 471 (M)⁺ | 252.3-254.3 |
| I-66 | 2-[3-(2-Chloro-5-cyano-phenoxy)-4-methoxy-phenyl]-N-(2-methyl-4-sulfamoyl-phenyl)-acetamide | 485 (M)⁺ | 232.9-236.9 |
| I-67 | 2-[3-(2-Chloro-5-cyano-phenoxy)-4-methoxy-phenyl]-N-(2-chloro-4-sulfamoyl-phenyl)-acetamide | 505 (M)⁺ | 214.6-216.4 |
| I-68 | 2-[4-Chloro-3-(4-cyano-2,6-dimethyl-phenoxy)-phenyl]-N-(2-chloro-phenyl)-acetamide | 425 (M + H)⁺ | 183.9-185.1 |
| I-69 | 2-[4-Chloro-3-(3,5-dicyano-phenoxy)-phenyl]-N-(4-methylsulfamoyl-phenyl)-acetamide | | |
| I-70 | 2-[4-Chloro-3-(3,5-dicyano-phenoxy)-phenyl]-N-(4-dimethylsulfamoyl-phenyl)-acetamide | | |
| I-71 | 2-[4-Chloro-3-(3,5-dicyano-phenoxy)-phenyl]-N-[4-(piperidine-1-sulfonyl)-phenyl]-acetamide | | |
| I-72 | 2-[4-Chloro-3-(3,5-dicyano-phenoxy)-phenyl]-N-[4-(morpholine-4-sulfonyl)-phenyl]-acetamide | | |
| I-73 | 2-[3-(3-Chloro-5-cyano-phenoxy)-4-methoxy-phenyl]-N-(2-methyl-4-sulfamoyl-phenyl)-acetamide | 484 (M − H)⁻ | 222.3-224.3 |
| I-74 | 2-[3-(3-Chloro-5-cyano-phenoxy)-2-fluoro-4-methyl-phenyl]-N-(2-methyl-4-sulfamoyl-phenyl)-acetamide | 486 (M − H)⁻ | 230.0-232.2 |
| I-75 | 2-[4-Chloro-3-(3-cyano-5-difluoromethyl-phenoxy)-2-fluoro-phenyl]-N-(2-methyl-4-sulfamoyl-phenyl)-acetamide | 524 (M + H)⁺ | x |
| I-76 | 2-[4-Chloro-3-(3,5-dicyano-phenoxy)-phenyl]-N-(2-chloro-4-methanesulfonyl-phenyl)-acetamide | | |
| I-77 | N-[4-((S)-2-Amino-3-methyl-butyrylsulfamoyl)-2-methyl-phenyl]-2-[4-chloro-3-(3-chloro-5-cyano-phenoxy)-2-fluoro-phenyl]-acetamide; compound with hydrochloric acid | 607 (M + H)⁺ | 169.0-180.3 |
| I-78 | 2-[4-Chloro-3-(3,5-dicyano-phenoxy)-phenyl]-N-(4-cyanomethoxy-phenyl)-acetamide | | |

TABLE 1-continued

| Cpd. No. | NAME | MS | MP |
|---|---|---|---|
| I-79 | 2-[4-Chloro-3-(3,5-dicyano-phenoxy)-phenyl]-N-(4-methanesulfonyl-phenyl)-acetamide | | |
| I-80 | 3-Chloro-4-{2-[4-chloro-3-(3,5-dicyano-phenoxy)-phenyl]-acetylamino}-benzoic acid methyl ester | | |
| I-81 | 2-[4-Chloro-3-(3,5-dicyano-phenoxy)-phenyl]-N-{4-[(2-hydroxy-ethyl)-methyl-sulfamoyl]-phenyl}-acetamide | | |
| I-82 | 2-[4-Chloro-3-(3,5-dicyano-phenoxy)-phenyl]-N-[4-(4-hydroxy-piperidine-1-sulfonyl)-phenyl]-acetamide | | |
| I-83 | 2-[3-(3-Chloro-5-cyano-phenoxy)-2-fluoro-4-methyl-phenyl]-N-(2-chloro-4-sulfamoyl-phenyl)-acetamide | 506 (M − H)$^-$ | 228.9-230.6 |
| I-84 | N-(2-Chloro-4-sulfamoyl-phenyl)-2-[3-(3-cyano-5-difluoromethyl-phenoxy)-2-fluoro-4-methyl-phenyl]-acetamide | 522 (M − H)$^-$ | 218.0-218.7 |
| I-85 | 2-[3-(3-Cyano-5-difluoromethyl-phenoxy)-2-fluoro-4-methyl-phenyl]-N-(2-methyl-4-sulfamoyl-phenyl)-acetamide | 504 (M + H)$^+$ | 218.0-220.4 |
| I-86 | N-(2-Chloro-phenyl)-2-[3-(3-cyano-5-difluoromethyl-phenoxy)-2-fluoro-4-methyl-phenyl]-acetamide | 445 (M + H)$^+$ | 163.3-164.4 |
| I-87 | 2-[4-Chloro-3-(3-chloro-5-cyano-phenoxy)-2-fluoro-phenyl]-N-{2-methyl-4-[(pyridine-3-carbonyl)-sulfamoyl]-phenyl}-acetamide; compound with hydrochloric acid | 613 (M + H)$^+$ | 261.8-263.6 |
| I-88 | 2-[4-Chloro-3-(3-cyano-5-trifluoromethyl-phenoxy)-phenyl]-N-(4-sulfamoyl-phenyl)-acetamide | 508 (M − H)$^-$ | 219-221.4 |
| I-89 | 2-[4-Chloro-3-(3-cyano-5-trifluoromethyl-phenoxy)-phenyl]-N-(2-methyl-4-sulfamoyl-phenyl)-acetamide | 522 (M − H)$^-$ | 211.6-214.6 |
| I-90 | 2-[4-Chloro-3-(3-cyano-5-trifluoromethyl-phenoxy)-phenyl]-N-(2-chloro-4-sulfamoyl-phenyl)-acetamide | 542 (M − H)$^-$ | 198.0-202.0 |
| I-91 | 2-[3-(3-Cyano-5-difluoromethyl-phenoxy)-4-ethyl-phenyl]-N-(4-sulfamoyl-phenyl)-acetamide | 486 (M + H)$^+$ | 188.0-198.0 |
| I-92 | 2-[3-(3-Cyano-5-difluoromethyl-phenoxy)-4-methoxy-phenyl]-N-(4-sulfamoyl-phenyl)-acetamide | 488 (M + H)$^+$ | 213.9-214.2 |
| I-93 | 2-[3-(3-Cyano-5-difluoromethyl-phenoxy)-4-methoxy-phenyl]-N-(2-methyl-4-sulfamoyl-phenyl)-acetamide | 502 (M + H)$^+$ | 175.0-177.2 |
| I-94 | N-(2-Chloro-4-sulfamoyl-phenyl)-2-[3-(3-cyano-5-difluoromethyl-phenoxy)-4-methoxy-phenyl]-acetamide | 520 (M − H)$^-$ | 185.0-187.9 |
| I-95 | 2-{4-Chloro-3-[3-cyano-5-(1,1-difluoro-ethyl)-phenoxy]-2-fluoro-phenyl}-N-(4-sulfamoyl-phenyl)-acetamide | 522 (M − H)$^-$ | 207.0-209.8 |
| I-96 | 2-{4-Chloro-3-[3-cyano-5-(1,1-difluoro-ethyl)-phenoxy]-2-fluoro-phenyl}-N-(2-methyl-4-sulfamoyl-phenyl)-acetamide | 538 (M + H)$^+$ | 198.5-201.0 |
| I-97 | 2-{4-Chloro-3-[3-cyano-5-(1,1-difluoro-ethyl)-phenoxy]-2-fluoro-phenyl}-N-(2-chloro-4-sulfamoyl-phenyl)-acetamide | 556 (M − H)$^-$ | 192.0-197.6 |
| I-98 | 2-[4-Chloro-3-(3-chloro-5-cyano-phenoxy)-2-fluoro-phenyl]-N-(2-chloro-phenyl)-acetamide | 448 (M − H)$^-$ | 181.3-184.0 |
| I-99 | 2-[4-Chloro-3-(3-chloro-5-cyano-phenoxy)-2-fluoro-phenyl]-N-[2-methyl-4-(methyl-propionyl-sulfamoyl)-phenyl]-acetamide | 578 (M + H)$^+$ | 212.0-216.9 |
| I-100 | 2-[4-Chloro-3-(3-chloro-5-cyano-phenoxy)-2-fluoro-phenyl]-N-(2-chloro-4-sulfamoyl-phenyl)-acetamide | | 234.4-234.9 |
| I-101 | 2-[3-(3-Cyano-5-difluoromethyl-phenoxy)-4-ethyl-phenyl]-N-(2-methyl-4-sulfamoyl-phenyl)-acetamide | 500 (M + H)$^+$ | |
| I-102 | 2-[3-(2-Chloro-5-cyano-phenoxy)-5-methoxy-phenyl]-N-(4-sulfamoyl-phenyl)-acetamide | 472 (M + H)$^+$ | 180.5-181.3 |
| I-103 | 2-[3-(2-Chloro-5-cyano-phenoxy)-5-methoxy-phenyl]-N-(2-methyl-4-sulfamoyl-phenyl)-acetamide | 486 (M + H)$^+$ | 179.8-184.0 |
| I-104 | 2-[4,5-Dibromo-3-(3-cyano-5-difluoromethyl-phenoxy)-2-fluoro-phenyl]-N-(2-methyl-4-sulfamoyl-phenyl)-acetamide | 646 (M + H)$^+$ | |
| I-105 | 2-[3-(2-Chloro-5-cyano-phenoxy)-5-ethyl-phenyl]-N-(4-sulfamoyl-phenyl)-acetamide | 470 (M + H)$^+$ | |

TABLE 1-continued

| Cpd. No. | NAME | MS | MP |
|---|---|---|---|
| I-106 | 2-[3-(2-Chloro-5-cyano-phenoxy)-5-ethyl-phenyl]-N-(2-methyl-4-sulfamoyl-phenyl)-acetamide | 484 (M + H)+ | 231.6-233.1 |
| I-107 | 2-[3-(2-Chloro-5-cyano-phenoxy)-5-ethyl-phenyl]-N-(2-chloro-4-sulfamoyl-phenyl)-acetamide | 503 (M)+ | 204.0-207.0 |
| I-108 | 2-[4-Chloro-3-(3-chloro-5-cyano-phenoxy)-2-fluoro-phenyl]-N-(2-methyl-4-methylsulfamoyl-phenyl)-acetamide | 522 (M + H)+ | 204.4-207.3 |
| I-109 | 2-[4-Bromo-3-(3-chloro-5-cyano-phenoxy)-2-fluoro-phenyl]-N-(2-chloro-4-sulfamoyl-phenyl)-acetamide | 572 (M − H)− | 165.0-166.6 |
| I-110 | 3-Chloro-4-{2-[3-(3-cyano-5-difluoromethyl-phenoxy)-2-fluoro-4-methyl-phenyl]-acetylamino}-benzoic acid | 487 (M − H)− | 216.9-218.3 |
| I-111 | 2-[4-Chloro-3-(3-chloro-5-cyano-phenoxy)-2-fluoro-phenyl]-N-(2-chloro-phenyl)-N-methyl-acetamide | 463 (M + H)+ | 134.0-137.1 |
| I-112 | N-(2-Chloro-4-methanesulfonyl-phenyl)-2-[3-(3-cyano-5-difluoromethyl-phenoxy)-2-fluoro-4-methyl-phenyl]-acetamide | 521 (M − H)− | 179.9-182.0 |
| I-113 | 2-[3-(2-Chloro-5-cyano-phenoxy)-5-methoxy-phenyl]-N-(2-chloro-4-sulfamoyl-phenyl)-acetamide | 506 (M + H)+ | |
| I-114 | 2-[4,5-Dibromo-3-(3-cyano-5-difluoromethyl-phenoxy)-2-fluoro-phenyl]-N-(4-sulfamoyl-phenyl)-acetamide | 631 (M)+ | 144.0-147.0 |
| I-115 | 2-[3-(3-Chloro-5-cyano-phenoxy)-4-methyl-phenyl]-N-[2-methyl-4-(morpholine-4-sulfonyl)-phenyl]-acetamide | 540 (M + H)+ | |
| I-116 | 2-[3-(3-Chloro-5-cyano-phenoxy)-4-methyl-phenyl]-N-[2-methyl-4-(4-methyl-piperazine-1-sulfonyl)-phenyl]-acetamide | 553 (M + H)+ | |
| I-117 | 2-[3-(3-Chloro-5-cyano-phenoxy)-4-methyl-phenyl]-N-[2-methyl-4-(thiomorpholine-4-sulfonyl)-phenyl]-acetamide | 554 (M − H)− | 151.9-155.3 |
| I-118 | 2-[3-(3-Chloro-5-cyano-phenoxy)-4-methyl-phenyl]-N-[2-methyl-4-(2-morpholin-4-yl-ethylsulfamoyl)-phenyl]-acetamide | 581 (M − H)− | 177.0-181.0 |
| I-119 | 2-[3-(3-Chloro-5-cyano-phenoxy)-4-methyl-phenyl]-N-[4-(3-hydroxy-propylsulfamoyl)-2-methyl-phenyl]-acetamide | 528 (M + H)+ | |
| I-120 | 2-[4-Chloro-3-(3-cyano-5-trifluoromethyl-phenoxy)-2-fluoro-phenyl]-N-(2-methyl-4-sulfamoyl-phenyl)-acetamide | 540 (M − H)− | 212.0-216.1 |
| I-121 | 2-[3-(3-Chloro-5-cyano-phenoxy)-4-methyl-phenyl]-N-[4-(4-hydroxy-cyclohexylsulfamoyl)-2-methyl-phenyl]-acetamide | 568 (M + H)+ | 195.1-197.7 |
| I-122 | 2-[3-(3-Chloro-5-cyano-phenoxy)-4-methyl-phenyl]-N-(2-methyl-4-sulfamoyl-phenyl)-acetamide | 468 (M − H)− | 192.8-194.1 |
| I-123 | 2-[3-(3-Chloro-5-cyano-phenoxy)-4-methyl-phenyl]-N-(2-chloro-4-sulfamoyl-phenyl)-acetamide | 488 (M − H)− | 194.0-194.9 |
| I-124 | 2-[4-Chloro-3-(4-cyano-6-methyl-pyridin-2-yloxy)-2-fluoro-phenyl]-N-(2-methyl-4-sulfamoyl-phenyl)-acetamide | 489 (M + H)+ | 230.1-230.7 |
| I-125 | 3-(4-{2-[3-(3-Chloro-5-cyano-phenoxy)-4-methyl-phenyl]-acetylamino}-3-methyl-benzenesulfonyl)-propionic acid | 525 (M − H)− | 74.3-76.5 |
| I-126 | 2-[4-Chloro-3-(3-chloro-5-cyano-phenoxy)-2-fluoro-phenyl]-N-(2-chloro-4-propionylsulfamoyl-phenyl)-acetamide; sodium salt | | 155.4-157.5 |
| I-127 | N-[4-((S)-2-Amino-3-methyl-butyrylsulfamoyl)-2-chloro-phenyl]-2-[4-chloro-3-(3-chloro-5-cyano-phenoxy)-2-fluoro-phenyl]-acetamide; sodium salt | 627 (M + H)− | 219.4-220.2 |
| I-128 | 2-[3-(3-Chloro-5-cyano-phenoxy)-4-methyl-phenyl]-N-[2-methyl-4-(tetrahydro-pyran-4-ylsulfamoyl)-phenyl]-acetamide | 554 (M + H)+ | 171.7-172.6 |
| I-129 | 2-[3-(3-Chloro-5-cyano-phenoxy)-4-methyl-phenyl]-N-[4-(2-hydroxy-propylsulfamoyl)-2-methyl-phenyl]-acetamide | 528 (M + H)+ | 172.2-173.4 |
| I-130 | 2-[3-(3-Chloro-5-cyano-phenoxy)-4-methyl-phenyl]-N-[2-methyl-4-(2-methylsulfanyl-ethylsulfamoyl)-phenyl]-acetamide | 544 (M + H)+ | 155.6-156.6 |
| I-131 | 2-[3-(3-Chloro-5-cyano-phenoxy)-4-methyl-phenyl]-N-[2-methyl-4-(3-methylsulfanyl-propylsulfamoyl)-phenyl]-acetamide | 558 (M + H)+ | 159.9-162.8 |
| I-132 | 2-[3-(3-Chloro-5-cyano-phenoxy)-5-methoxy-phenyl]-N-(4-sulfamoyl-phenyl)-acetamide | 472 (M + H)+ | 184.1-185.5 |

TABLE 1-continued

| Cpd. No. | NAME | MS | MP |
|---|---|---|---|
| I-133 | 2-[3-(3-Chloro-5-cyano-phenoxy)-5-methoxy-phenyl]-N-(2-methyl-4-sulfamoyl-phenyl)-acetamide | 486 (M + H)+ | 169.9-171.1 |
| I-134 | N-(2-Chloro-4-sulfamoyl-phenyl)-2-[4,5-dibromo-3-(3-cyano-5-difluoromethyl-phenoxy)-2-fluoro-phenyl]-acetamide | 664 (M − H)− | |
| !-135 | 2-[4-Chloro-3-(4-cyano-2,6-dimethyl-phenoxy)-phenyl]-N-(2-chloro-4-sulfamoyl-phenyl)-acetamide | 502 (M − H)− | |
| I-136 | 2-[3-(3-Chloro-5-cyano-phenoxy)-5-methoxy-phenyl]-N-(2-chloro-4-sulfamoyl-phenyl)-acetamide | 505 (M)+ | 159.0-161.1 |
| I-137 | 2-[3-(3-Chloro-5-cyano-phenoxy)-4-methyl-phenyl]-N-[4-(2-cyano-ethanesulfonyl)-2-methyl-phenyl]-acetamide | 508 (M + H)+ | 186.1-188.0 |
| I-138 | N-(4-Butyrylsulfamoyl-2-chloro-phenyl)-2-[4-chloro-3-(3-chloro-5-cyano-phenoxy)-2-fluoro-phenyl]-acetamide; sodium salt | 598 (M + H)+ | 157.2-157.9 |
| I-139 | N-[4-(Butyryl-methyl-sulfamoyl)-2-chloro-phenyl]-2-[4-chloro-3-(3-chloro-5-cyano-phenoxy)-2-fluoro-phenyl]-acetamide | 612 (M + H)+ | 186.9-187.6 |
| I-140 | N-(2-Chloro-4-sulfamoyl-phenyl)-2-[3-(3-cyano-5-difluoromethyl-phenoxy)-4-ethyl-phenyl]-acetamide | 518 (M − H)− | 191.8-192.5 |
| I-141 | 2-[3-(3-Chloro-5-cyano-phenoxy)-5-methyl-phenyl]-N-(4-sulfamoyl-phenyl)-acetamide | 454 (M − H)− | 183.9-185.2 |
| I-142 | 2-[3-(3-Chloro-5-cyano-phenoxy)-5-methyl-phenyl]-N-(2-methyl-4-sulfamoyl-phenyl)-acetamide | 468 (M − H)− | 184.8-186.0 |
| I-143 | 2-[3-(3-Chloro-5-cyano-phenoxy)-5-methyl-phenyl]-N-(2-chloro-4-sulfamoyl-phenyl)-acetamide | 488 (M − H)− | 194.1-195.9 |
| I-144 | 2-[7-(3-Cyano-phenoxy)-benzofuran-5-yl]-N-(4-sulfamoyl-phenyl)-acetamide | 446 (M − H)− | 196.4-198.7 |
| I-145 | 2-[7-(3-Cyano-phenoxy)-benzofuran-5-yl]-N-(2-methyl-4-sulfamoyl-phenyl)-acetamide | 460 (M − H)− | 218.9-220.0 |
| I-146 | 2-[3-(2-Chloro-5-cyano-phenoxy)-5-methyl-phenyl]-N-(4-sulfamoyl-phenyl)-acetamide | 454 (M − H)− | 235.9-236.7 |
| I-147 | 2-[3-(2-Chloro-5-cyano-phenoxy)-5-methyl-phenyl]-N-(2-methyl-4-sulfamoyl-phenyl)-acetamide | 468 (M − H)− | 200.3-201.1 |
| I-148 | 2-[3-(2-Chloro-5-cyano-phenoxy)-5-methyl-phenyl]-N-(2-chloro-4-sulfamoyl-phenyl)-acetamide | 488 (M − H)− | 212.9-214.4 |
| I-149 | N-(2-Chloro-4-sulfamoyl-phenyl)-2-[7-(3,5-dichloro-phenoxy)-benzofuran-5-yl]-acetamide | 523 (M − H)− | 215.1-216.6 |
| I-150 | 2-[3-(3-Chloro-5-cyano-phenoxy)-4-methyl-phenyl]-N-[4-((S)-2,3-dihydroxy-propoxy)-2-methyl-phenyl]-acetamide | 481 (M + H)+ | 137.5-138.4 |
| I-151 | 2-[3-(3-Chloro-5-cyano-phenoxy)-4-methyl-phenyl]-N-[4-((R)-3,4-dihydroxy-butoxy)-2-methyl-phenyl]-acetamide | 495 (M + H)+ | 104.9-106.4 |
| I-152 | (4-{2-[3-(3-Chloro-5-cyano-phenoxy)-4-methyl-phenyl]-acetylamino}-3-methyl-benzenesulfonyl)-acetic acid | 513 (M + H)+ | 180.5-181.4 |
| I-153 | N-[4-(3-Amino-propionylsulfamoyl)-2-chloro-phenyl]-2-[4-chloro-3-(3-chloro-5-cyano-phenoxy)-2-fluoro-phenyl]-acetamide; compound with hydrochloric acid | 599 (M + H)+ | 199.3-199.6 |
| I-154 | N-[4-(2-Amino-ethanesulfonyl)-2-methyl-phenyl]-2-[3-(3-chloro-5-cyano-phenoxy)-4-methyl-phenyl]-acetamide | 498 (M + H)+ | 92.4-95.5 |
| I-155 | 2-[4-Chloro-3-(3-chloro-5-cyano-phenoxy)-2-fluoro-phenyl]-N-[2-chloro-4-(2-methoxy-acetylsulfamoyl)-phenyl]-acetamide; sodium salt | 598 (M − H)− | 151.7-152.3 |
| I-156 | 2-[4-Chloro-3-(3-chloro-5-cyano-phenoxy)-2-fluoro-phenyl]-N-[2-chloro-4-(2-hydroxy-acetylsulfamoyl)-phenyl]-acetamide; sodium salt | 584 (M − H)− | 178.0-179.5 |
| I-157 | 2-[3-(3-Chloro-5-cyano-phenoxy)-4-methyl-phenyl]-N-[4-(3-hydroxy-propane-1-sulfonyl)-2-methyl-phenyl]-acetamide | 513 (M + H)+ | 78.9-79.5 |
| I-158 | 2-[3-(3-Chloro-5-cyano-phenoxy)-4-methyl-phenyl]-N-[4-(1,1-dioxo-1$\lambda^6$-[1,2]thiazinan-2-yl)-2-methyl-phenyl]-acetamide | 522 (M − H)+ | 84.3-85.6 |
| I-159 | 2-[3-(3-Chloro-5-cyano-phenoxy)-4-methyl-phenyl]-N-{2-methyl-4-[2-(4-methyl-piperazin-1-yl)-acetyl]-phenyl}-acetamide | 531 (M + H)+ | 62.3-64.1 |
| I-160 | 2-[3-(3-Chloro-5-cyano-phenoxy)-4-methyl-phenyl]-N-[2-methyl-4-(1-oxo-1$\lambda^4$-thiomorpholin-4-yl)-phenyl]-acetamide | 508 (M + H)+ | 181.3-182.1 |

TABLE 1-continued

| Cpd. No. | NAME | MS | MP |
|---|---|---|---|
| I-161 | 2-[3-(3-Chloro-5-cyano-phenoxy)-4-methyl-phenyl]-N-[4-(1,1-dioxo-1λ$^6$-thiomorpholin-4-yl)-2-methyl-phenyl]-acetamide | 524 (M + H)$^+$ | 64.8-65.4 |
| I-162 | 2-[4-Chloro-3-(3-chloro-5-cyano-phenoxy)-2-fluoro-phenyl]-N-[2-chloro-4-(methyl-propionyl-sulfamoyl)-phenyl]-acetamide | 598 (M + H)$^+$ | 198.2-200.6 |
| I-163 | 2-[3-(3-Chloro-5-cyano-phenoxy)-4-methyl-phenyl]-N-[2-methyl-4-(2-morpholin-4-yl-acetyl)-phenyl]-acetamide; compound with trifluoro-acetic acid | 518 (M + H)$^+$ | 110.3-110.5 |
| I-164 | 2-[4-Chloro-3-(3-chloro-5-cyano-phenoxy)-2-fluoro-phenyl]-N-[2-chloro-4-(3-methoxy-propionylsulfamoyl)-phenyl]-acetamide; sodium salt | 614 (M + H)$^+$ | 133.1-140.7 |
| I-165 | 2-[4-Bromo-3-(3-cyano-5-difluoromethyl-phenoxy)-2-fluoro-phenyl]-N-(2-chloro-4-sulfamoyl-phenyl)-acetamide | 586 (M − H)$^−$ | 205.4-207.7 |
| I-166 | 2-[4-Chloro-3-(3-cyano-5-difluoromethoxy-phenoxy)-2-fluoro-phenyl]-N-(4-sulfamoyl-phenyl)-acetamide | 524 (M − H)$^−$ | |
| I-167 | 2-[4-Chloro-3-(3-cyano-5-difluoromethoxy-phenoxy)-2-fluoro-phenyl]-N-(2-chloro-4-sulfamoyl-phenyl)-acetamide | 558 (M − H)$^−$ | |
| I-168 | 2-[4-Chloro-3-(3-chloro-5-cyano-phenoxy)-2-fluoro-phenyl]-N-(2-chloro-4-methylsulfamoyl-phenyl)-acetamide | 540 (M − H)$^−$ | 199.1-200.0 |
| I-169 | 2-[4-Bromo-3-(3-cyano-5-difluoromethyl-phenoxy)-2-fluoro-phenyl]-N-(2-methyl-4-sulfamoyl-phenyl)-acetamide | 566 (M − H)$^−$ | 223.9-225.0 |
| I-170 | 2-[3-(3-Chloro-5-cyano-phenoxy)-4-methyl-phenyl]-N-[4-(1,1-dioxo-1λ$^6$-isothiazolidin-2-yl)-2-methyl-phenyl]-acetamide | 510 (M + H)$^+$ | 182.5-184.6 |
| I-171 | 2-[4-Chloro-3-(3-chloro-5-cyano-phenoxy)-2-fluoro-phenyl]-N-{2-chloro-4-[(2-methoxy-acetyl)-methyl-sulfamoyl]-phenyl}-acetamide | 614 (M + H)$^+$ | 183.2-185.5 |
| I-172 | 2-[4-Chloro-3-(3-chloro-5-cyano-phenoxy)-2-fluoro-phenyl]-N-{2-chloro-4-[(3-methoxy-propionyl)-methyl-sulfamoyl]-phenyl}-acetamide | 626 (M − H)$^−$ | 199.3-203 |
| I-173 | 2-[4-Chloro-3-(3-chloro-5-cyano-phenoxy)-2-fluoro-phenyl]-N-(2-chloro-4-pentanoylsulfamoyl-phenyl)-acetamide; sodium salt | 612 (M + H)$^+$ | 157.6-159.2 |
| I-174 | 2-[4-Chloro-3-(3-chloro-5-cyano-phenoxy)-2-fluoro-phenyl]-N-[2-chloro-4-(3-methyl-butyrylsulfamoyl)-phenyl]-acetamide; sodium salt | 610 (M − H)$^−$ | 159.3-163.4 |
| I-175 | 2-[4-Chloro-3-(3-chloro-5-cyano-phenoxy)-2-fluoro-phenyl]-N-[2-chloro-4-(2-diethylamino-acetylsulfamoyl)-phenyl]-acetamide; compound with hydrochloric acid | 641 (M + H)$^+$ | 195.3-197.2 |
| I-176 | 2-[4-Chloro-3-(3-chloro-5-cyano-phenoxy)-2-fluoro-phenyl]-N-[2-chloro-4-(4-methyl-pentanoylsulfamoyl)-phenyl]-acetamide; sodium salt | 626 (M + H)$^+$ | 195.6-197.0 |
| I-177 | 2-[4-Chloro-3-(3-chloro-5-cyano-phenoxy)-2-fluoro-phenyl]-N-[2-chloro-4-(2-morpholin-4-yl-acetylsulfamoyl)-phenyl]-acetamide; compound with hydrochloric acid | 655 (M + H)$^+$ | 223.3-225.0 |
| I-178 | N-(4-{2-[3-(3-Chloro-5-cyano-phenoxy)-4-methyl-phenyl]-acetylamino}-3-methyl-phenyl)-oxalamic acid ethyl ester | 506 (M + H)$^+$ | 182.5-183.9 |
| I-179 | N-(2-Chloro-4-sulfamoyl-phenyl)-2-[3-(3-cyano-5-difluoromethyl-phenoxy)-4-ethyl-2-fluoro-phenyl]-acetamide | | 239.6-240.7 |
| I-180 | 2-[3-(3-Cyano-5-difluoromethyl-phenoxy)-4-ethyl-2-fluoro-phenyl]-N-(2-methyl-4-sulfamoyl-phenyl)-acetamide | | 237.6-238.4 |
| I-181 | N-{4-[(3-Amino-propionyl)-methyl-sulfamoyl]-2-chloro-phenyl}-2-[4-chloro-3-(3-chloro-5-cyano-phenoxy)-2-fluoro-phenyl]-acetamide; compound with hydrochloric acid | 650 (M + H)$^+$ | >300 |
| I-182 | 2-[3-(3-Chloro-5-cyano-phenoxy)-4,5-dimethyl-phenyl]-N-(4-sulfamoyl-phenyl)-acetamide | 468 (M − H)$^−$ | 229.7-231.3 |
| I-183 | 2-[3-(3-Chloro-5-cyano-phenoxy)-4,5-dimethyl-phenyl]-N-(2-methyl-4-sulfamoyl-phenyl)-acetamide | 482 (M − H)$^−$ | 230.8-233.4 |
| I-184 | 2-[3-(3-Chloro-5-cyano-phenoxy)-4,5-dimethyl-phenyl]-N-(2-chloro-4-sulfamoyl-phenyl)-acetamide | 502 (M − H)$^−$ | 224.3-225.7 |

TABLE 1-continued

| Cpd. No. | NAME | MS | MP |
|---|---|---|---|
| I-185 | 2-[3-(3-Bromo-5-cyano-phenoxy)-4-chloro-2-fluoro-phenyl]-N-(2-methyl-4-sulfamoyl-phenyl)-acetamide | 552 (M − H)⁻ | 246.0-250.6 |
| I-186 | 2-{4-Chloro-3-[3-cyano-5-(3-hydroxy-prop-1-ynyl)phenoxy]-2-fluoro-phenyl}-N-(2-methyl-4-sulfamoyl-phenyl)-acetamide | 526 (M − H)⁻ | 170.1-173.2 |
| I-187 | 2-{4-Chloro-3-[3-cyano-5-(3-dimethylamino-prop-1-ynyl)-phenoxy]-2-fluoro-phenyl}-N-(2-methyl-4-sulfamoyl-phenyl)-acetamide | 555 (M + H)⁺ | 156.2-158.2 |
| I-188 | 4-(3-Chloro-4-{2-[4-chloro-3-(3-chloro-5-cyano-phenoxy)-2-fluoro-phenyl]-acetylamino}-benzenesulfonylamino)-4-oxo-butyric acid | | 143.4-144.0 |
| I-189 | 2-[4-Bromo-3-(3-chloro-5-cyano-phenoxy)-2-fluoro-phenyl]-N-(2-methyl-4-sulfamoyl-phenyl)-acetamide | 551 (M − H)⁻ | 244-245.1 |
| I-190 | 2-[3-(3-Chloro-5-cyano-phenoxy)-2-fluoro-4-methoxy-phenyl]-N-(2-chloro-4-sulfamoyl-phenyl)-acetamide | 522(100%), 534(60%) (M − H)⁻ | 212.0-212.8 |
| I-191 | 2-[3-(3-Chloro-5-cyano-phenoxy)-2-fluoro-4-methoxy-phenyl]-N-(2-methyl-4-sulfamoyl-phenyl)-acetamide | 502, 504(35%) (M − H)⁻ | 239.9-240.8 |
| I-192 | 2-[4-Chloro-3-(3-chloro-phenoxy)-phenyl]-N-phenyl-acetamide | 372 (M)⁺ | 126.8-127.7 |
| I-193 | 2-[3-(2-Bromo-5-chloro-phenoxy)-4-chloro-phenyl]-N-(4-sulfamoyl-phenyl)-acetamide | | 260.1-261.9 |
| I-194 | 2-[4-Chloro-3-(3,5-dicyano-phenoxy)-phenyl]-N-(2-pyrrol-1-yl-phenyl)-acetamide | 453 (M + H)⁺ | |
| I-195 | 2-[4-Chloro-3-(3,5-dicyano-phenoxy)-phenyl]-N-(2-fluoro-phenyl)-acetamide | 406 (M + H)⁺ | |
| I-196 | 2-[4-Chloro-3-(3,5-dicyano-phenoxy)-phenyl]-N-(2-methoxy-phenyl)-acetamide | 418 (M + H)⁺ | |
| I-197 | 2-[4-Chloro-3-(3,5-dicyano-phenoxy)-phenyl]-N-(2-isopropyl-phenyl)-acetamide | 430 (M + H)⁺ | |
| I-198 | 2-[4-Chloro-3-(3,5-dicyano-phenoxy)-phenyl]-N-o-tolyl-acetamide | 402 (M + H)⁺ | |
| I-199 | 2-[4-Chloro-3-(3,5-dicyano-phenoxy)-phenyl]-N-(2-ethyl-phenyl)-acetamide | 416 (M + H)⁺ | |
| I-200 | 2-[4-Chloro-3-(3,5-dicyano-phenoxy)-phenyl]-N-(2,3-dimethyl-phenyl)-acetamide | 416 (M + H)⁺ | |
| I-201 | 2-[4-Chloro-3-(3,5-dicyano-phenoxy)-phenyl]-N-(4-methoxy-2-methyl-phenyl)-acetamide | 432 (M + H)⁺ | |
| I-202 | 2-[4-Chloro-3-(3,5-dicyano-phenoxy)-phenyl]-N-(4-cyclohexyl-phenyl)-acetamide | 471 (M + H)⁺ | |
| I-203 | 2-[4-Chloro-3-(3,5-dicyano-phenoxy)-phenyl]-N-(2-cyano-phenyl)-acetamide | 413 (M + H)⁺ | |
| I-204 | 2-[4-Chloro-3-(3,5-dicyano-phenoxy)-phenyl]-N-(2-trifluoromethyl-phenyl)-acetamide | 456 (M + H)⁺ | |
| I-205 | 2-{2-[4-Chloro-3-(3,5-dicyano-phenoxy)-phenyl]-acetylamino}-4,5-dimethoxy-benzoic acid methyl ester | 506 (M + H)⁺ | |
| | I-206 is omitted | | |
| I-207 | 2-[3-(3-Chloro-5-cyano-phenoxy)-4-ethyl-phenyl]-N-phenyl-acetamide | 390 (M + H)⁺ | |
| I-208 | 2-[3-(2-Chloro-3,5-dicyano-phenoxy)-4-ethyl-phenyl]-N-phenyl-acetamide | 416 (M + H)⁺ | 189.3-192.3 |
| I-209 | 2-[4-Chloro-3-(2,5-dichloro-benzyl)-phenyl]-N-(2-chloro-4-sulfamoyl-phenyl)-acetamide | | 219.3-221.5 |
| I-210 | 2-[3-(3-Chloro-5-cyano-phenoxy)-4-methoxy-phenyl]-N-phenyl-acetamide | 393 (M + H)⁺ | 171.3-171.6 |
| I-211 | 2-[4-Chloro-3-(3,5-dicyano-phenoxy)-phenyl]-N-phenyl-acetamide | 386 (M − H)⁻ | 199.0-201.9 |
| I-212 | 2-[4-Chloro-3-(3,5-dicyano-phenoxy)-phenyl]-N-(4-methyl-3-sulfamoyl-phenyl)-acetamide | | |
| I-213 | 2-[4-Chloro-3-(3,5-dicyano-phenoxy)-phenyl]-N-(3-methanesulfonyl-phenyl)-acetamide | | |
| I-214 | (4-{2-[4-Chloro-3-(3,5-dicyano-phenoxy)-phenyl]-acetylamino}-phenoxy)-acetic acid methyl ester | | |
| I-215 | 3-(4-{2-[4-Chloro-3-(3,5-dicyano-phenoxy)-phenyl-acetylamino}-phenyl)-propionic acid methyl ester | | |
| I-216 | (4-{2-[4-Chloro-3-(3,5-dicyano-phenoxy)-phenyl]-acetylamino}-phenylsulfanyl)-acetic acid methyl ester | | |
| I-217 | 4-(4-{2-[4-Chloro-3-(3,5-dicyano-phenoxy)-phenyl]-acetylamino}-phenyl)-butyric acid methyl ester | | |

TABLE 1-continued

| Cpd. No. | NAME | MS | MP |
|---|---|---|---|
| I-218 | 2-[4-Chloro-3-(3,5-dicyano-phenoxy)-phenyl]-N-(2-fluoro-5-methanesulfonyl-phenyl)-acetamide | | |
| I-219 | (4-{2-[4-Chloro-3-(3,5-dicyano-phenoxy)-phenyl]-acetylamino}-phenyl)-acetic acid methyl ester | | |
| I-220 | 2-[4-Chloro-3-(3,5-dicyano-phenoxy)-phenyl]-N-(4-cyano-phenyl)-acetamide | | |
| I-221 | 4-{2-[4-Chloro-3-(3,5-dicyano-phenoxy)-phenyl]-acetylamino}-benzoic acid methyl ester | | |
| I-222 | 2-[4-Chloro-3-(3,5-dicyano-phenoxy)-phenyl]-N-(4-hydroxy-phenyl)-acetamide | | |
| | I-223 is omitted | | |
| I-224 | 2-[3-(3-Chloro-5-cyano-phenoxy)-4-methyl-phenyl]-N-(4-methyl-pyridin-3-yl)-acetamide | 392 (M + H)+ | 158.6-159.1 |
| I-225 | 2-[3-(3-Chloro-5-cyano-phenoxy)-4-methyl-phenyl]-N-(3-methyl-pyridin-2-yl)-acetamide | 392 (M + H)+ | 137.9-138.8 |
| I-226 | 2-[3-(3-Chloro-5-cyano-phenoxy)-4-methyl-phenyl]-N-(2,5-dimethyl-2H-pyrazol-3-yl)-acetamide | 395 (M + H)+ | 155.6-159.0 |
| I-227 | 2-[3-(3-Chloro-5-cyano-phenoxy)-4-methyl-phenyl]-N-(2-methyl-2H-pyrazol-3-yl)-acetamide | 381 (M + H)+ | 129.5-132.8 |
| I-228 | N-(6-Acetylamino-4-methyl-pyridin-3-yl)-2-[3-(3-chloro-5-cyano-phenoxy)-4-methyl-phenyl]-acetamide | 449 (M + H)+ | 222.5-224.0 |
| I-229 | 2-[3-(3-Chloro-5-cyano-phenoxy)-4-methyl-phenyl]-N-(6-methoxy-2-methyl-pyridin-3-yl)-acetamide | 422 (M + H)+ | 168.3-170.4 |
| I-230 | 2-[3-(3-Chloro-5-cyano-phenoxy)-4-methyl-phenyl]-N-(2-methyl-5-methylsulfanyl-2H-[1,2,4]triazol-3-yl)-acetamide | 428 (M + H)+ | 173-174 |
| I-231 | N-(2-Chloro-phenyl)-2-[3-(3,5-dichloro-benzoyl)-5-methyl-phenyl]-acetamide | 431 (M)+ | 142.0-146.2 |
| I-232 | 2-[3-(3,5-Dichloro-benzoyl)-5-methyl-phenyl]-N-(2-methyl-4-sulfamoyl-phenyl)-acetamide | 490 (M + H)+ | 247.1-249.0 |
| I-233 | 2-[4-Chloro-3-(4-cyano-6-methyl-pyridin-2-yloxy)-2-fluoro-phenyl]-N-(2-methyl-4-sulfamoyl-phenyl)-acetamide | 489 (M + H)+ | 230.1-230.7 |
| I-234 | (4-{2-[3-(3-Chloro-5-cyano-phenoxy)-4-methyl-phenyl]-acetylamino}-3-methyl-phenoxy)-acetic acid | 465 (M + H)+ | 174.8-176.4 |
| I-235 | (3-Chloro-4-{2-[3-(3-chloro-5-cyano-phenoxy)-4-methyl-phenyl]-acetylamino}-phenyl)-acetic acid methyl ester | 483 (M + H)+ | 116.9-118.0 |
| I-236 | (3-Chloro-4-{2-[3-(3-chloro-5-cyano-phenoxy)-4-methyl-phenyl]-acetylamino}-phenyl)-acetic acid | 468 (M)+ | 159.6-160.0 |
| I-237 | 2-[3-(3-Chloro-5-cyano-phenoxy)-4-methyl-phenyl]-N-(4-methanesulfonylamino-2-methyl-phenyl)-acetamide | 484 (M + H)+ | 180.0-181.4 |
| I-238 | 2-[3-(3-Chloro-5-cyano-phenoxy)-4-methyl-phenyl]-N-[4-(methanesulfonyl-methyl-amino)-2-methyl-phenyl]-acetamide | 498 (M + H)+ | 184.0-184.8 |
| I-239 | 4-{2-[4-Chloro-3-(3-chloro-5-cyano-phenoxy)-2-fluoro-phenyl]-acetylamino}-3-methyl-benzamide | 477 (M + H)+ | 255.9-257.1 |
| I-240 | 2-[7-(4-Chloro-benzoyl)-2,3-dihydro-benzofuran-5-yl]-N-(2-chloro-phenyl)-acetamide | | 141.1-144.9 |
| I-241 | 2-[7-(4-Chloro-benzoyl)-2,3-dihydro-benzofuran-5-yl]-N-(4-sulfamoyl-phenyl)-acetamide | | 259.0-261.0 |
| I-242 | 2-[4-Chloro-3-(3,5-dicyano-phenylsulfanyl)-phenyl]-N-(4-sulfamoyl-phenyl)-acetamide | | 247.9-250.9 |
| I-243 | 2-[3-(2-Bromo-5-chloro-phenylsulfanyl)-4-chloro-phenyl]-N-(4-sulfamoyl-phenyl)-acetamide | | 220-222.3 |
| I-244 | 2-[3-(2-Bromo-5-chloro-phenylsulfanyl)-4-chloro-phenyl]-N-(2-chloro-phenyl)-acetamide | | 172.2-172.8 |
| | I-245 and I-246 are omitted | | |
| I-247 | 2-[4-Chloro-3-(3,5-dichloro-benzoyl)-phenyl]-N-(2-chloro-phenyl)-acetamide | 451 (M)+ | 197.2-198.1 |
| I-248 | 2-[4-Chloro-3-(2,5-dichloro-benzoyl)-phenyl]-N-(2-chloro-phenyl)-acetamide | 451 (M)+ | 121.0-123.5 |
| I-249 | 2-[4-Chloro-3-(2,5-dichloro-benzoyl)-phenyl]-N-(2-methyl-4-sulfamoyl-phenyl)-acetamide | 510 (M)+ | 214.9-218.8 |
| I-250 | 2-[4-Chloro-3-(2,5-dichloro-benzoyl)-phenyl]-N-(4-sulfamoyl-phenyl)-acetamide | 496 (M)+ | 213.9-216.1 |
| I-251 | 2-[4-Chloro-3-(2,5-dichloro-benzoyl)-phenyl]-N-phenyl-acetamide | 417 (M)+ | 167.1-168.5 |
| I-252 | 2-[4-Chloro-3-(3,5-dichloro-benzoyl)-phenyl]-N-(2-methyl-4-sulfamoyl-phenyl)-acetamide | 510 (M)+ | 263-264.4 |

TABLE 1-continued

| Cpd. No. | NAME | MS | MP |
|---|---|---|---|
| I-253 | 2-[4-Chloro-3-(2,5-dichloro-benzoyl)-phenyl]-N-(2-chloro-4-sulfamoyl-phenyl)-acetamide | 530 (M)$^+$ | 197.0-199.6 |
| I-254 | 2-[3-(4-Chloro-benzoyl)-5-methyl-phenyl]-N-(4-sulfamoyl-phenyl)-acetamide | 442 (M)$^+$ | 260.9-263.3 |
| I-255 | 2-[3-(4-Chloro-benzoyl)-5-methyl-phenyl]-N-(2-methyl-4-sulfamoyl-phenyl)-acetamide | 465 (M)$^+$ | 205.8-208.0 |
| I-256 | 2-[3-(2-Chloro-benzoyl)-5-methyl-phenyl]-N-(2-methyl-4-sulfamoyl-phenyl)-acetamide | 456 (M)$^+$ | 207.7-209.3 |
| I-257 | 2-[3-(4-Chloro-benzoyl)-5-methyl-phenyl]-N-(2-chloro-4-sulfamoyl-phenyl)-acetamide | 476 (M + H)$^+$ | 218.9-220.7 |
| I-258 | 2-[3-(4-Chloro-benzoyl)-5-methyl-phenyl]-N-(2-chloro-phenyl)-acetamide | 397 (M)$^+$ | 134.7-135.5 |
| I-259 | 2-[3-(2-Chloro-benzoyl)-5-methyl-phenyl]-N-(2-chloro-phenyl)-acetamide | 397 (M)$^+$ | 125.1-127.0 |
| I-260 | 2-[3-(3-Chloro-benzoyl)-5-methyl-phenyl]-N-(2-methyl-4-sulfamoyl-phenyl)-acetamide | 456 (M)$^+$ | 210.3-211.6 |
| I-261 | 2-[3-(3-Chloro-benzoyl)-5-methyl-phenyl]-N-(4-sulfamoyl-phenyl)-acetamide | 442 (M)$^+$ | 211-213.1 |
| I-262 | 2-[3-(3-Chloro-benzoyl)-5-methyl-phenyl]-N-(2-chloro-phenyl)-acetamide | 397 (M)$^+$ | 113.0-113.8 |
| I-263 | 2-[3-(2-Chloro-benzoyl)-5-methyl-phenyl]-N-(4-sulfamoyl-phenyl)-acetamide | 442 (M)$^+$ | 165-167 |
| I-264 | 2-[3-(5-Bromo-2-chloro-benzoyl)-4-methoxy-phenyl]-N-(2-methyl-4-sulfamoyl-phenyl)-acetamide | 551 (M + H)+ | 177.0-177.9 |
| I-265 | 2-[3-(5-Cyano-2-methyl-benzoyl)-4-methyl-phenyl]-N-(2-methyl-4-sulfamoyl-phenyl)-acetamide | 462 (M + H)+ | 224.3-228.1 |
| I-266 | 2-[3-(5-Cyano-2-methyl-benzoyl)-4-methyl-phenyl]-N-(4-sulfamoyl-phenyl)-acetamide | 448 (M + H)+ | 229.6-231.1 |
| I-267 | N-(2-Chloro-phenyl)-2-[3-(5-cyano-2-methyl-benzoyl)-4-methyl-phenyl]-acetamide | 403 (M + H)+ | 129.4-131.6 |
| I-268 | 2-[3-(5-Cyano-2-ethyl-benzoyl)-4-ethyl-phenyl]-N-(2-methyl-4-sulfamoyl-phenyl)-acetamide | 490 (M + H)+ | |
| I-269 | 2-[3-(3,5-Dichloro-benzoyl)-5-methyl-phenyl]-N-(4-sulfamoyl-phenyl)-acetamide | 476 (M)$^+$ | 226.0-227.9 |
| I-270 | 2-[3-(3-Chloro-5-cyano-phenoxy)-2-fluoro-4-methyl-phenyl]-N-(2-chloro-4-propionylsulfamoyl-phenyl)-acetamide; sodium salt | 564 (M + H)+ | 158.8-162 |

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser 's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

N-Phenyl 3-phenoxy-phenylacetamide compounds are prepared from phenyl acetic acid derivatives 4 ($X^1$=O, $R^5$=optionally substituted phenyl) as depicted in Scheme 1. The preparation of phenylacetic acids related to the present compounds has been described in U.S. Ser. Nos. 10/807,993 and 10/807,766 entitled *Non-nucleoside Reverse Transcriptase Inhibitors* filed Mar. 23, 2004 These applications are hereby incorporated by reference in their entirety.

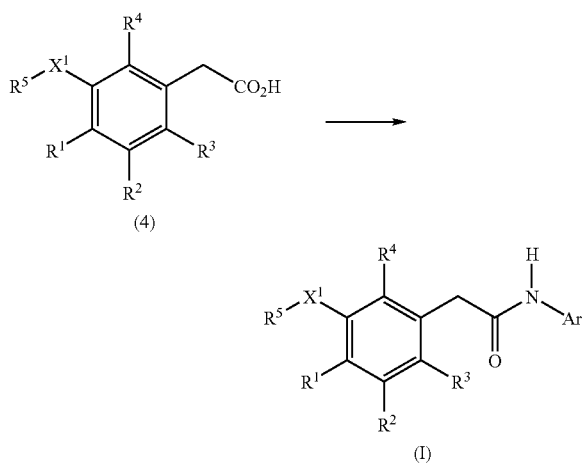

4-Alkyl-3-aryloxy-phenylacetic acid compounds are useful precursors to some embodiments of the present invention and can be prepared from 4-hydroxy-3-methoxyphenyl acetate by Pd catalyzed coupling of a dialkyl zinc species and ethyl 3-methoxy-4-trifluorosulfonyloxy-phenylacetate (4b) derived therefrom to produce the corresponding 4-alkyl compound (SCHEME 1). The Negishi coupling of organozinc halides or dialkylzinc with haloarenes and aryl triflates is an effective means for attachment of an alkyl group to an arene (E.-I. Negishi, *Acc. Chem. Res.* 1982 15:340-348). The reaction is catalyzed by palladium Pd(0) and palladium is prefer- ably ligated to a bidentate ligand including Pd(dppf)Cl$_2$ and Pd(dppe)Cl$_2$. (J. M. Herbert *Tetrahedron Lett.* 2004 45:817-819) Typically the reaction is run in an inert aprotic solvent and common ethereal solvents include dioxane, DME and THF are suitable. The reaction is commonly run at elevated temperature.

Alternatively Friedel-Crafts acylation of ethyl 3-methoxy-phenylacetate affords 4-acetyl-3-methoxy-phenylacetate 8. Reduction of the ketone to afford the 4-ethyl derivative 12a can be accomplished under a variety of conditions including triethylsilylhydride/TFA, catalytic hydrogenation and hydrogenolysis, Clemmenson and Wolf-Kischner procedures. Alternatively the side chain can be further elaborated by subjecting the ketone to a Wittig condensation and reduction of the resulting olefin. In the present invention triphenylphosphonium methylide is condensed with 8 affording ethyl 4-iso-propenyl-3-methoxy-phenylacetate (14) which was reduced to the corresponding ethyl 4-iso-propyl-3-methoxy-phenylacetate (16). One skilled in the art will recognize many closely related alternative procedures are available that afford other 4-alkyl substituents. Demethylation of the methyl ether affords the corresponding ethyl 4-alkyl-3-hydroxyphenylacetate 18a which are useful synthetic intermediates for introduction of the 3-aryloxy moiety.

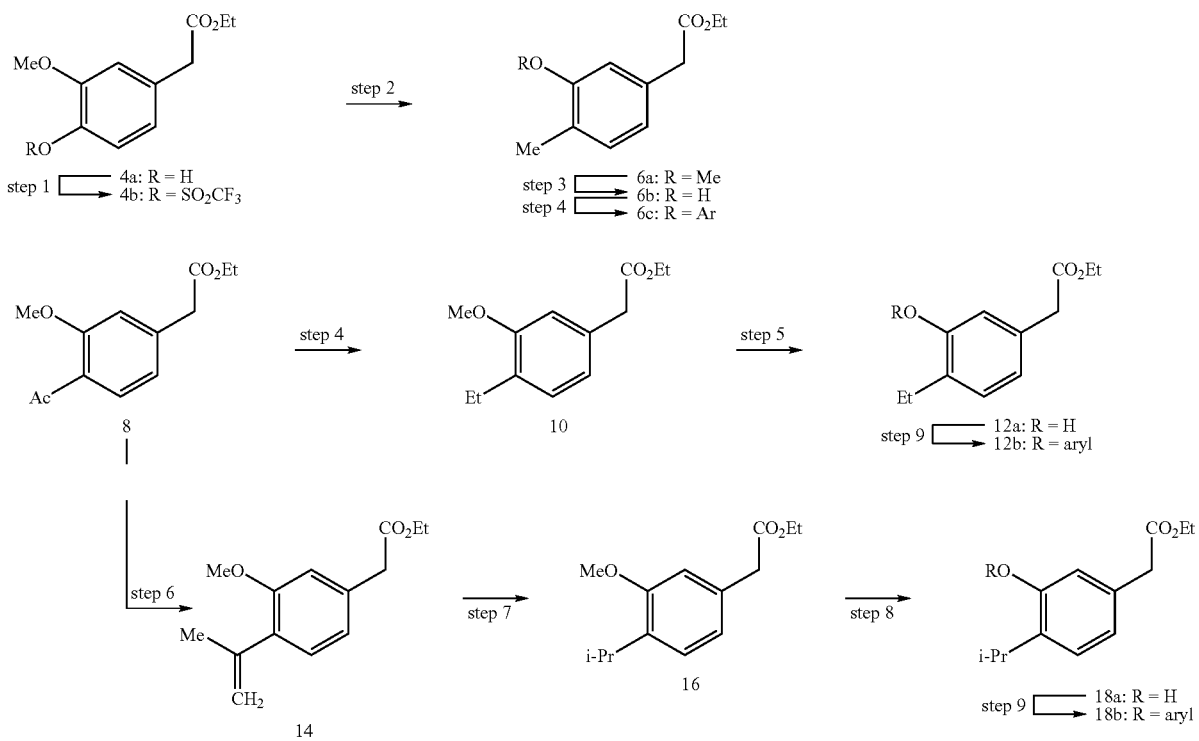

3,4-Dimethyl-5-aryloxy-phenylacetic acid compounds were also prepared using a dialkylzinc mediated coupling; however, prior to that coupling the activating effect of the hydroxyl was exploited to formylate the aromatic ring and afford 22a. Reduction of the formyl substituent provides the methylated compound 22c. (SCHEME 2) Demethylation of the methyl ether affords the phenol 24c which can be used to introduce the biaryl ether linkage.

SCHEME 2

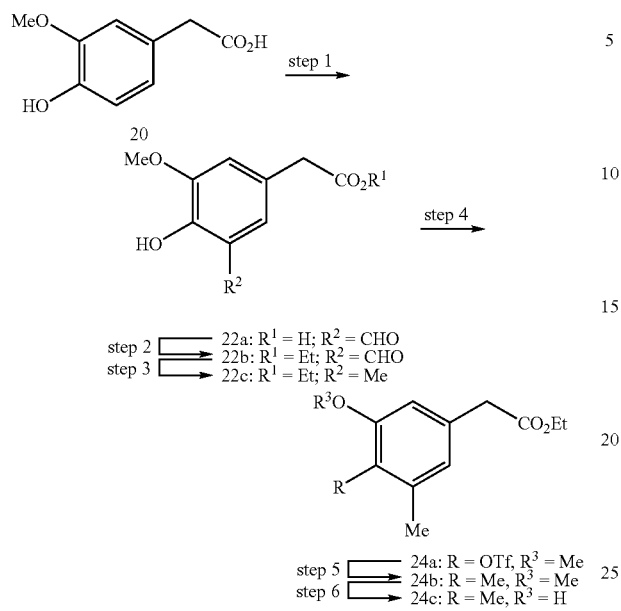

SCHEME 3

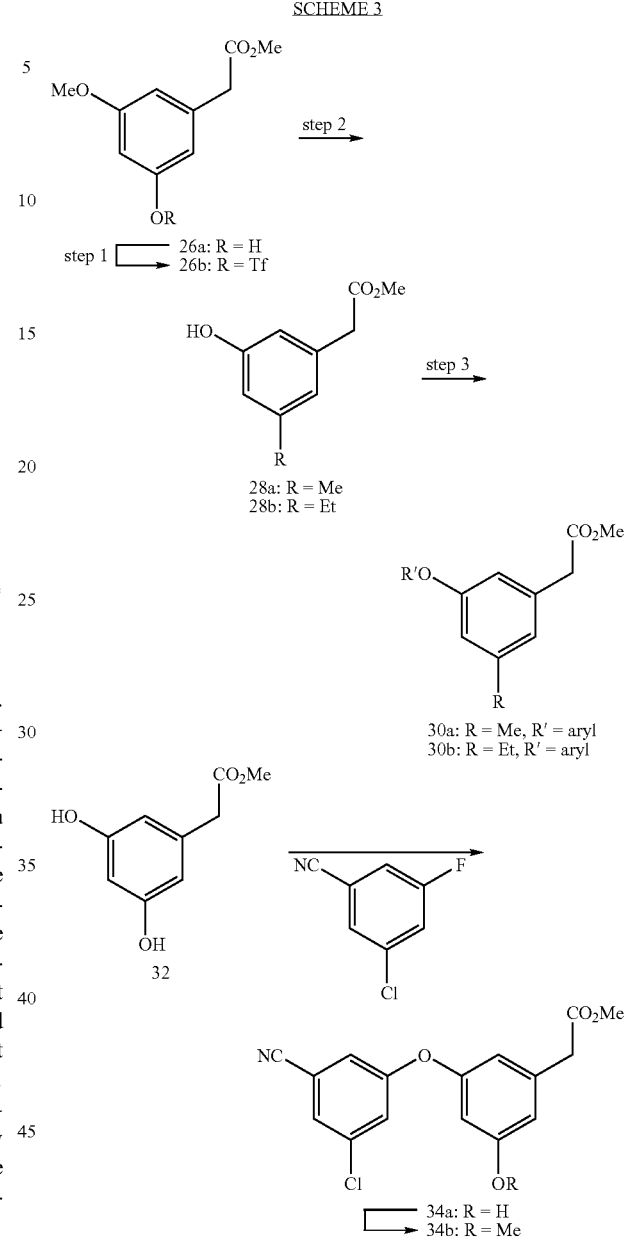

The preparation of diaryl ethers has been reviewed (J. S. Sawyer, *Recent Advances in Diaryl Ether Synthesis, Tetrahedron* 2000 56:5045-5065). Introduction of the (hetero)aryloxy ether can often be accomplished by direct $S_NAR$ displacement reaction on a aromatic ring substituted with a leaving group and electronegative substituents. Fluoroaromatic compounds with electronegative substituents are known to be sensitive to nucleophilic attack by soft nucleophiles. Fluorine substituents are generally significantly more labile than other halogen substituents. While hard nucleophiles like water and hydroxide fail to displace fluoride, soft nucleophiles like phenols, imidazoles, amines, thiols and some amides undergo facile displacement reactions even at room temperature (D. Boger et al., *Biorg. Med. Chem. Lett.* 2000 10:1471-75; F. Terrier *Nucleophilic Aromatic Displacement: The Influence of the Nitro Group* VCH Publishers, New York, N.Y. 1991). Phenols typified by 6b and 12a can be treated with appropriately substituted aryl fluorine compounds to produce diaryl ethers (infra).

Aryl ethers also can be efficiently prepared by $Cu(OAc)_2$ catalyzed condensation of substituted benzene boronic acids and phenols (D. A. Evans et al., *Tetrahedron Lett.,* 1998 39:2937-2940 and D. M. T. Chan et al., *Tetrahedron Lett.* 1998 39:2933-2936). This protocol can also be adapted to phenols such as 6b and 12a. Benzene boronic acids with a variety of other substituention are widely available.

Alternatively, variations of the Ullmann diaryl ether synthesis with Cu(I) salts (J.-F. Marcoux et al., *J. Am. Chem. Soc.* 1997 119:10539-540; E. Buck et al, *Org. Lett.* 2002 4(9): 1623-1626) or palladium-catalyzed coupling procedures also has been reported (G. Mann et al., *J. Am. Chem. Soc.,* 1999 121:3224-3225) have been described. One skilled in the art will appreciate that optimal procedure will vary depending on the nature and position of substituents on the aryl rings to be coupled and useful conditions for the coupling can by identified without undue experimentation.

5-Methyl- and 5-ethyl-3-hydroxy-phenylacetic derivatives were prepared by monomethylation of 3,5-dihydroxy-phenylacetic acid to afford 26a followed by sequential treatment with triflic anhydride and dialkylzinc/$Pd[P(Ph)_3]_4$ to afford 28a and 28b. While the reactions are illustrated with methyl and ethyl groups, one skilled in the art will appreciate that a variety of substitutents can be introduced depending on the reagent selected. Demethylation of the methyl ether was accomplished as previously described to afford phenols that can be used to introduce diaryl ethers. 3-Aryloxy-5-methoxy-phenylacetic acids compounds can be prepared by monoarylation of alkyl 3,5-dihydroxy-phenylacetates and subsequent methylation to afford 34b (SCHEME 3). Other alkoxy compounds are readily prepared by replacing methyl iodide with other alkylating agents.

SCHEME 4

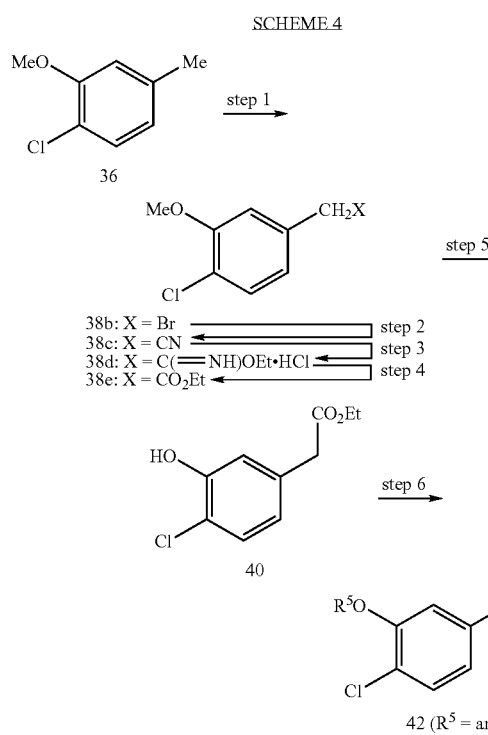

When substituted phenylacetic acid precursors are unavailable, an alternative route utilizing methyl substituents to elaborate the acetic acid side chain has been used. Ethyl 4-chloro-3-hydroxy-phenylacetate (40) was prepared from 1-chloro-2-methoxy-4-methyl-benzene by benzylic bromination (step 1) and displacement of the bromine atom with sodium cyanide (step 2). Hydrolysis of the nitrile (steps 3 and 4) and demethylation of the ether under standard conditions afforded 40. $BBr_3$ or LiI/syn-collidine mediated demethylations are effective techniques for conversion of methyl ethers to the corresponding phenols. Incorporation of the aryl or heteroaryl ether is achieved by one of the methods described previously.

4-Chloro-2-fluoro-3-phenoxy-phenylacetic acid compounds (SCHEME 5) can prepared by starting from 1-chloro-3-fluoro-2-methoxy4-methylbenzene utilizing a sequence comprising benzylic bromination with NBS and AIBN, cyanide displacement, hydrolysis of the nitrile and esterification of the carboxylic acid analogous to that described in SCHEME 4

SCHEME 5

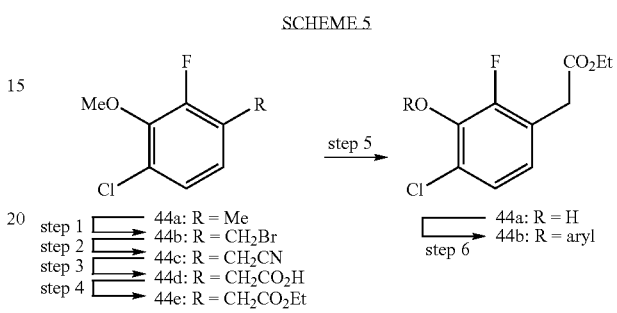

Alternatively, the synthesis of 2-fluoro substituted compounds was accomplished by exploiting the facile displacement of fluoroaromatic compounds. Thus, treatment of 1,2,3-trifluoro-4-nitro-benzene (46) with an alkali metal phenolate results in displacement of the 3-fluoro group with good regioselectivity to afford 48a (SCHEME 6). Treatment of 48a with carbanion formed by deprotonation of tert-butyl ethyl malonate resulted in the regioselective introduction of a malonic ester (48b) which is subjected to acid-catalyzed hydrolysis of the tert-butyl ester and decarboxylation to afford 48c. After introduction of the phenoxy and acetic acid moieties, the nitro group is readily converted to other substituents at the 4-position. Reduction of the nitro substituent afforded 50a which can be subjected to Sandmeyer conditions to introduce a bromo 50a or chloro 50e substituent. The bromo substituent could be further reacted with a dialkyl zinc (the Negishi Reaction) to afford 4-alkyl-3-aryloxy-2-fluoro-phenylacetic acid compounds exemplified by 50c and 50d.

SCHEME 6

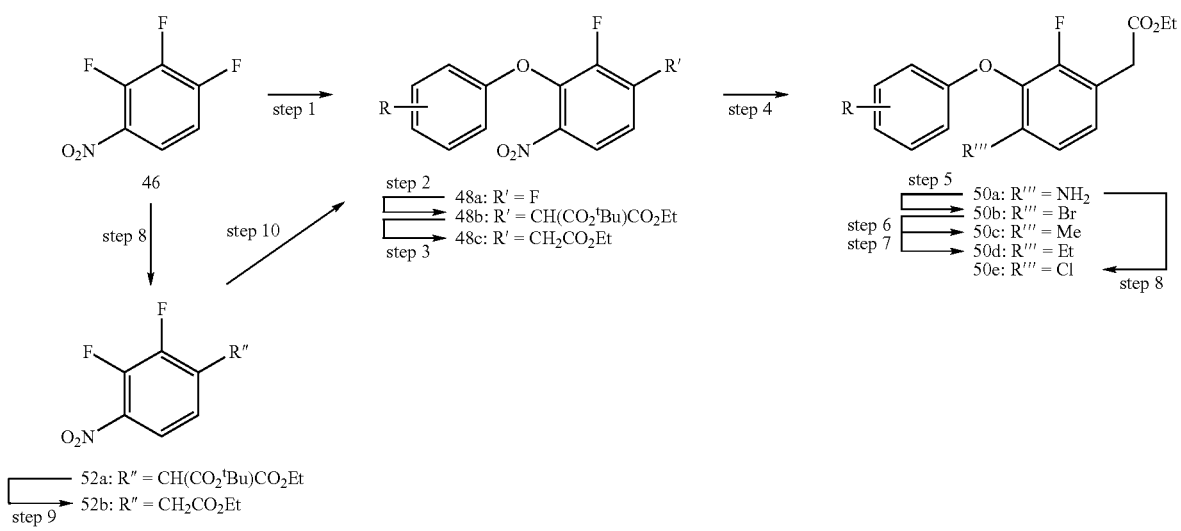

Alternatively, the reaction of the mixed tert-butyl ethyl ester of malonic acid affords a regioisomeric mixture of adducts in which displacement of the fluorine at the 1-position 52a predominates in a 2:1 ratio and the isomers are separated by $SiO_2$ chromatography. Hydrolysis and decarboxylation of 52a affords the phenylacetic acid 52b which is an effective substrate for introduction of an aryl ether and Sandmeyer-type chemistry.

4-Alkoxy-2-fluoro-3-phenoxyphenylacetic acid compounds were prepared from o-difluorobenzene. A mixture ortho-difluorobenzene (54a) and trimethylsilylchloride was treated with butyl lithium to produce 2,3-difluoro-1,4-bis-trimethylsilanyl-benzene (54b) which was brominated to afford 54c. Selective monometallation of 54c with iso-propylmagnesium chloride-lithium chloride complex and quenching the organomagnesium compound with DMF afforded 54d. Reaction of 54d with a phenol in the presence of $K_2CO_3$ resulted in displacement of the fluorine atom adjacent to the aldehyde to afford 56a. The aldehyde was subjected to a Baeyer-Villiger oxidation with trifluoroperacetic acid which underwent concomitant hydrolysis to the phenol 56b which was alkylated with $Cs_2CO_3$ and methyl iodide to afford the methoxy substituted analog 56c. Metallation of the remaining bromine substituent with iso-PrMgCl/LiI/THF and allylation of the resulting Grignard reagent afforded 58a which was oxidatively cleaved with $NaIO_4$/Ru(III)$Cl_3$ to produce the phenylacetic acid 58b.

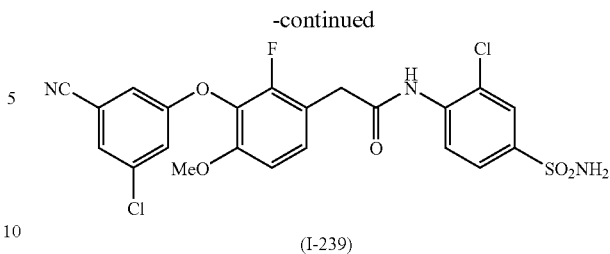

(I-239)

The substituted phenylacetic acid esters thus obtained were converted to the corresponding amides through a three-step sequence including hydrolysis of the ester, conversion of the resulting acid to an acid chloride and condensation of the acid chloride with an aryl amine or heteroarylamine.

Fluorine-substituted aromatic compounds which are useful intermediates for formation of the biaryl ether are commercially available or readily prepared from commercially available precursors. 3-Chloro-5-fluoro-benzonitrile (59a), 1-bromo-3-chloro-5-fluorobenzene, 1-bromo-2-fluoro4-chloro-benzene, 4-chloro-3-fluorobenzonitrile, 3-fluoro-5-trifluoromethyl-benzonitrile (59b), 3,5-dibromo-fluoro-benzene, 1,3-dichloro-2-fluorobenzene (59c), 1,4-dichloro-2-fluoro-6-bromo-benzene (59d), 1-chloro-2-fluoro4,6-dibromo-benzene (59e) and 1-chloro-2,6-difluoro4-bromo-benzene (59f) were purchased. Cyanide substituents can be introduced into a aromatic ring by $Zn(CN)_2$/palladium-catalyzed displacement of a halogen by cyanide which can be carried out either after introduction of the biaryl ether or on a halogenated precursor (SCHEME 8-reaction B) prior to formation of the ether.

SCHEME 7

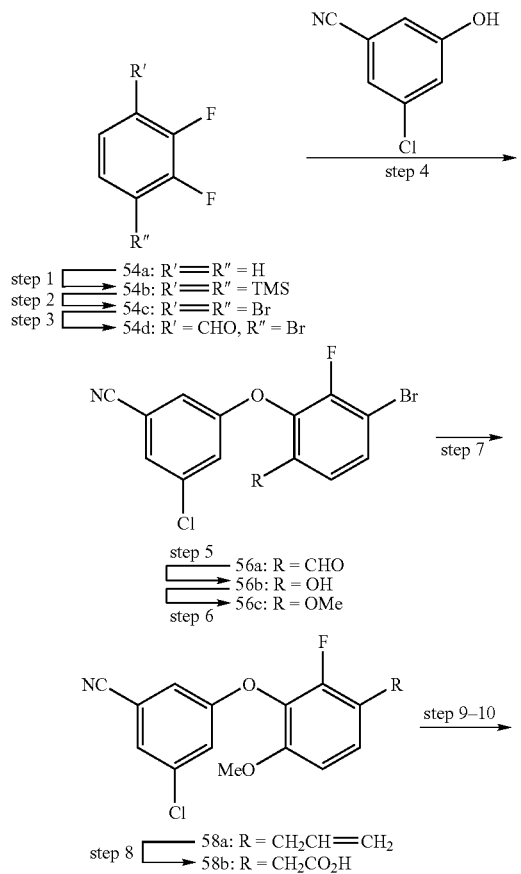

SCHEME 8

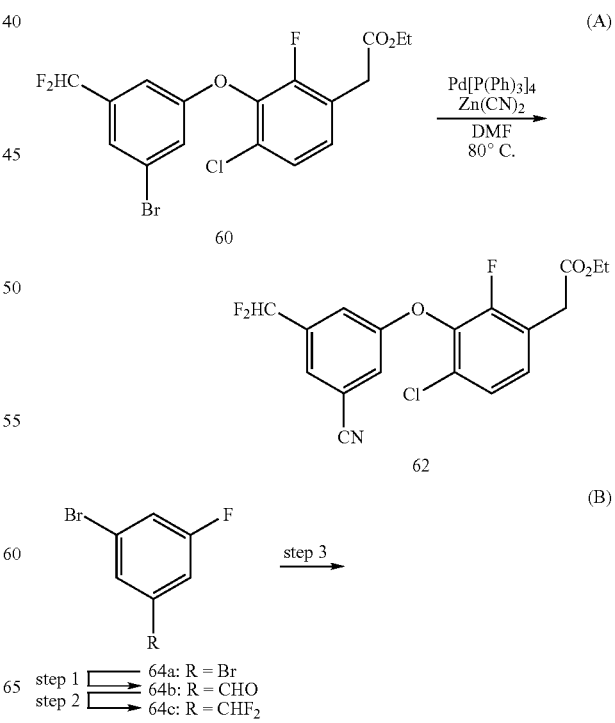

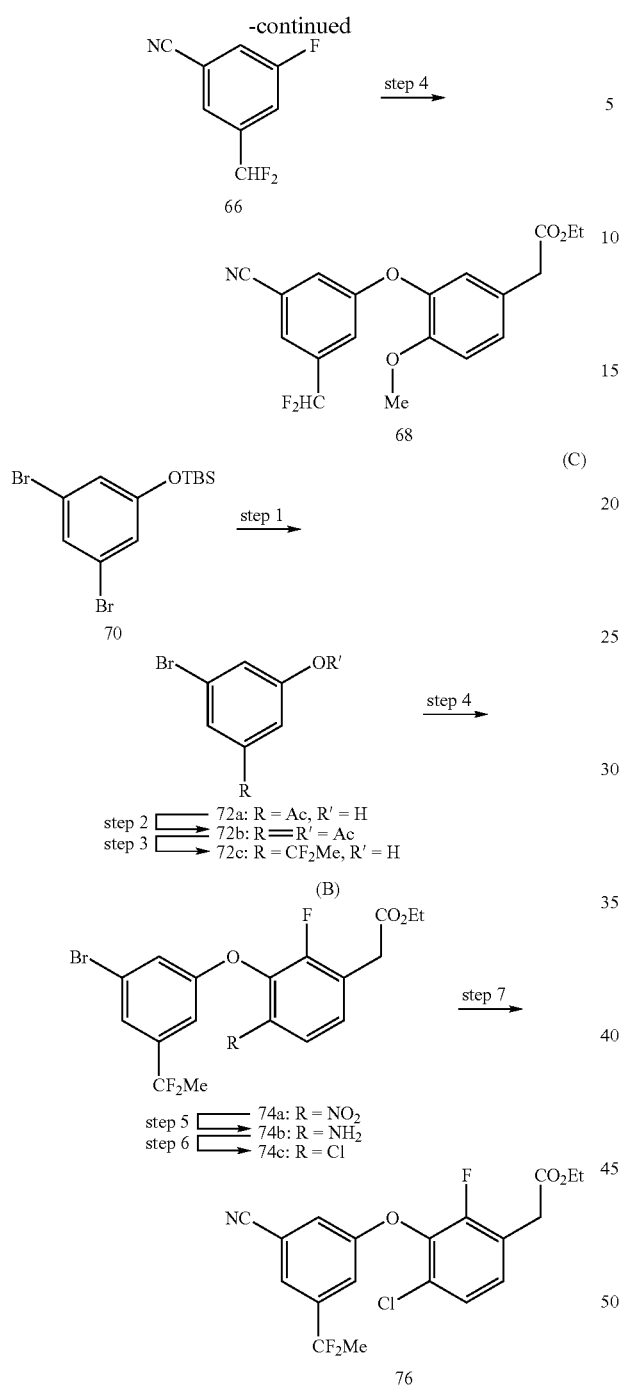

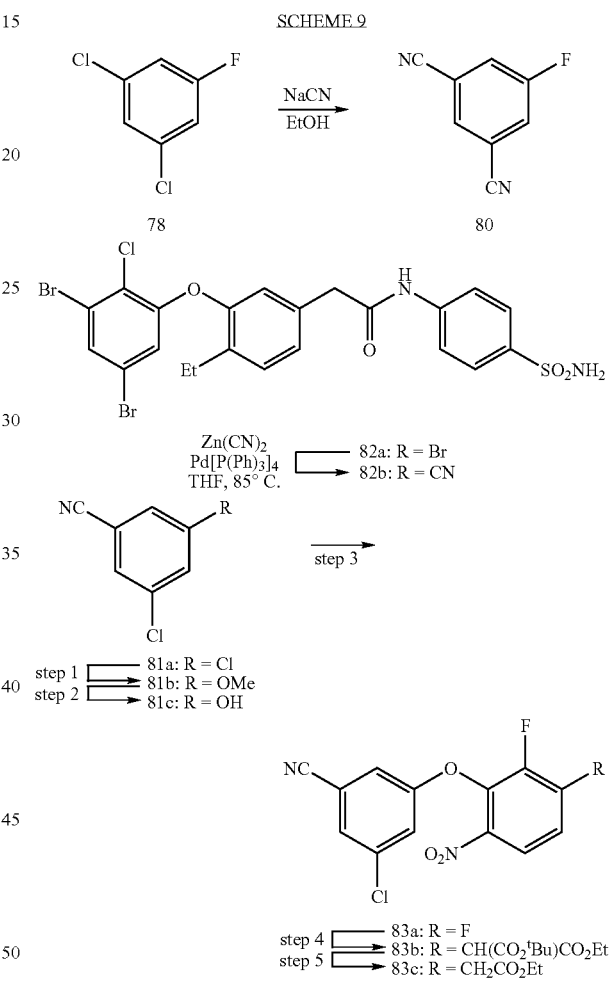

Fluoroalkyl substituted compounds are useful embodiments of the invention and 66 and 72c were prepared by fluorination of a carbonyl compound with a fluorinating agent such as (diethylamino)sulfur trifluoride (DAST) or [bis(2-methoxyethylamino)sulfur difluoride (DEOXO-FLUOR®). Thus 1,3-dibromo-5-fluorobenzene (64a) was mono-metallated and formylated to afford 64b. Fluorination of 64b with DAST afforded 64c which was optionally treated with $Zn(CN)_2$ and $Pd[P(Ph)_3]_4$ to introduce a nitrile prior to formation of the bis-aryl ether 68 by condensation of 66 and 52b. The 1,1,-difluoroethyl substituent was introduced utilizing an analogous strategy whereby an acetyl derivative was fluorinated with DEOXO-FLUORO®. The acetyl compound 72b was obtained by mono-metallation of 70 and quenching with N-methyl-N-(methoxy)acetamide. The fully elaborated phenylacetic acid 74 was obtained by condensation of 72c and 52b followed by a Sandmeyer reaction in the presence of Cu(I)Cl and HCl. Optional introduction of a cyanide into the aryl ring (step 7) was carried out as described previously.

Di-cyano substitution is a feature of some embodiments of the present invention and dicyano aromatic compounds, e.g. 80 are readily available by bis-cyanation of a dihalo precursor 78. One skilled in the art will appreciate this transformation can be carried out on a variety of dihalogenated substrates. Considerable flexibility in the sequence of the transformations is possible and bis-cyanation can be carried out either prior to or after formation of the biaryl ether, e.g., transformation of 82a to 82b.

In some examples of the present invention the biaryl ether is introduced by reacting a suitably substituted phenol and a fluoro-substituted phenylacetic acid or precursor thereof. (see SCHEME 6) Many useful phenols are commercially available. 3-Chloro-5-hydroxy-benzonitrile (81c) was a useful intermediate in the synthesis of some embodiments of the present invention. 81c was prepared from 3,5-dichlorobenzonitrile (81a) by displacement of one chlorine substituent with sodium methoxide and LiI/collidine mediated demethylation of the resulting arylmethyl ether 81b. The phenol was reacted with 46 to afford 83a which was further transformed to 83c as described previously.

Introduction of haloalkoxy substituents were readily accomplished by insertion of a dihalocarbene into to a phenol. 3,5-Dihydroxy-benzonitrile (84a) is transformed into the base-stable mono SEM-ether 84c which is reacted with difluorocarbene generated by decarboxylative elimination of

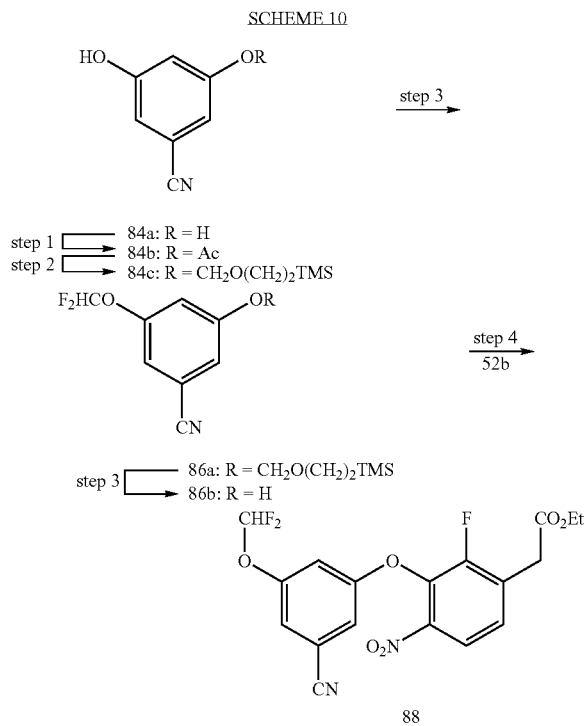

difluorochloroacetic acid (SCHEME 10). Deprotection and condensation of the resulting phenol 86b with ethyl 2,3-difluoro4-nitro-phenylacetate (52b) affords 88 which can be further converted to compounds of the present invention.

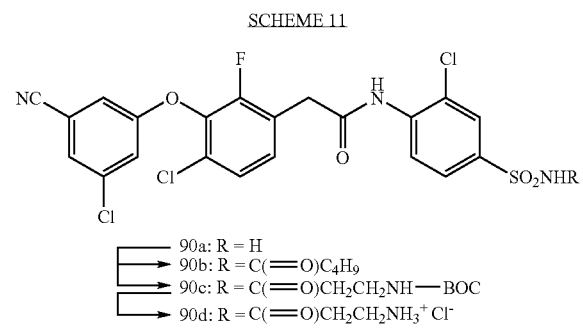

Other embodiments of the invention include N-acylsulfonamides (SCHEME 11) which can be prepared by acylation of the corresponding sulfonamide. The acylation can be achieved by reacting the sulfonamide with acyl halides or anhydrides, e.g. propionyl anhydride, or, in the case of acylation with N-protected amino acids, by transient activation of the carboxylic acid followed by condensation with 90a and deprotection. Protocols for activation, coupling and deprotection of amino acids are well known in the art. Although the acyl sulfonamides in SCHEME 11 are depicted as neutral molecules, the acidic proton on the acyl sulfonamide nitrogen can be readily deprotonated to form salts. Embodiments formed from α-amino acids can be deprotected utilizing well established procedures and the free amino group can be converted to acid addition salts.

Other N-substituted sulfonamides were prepared by amidation with a 4-amino-benzensulfonyl fluoride (95) to afford an intermediate sulfonyl fluoride 114 which is further reacted with a (di)alkylamine to afford the desired sulfonamide derivatives.

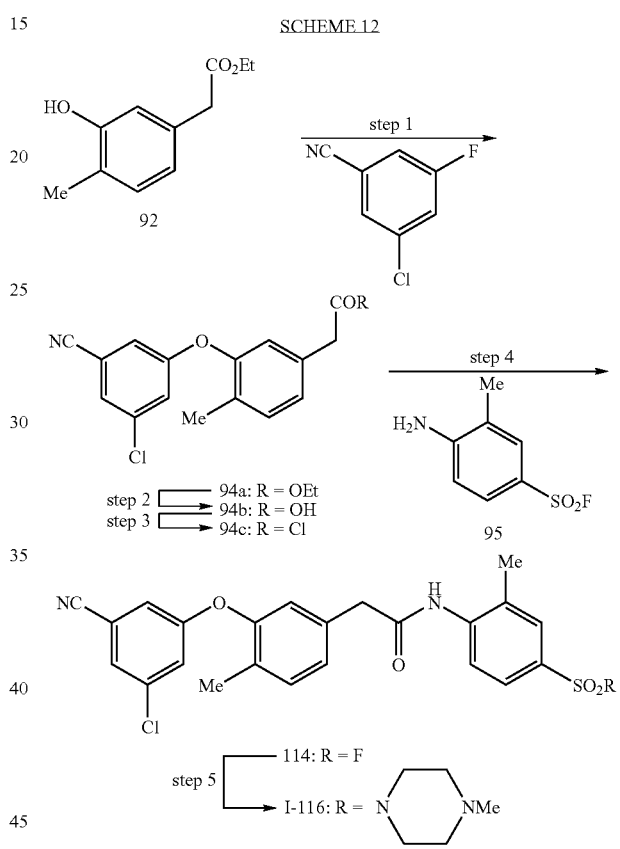

4-Amino-benzene-sulfones are useful intermediates for the synthesis of some embodiments of the present invention (SCHEME 13). The requisite anilines were prepared from 4-fluoro-2-methylnitrobenzene. Displacement of the fluoride with sodium sulfide and alkylation of the nucleophilic thiol with ethyl bromoacetamide and oxidation of the thiol to the corresponding sulfone with MCPBA affords 98d. Reduction of the nitro substituent and condensation of the resulting amine 100 with an aroyl chloride affords 122. Subsequent modification of the function groups, e.g., hydrolysis of the carboxylic acid ester is possible using previously described methodology. Other alkylating agents useful to prepare compounds of the present invention include haloalkanols, e.g. bromoethanol and brompropanol, N-protected halo amines, e.g., (2-bromo-ethyl)-carbamic acid tert-butyl ester and bromoacetonitrile. The corresponding ether analogs were available by alkylation of the analogous phenols. (see, e.g., P. G. Wyatt et al. *J. Med. Chem.* 1995 38(10):1657-1665).

SCHEME 13

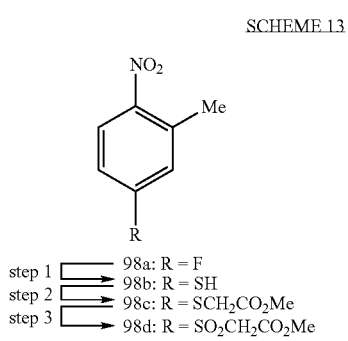

step 1: 98a: R = F
step 2: 98b: R = SH
step 3: 98c: R = SCH$_2$CO$_2$Me
        98d: R = SO$_2$CH$_2$CO$_2$Me

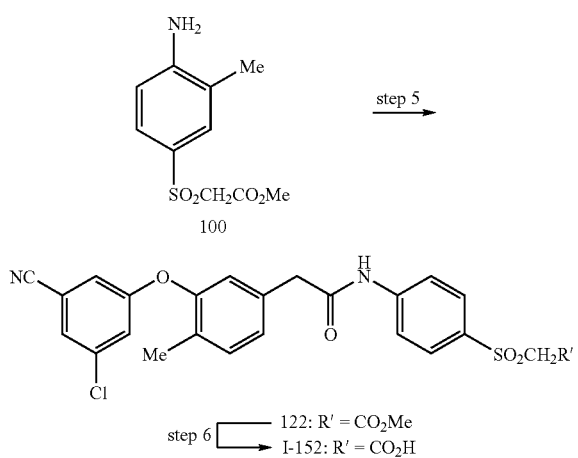

100 step 6: 122: R' = CO$_2$Me
        I-152: R' = CO$_2$H (7-Aryloxy-benzoftiran-5-yl)-acetic acid derivatives were prepared from (2,3-dihydro-benzofuran-5-yl)-acetic acid ethyl ester (101a). Introduction of the oxygen substituent was achieved by Friedel-Craft acetylation and subsequent Baeyer-Villiger rearrangement and hydrolysis of the acetate to afford 101d. Introduction of the aryloxy moiety is accomplished by S$_N$AR displacement of an aryl halide or by Cu(OAc)$_2$ catalyzed condensation of substituted benzene boronic acids and phenols as described previously. Oxidation of the dihydrofliran by allylic bromination which spontaneously underwent dehydrobromination. afforded 105a.

SCHEME 14

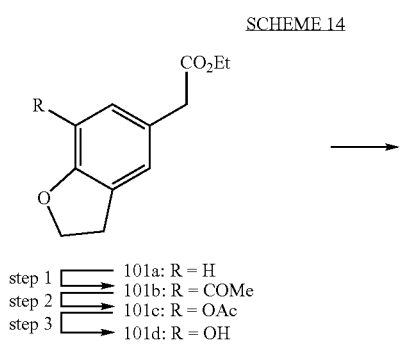

step 1: 101a: R = H
step 2: 101b: R = COMe
step 3: 101c: R = OAc
        101d: R = OH

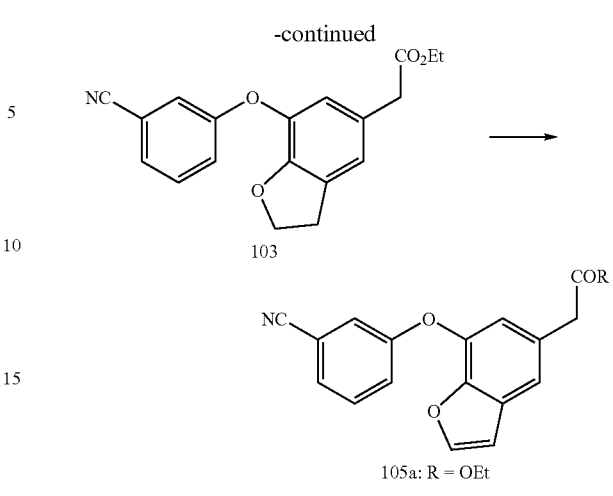

103

105a: R = OEt

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuiric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. N-acylsulfonamides have an acidic proton which can be abstracted to form a salt with an organic or inorganic cation. Other compounds of the invention have a basic nitrogen which can from acid addition salts.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another nonnucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLE 1

2-[4-Chloro-3-(3-chloro-5-cyano-phenoxy)-phenyl]-N-(4-sulfamoyl-phenyl)-acetamide (I-1)

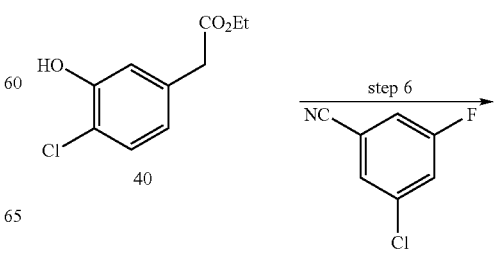

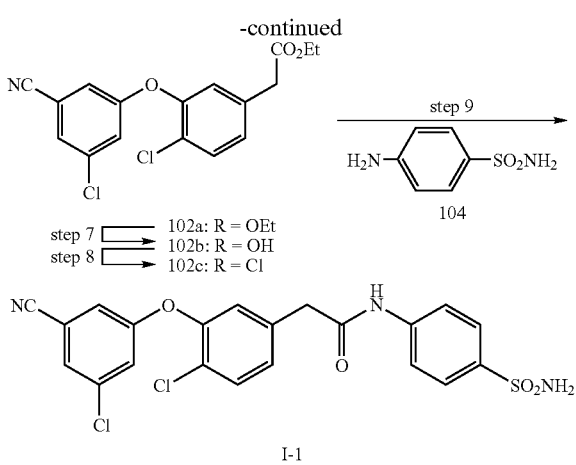

step 1—A solution of 4-chloro-3-methoxytoluene (36; 0.5 g; 3.2 mmol), NBS (0.57 g; 3.2 mmol) and benzoyl peroxide (0.031 g; 0.13 mmol) and 32 mL of DCE were heated at reflux for 3 h. The reaction mixture was cooled, diluted with CH₂Cl₂ and washed with water and brine. The organic extract was dried, filtered and evaporated to yield the bromomethyl compound 38b which was used without further purification.

step 2—The 28 g (0.166 mmol) of 38b from the previous step, NaCN (28 g; 0.58 mmol; 3.5 equiv.) and 500 mL of 90% aqueous EtOH were stirred at room temperature overnight. The crude residue was partitioned between EtOAc/H₂O (359 mL of each), washed with brine, dried, filtered and evaporated. The crude product was purified by SiO₂ chromatography eluting with a EtOAc/hexane gradient (100% hexane to 90%hexane) to afford 21 g of 38c.

step 3—Gaseous HCl was slowly bubbled into a cooled solution of 4-chloro-3-methoxyacetonitrile (38c) in toluene (10mL), ether (10 mL) and EtOH (1 mL) for about 10 min. The reaction was stopped and stored at −30° C. for one week. TLC failed to detect any remaining starting material. The solvent was evaporated and the yellow solid was stirred with Et₂O, filtered and washed with Et₂O and dried in a vacuum oven to yield 0.57 g (90%) of ethyl 4-chloro-3-methoxyphenylmethylimidate (38d).

step 4—A solution of 0.57 g of 38d and 10 mL of H₂O was heated at 40° C. for 3 h. The reaction was cooled to RT and extracted with EtOAc. The reaction was dried (MgSO4), filtered and evaporated and the resulting product 38e was used without further purification.

step 5—A solution of ethyl 4-chloro-3-methoxyphenyllactate (38e; 36 g; 157 mmol) and DCM (2 L) was cooled to −78° C. and a solution of BBr₃ (74 mL; 785 mmol; 1.0 M in CH₂Cl₂) was added over 30 min. After 1 h at −78° C. the reaction was allowed to warm to RT. When starting material was consumed the reaction was cooled in an ice-water bath and the reaction quenched with 200 mL of water. The aqueous phase was extracted with CH₂Cl₂:EtOAc (4:1 v/v). The combined extracts were washed with water and brine, dried (Na₂SO₄), filtered and evaporated to afford 30 g (90%) of 40.

step 6—A solution of 40 (1.07 g, 5 mmol), 3,5-dichlorobenzonitrile (1.3 g, 7.56 mmol), K₂CO₃ (2.07 g, 15.0 mmol) and NMP (10 mL) was stirred and heated to 110 ° C. for 6 h. The reaction was cooled to RT and diluted with H₂O (50 mL) and twice extracted with EtOAc. The combined organic extracts were washed sequentially with water and brine, dried (Na₂SO₄), filtered and concentrated in vacuo.

The crude product was purified by SiO₂ chromatography eluting with EtOAc/hexane (10:90) to afford 0.328 g of 102a.

step 7—To a solution of 102a (0.80 g; 0.1.98 mmol) and LiOH (142.5 mg, 5.94 mmol) dissolved in EtOH (8 mL) and water (2 mL) and stirred for at RT. The mixture was concentrated in vacuo and the residue acidified with 1 N HCl and twice extracted with EtOAc. The combined extracts were washed sequentially with water and brine, dried (Na₂SO₄), filtered and evaporated to afford 102b which was used without further purification in step 8.

Step 8—To a solution of 102b (0.75 g, 1.994 mmol) and DCM (8 mL) was added DMF (2 drops) and 0.05 mL of and oxalyl chloride (0.348 mL, 0.505 g; 3.99 mmol). The reaction mixture was stirred overnight at RT. The volatile reactants were removed in vacuo and the crude acid chloride 102c was used directly in the next step.

Step 9—The acid chloride 102c (0.092 g)was dissolved in 3 mL of acetone and purged with nitrogen. A separate flask was charged with 4-amino-benzenesulfonamide (0.046 g; 0.270 mmol) and water (1 mL) was added to dissolve the sulfonamide. NaHCO₃ (0.050 g) was added and the acetone solution slowly added and allowed to stir overnight. The reaction mixture was extracted with EtOAc and washed with 10% HCl and brine. The EtOAc solution was dried (Na₂SO₄), filtered and evaporated and the crude product purified by SiO₂ chromatography eluting with EtOAc:hexanes (60:40) to afford I-1: mp 211-213; ms=476.

Compound I-3 was prepared in a by a similar procedure except in step 9, 4-amino-benzene was replaced by 3-(4-amino-3-methyl-phenoxy)-propane-1-sulfonic acid amide (J. H. Chan et al. *J. Med. Chem.* 2004 47(5):1175-1182)

EXAMPLE 2

2-[3-(2-Bromo-5-chloro-phenoxy)-4-chloro-phenyl]-N-(4-sulfamoyl-phenyl)-acetamide (I-4)

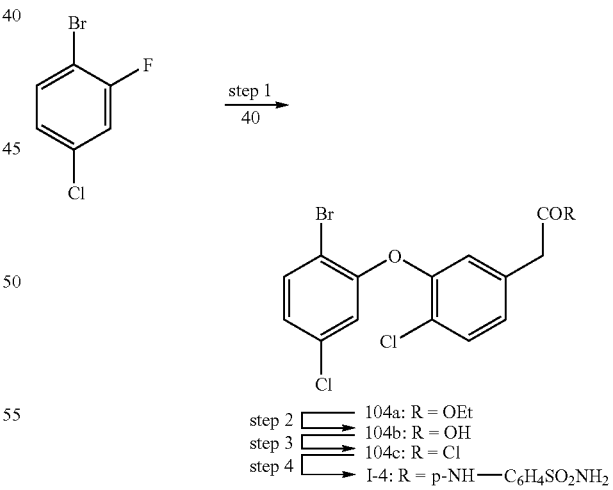

Step 1—A solution of phenol 59c (2.0 g, 9.32 mmol), 1-bromo-2-fluoro-4-chloro-benzene (1.28 mL, 2.15 g,10.25 mmol), K₂CO₃ (3.84 g, 30 mmol) and NMP (20 mL) was stirred and heated to 130° C. for 8 h. The reaction mixture was cooled to RT and diluted with H₂O (50 mL) and twice extracted with EtOAc. The combined organic extracts were washed sequentially with water (6 times) and brine, dried (Na₂SO₄), filtered and concentrated in vacuo. The crude product was purified by SiO₂ column chromatography eluting with (10% EtOAc/hexane) to afford 0.328 g (% theory) of I-4.

Steps 2-4 were carried out as described in steps 7-9 of Example 1 which afforded I-4

Compound I-3 was prepared in the same manner except in step 4, 4-amino-benzenesulfonamide was replaced by 3-(4-amino-3-methyl-phenoxy)-propane-1-sulfonic acid amide (J. H. Chan et al. *J. Med. Chem.* 2004 47(5): 1175-1182).

EXAMPLE 3

2-[4-Chloro-3-(4-cyano-2,6-dimethyl-phenoxy)-phenyl]-N-(4-sulfamoyl-phenyl)-acetamide (I-55)

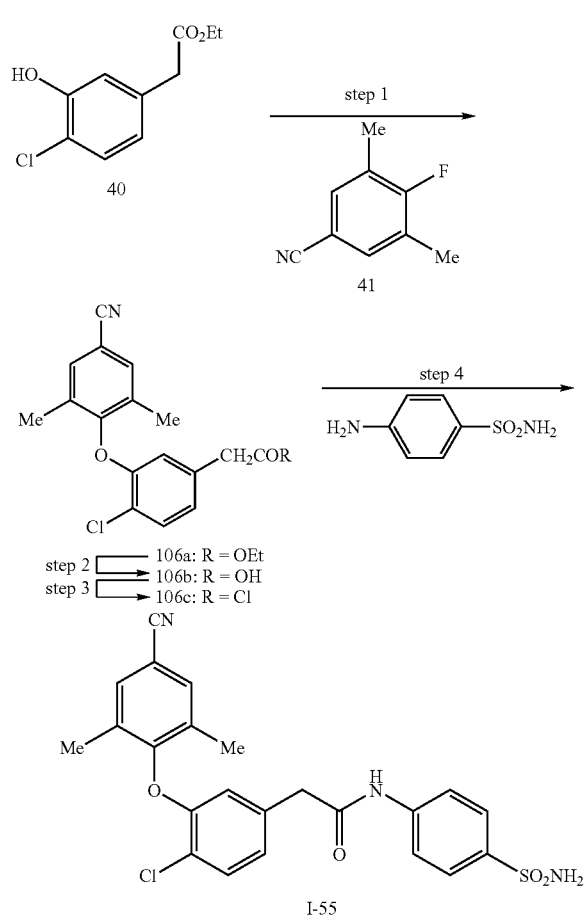

step 1—A solution of 40 (0.600 g, 2.79 mmol), 3,5-dimethyl4-fluorobenzonitrile (41, 0.459 g, 3.07 mmol), K₂CO₃ (1.157 g, 8.37 mmol) and NMP (6 mL) was stirred and heated to 120° C. for 6 h. When the starting material was consumed the solution was cooled and acidified with 10% HCl and twice extracted with EtOAc. The combined extracts were washed sequentially with water and brine, dried (Na₂SO₄), filtered and evaporated in vacuo. The crude product was purified by SiO₂ chromatography and eluted with an EtOAc/hexane gradient (100% hexane to 50% hexane) to afford 106a.

Steps 2-4 were carried out as described in steps 7-9 of Example 1 which afforded I-55.

Compound I-56 was prepared using a similar procedure except in step 4, 4-amino-benzenesulfonamide was replaced with 4-amino-2-methyl-benzenesulfonamide.

Compound I-68 was prepared using a similar procedure except in step 4, 4-amino-benzenesulfonamide was replaced with 2-chloroaniline.

Compound I-135 was prepared using a similar procedure except in step 4, 4-amino-benzenesulfonamide was replaced with 4-amino-2-chloro-benzenesulfonamide.

EXAMPLE 4

2-[4-Chloro-3-(3,5-dicyano-phenoxy)-phenyl]-N-(4-sulfamoyl-phenyl)-acetamide (I-3)

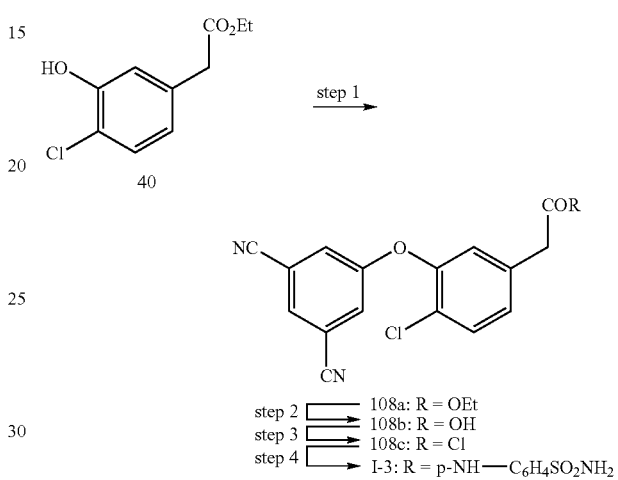

Step 1—A solution of 40 (1.335 g, 6.22 mmol), 5-fluoro-isophthalonitrile (1.0 g, 6.84 mmol), K₂CO3 (2.579 g, 18.66 mmol) and NMP (10 mL) was stirred and heated to 100° C. for 12 h. The reaction mixture was cooled to RT and diluted with H₂O (50 mL) and twice extracted with EtOAc. The combined organic extracts were washed sequentially with water and brine, dried (Na₂SO₄), filtered and concentrated in vacuo to afford 108a.

Steps 2-4 were carried out as described in steps 7-9 of Example 1 which afforded I-3.

Compound I-5 was prepared using a similar procedure except in step 4 of Example 3,4-amino-benzenesulfonamide was replaced with 2-chloro-phenylamine.

Compound I-6 was prepared using a similar procedure except in step 4, 4-amino-benzenesulfonamide was replaced with N,N-dimethyl-benzene-1,4-diamine.

Compound I-194 was prepared using a similar procedure except in step 4 of Example 3,4-amino-benzenesulfonamide was replaced with 2-pyrrol-1-yl-phenylamine.

Compound I-195 was prepared using a similar procedure except in step 4 of Example 3,4-amino-benzenesulfonamide was replaced with 2-fluoro-phenylarrane.

Compound I-196 was prepared using a similar procedure except in step 4 of Example 3,4-amino-benzenesulfonamide was replaced with 2-methoxy-phenylarmine.

Compound I-197 was prepared using a similar procedure except in step 4 of Example 3,4-amino-benzenesulfonamide was replaced with 2-iso-propyl-phenylamine.

Compound I-198 was prepared using a similar procedure except in step 4 of Example 3,4-amino-benzenesulfonamide was replaced with 2-methyl-phenylamine.

Compound I-199 was prepared using a similar procedure except in step 4 of Example 3,4-amino-benzenesulfonamide was replaced with 2-ethyl-phenylamine.

Compound I-200 was prepared using a similar procedure except in step 4 of Example 3, 4-amino-benzenesulfonamide was replaced with 2,3-dimethyl-phenylamine.

Compound I-201 was prepared using a similar procedure except in step 4 of Example 3, 4-amino-benzenesulfonamide was replaced with 2-methyl4-methoxy-phenylamine.

Compound I-202 was prepared using a similar procedure except in step 4 of Example 3, 4-amino-benzenesulfonamide was replaced with 4-cyclohexyl-phenylamine.

Compound I-203 was prepared using a similar procedure except in step 4 of Example 3, 4-amino-benzenesulfonamide was replaced with 2-amino-benzonitrile.

Compound I-204 was prepared using a similar procedure except in step 4, 4-amino-benzenesulfonamide was replaced with 2-trifluoromethyl-phenylamine.

Compound I-205 was prepared using a similar procedure except in step 4 of Example 3, 4-amino-benzenesulfonamide was replaced with 2-amino4,5-dimethoxy-benzoic acid methyl ester.

Compound I-208 was prepared in the same manner except in step 4, 4-amino-benzenesulfonamide was replaced with phenylamine.

EXAMPLE 5

2-[4-Chloro-3-(3-cyano-5-trifluoromethyl-phenoxy)-phenyl]-N-(4-sulfamoyl-phenyl)-acetamide (I-88)

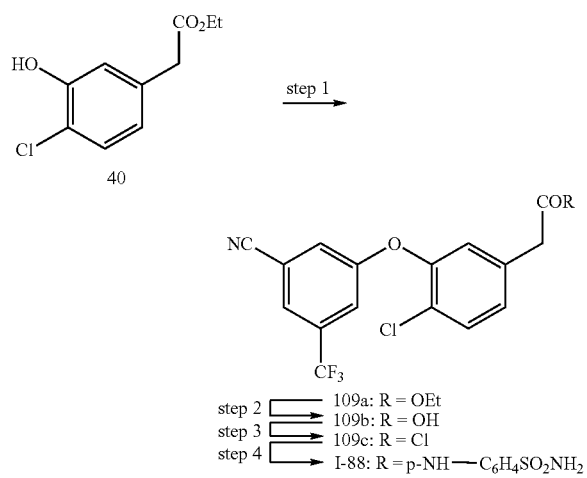

[4-Chloro-3-(3-cyano-5-trifluoromethyl-phenoxy)-phenyl]-acetic acid ethyl ester3-bromo-5-trifluoromethylphenol (109a)was prepared by condensing 40 and 3-fluoro-5-trifluoromethyl-benzonitrile (59b) using the procedure described in step 6 of example 1. Steps 2 to 4 were carried out by the procedure described in steps 7 to 9 of example 1 which afford I-88.

Compound I-89 was in the same procedure as I-88 except in step 4, 4-amino-benzenesulfonamide was replaced with 4-amino-2-methyl-benzenesulfonamide was replaced with Compound I-90 was in the same procedure as I-88 except in step 4, 4-amino-benzenesulfonamide was replaced with 4-amino-2-chloro-benzenesulfonamide was replaced with

EXAMPLE 6

2-[3-(3-Chloro-5-cyano-phenoxy)-4-methyl-phenyl]-N-[2-methyl4-(4-methyl-piperazine-1-sulfonyl)-phenyl]-acetamide (I-116)

Steps 1-3 are depicted in SCHEME 1 and Steps 4-8 are depicted in SCHEME 12

Step 1—To a cooled solution of ethyl 4-hydroxy-3-methoxyphenylacetate (4a; 13.7 g; 65.2 mmol) and 260 mL of $CH_2Cl_2$ under $N_2$ atmosphere was added dropwise triflic anhydride (16 mL; 97.9 mmol) followed by dropwise addition of pyridine (8.9 mL; 8.8 mmol). The reaction was stirred in an ice-water bath for 3 h. The solution was transferred to a separatory funnel and washed with water and brine, dried ($Na_2SO_4$), filtered and evaporated to yield 21 g (90%) of 4b.

Step 2—To a solution of ethyl 3-methoxy4-trifluorosulfonyloxyphenylacetate (4b) in 4 mL of THF cooled in an ice-water bath was added slowly a solution of Pd(dppf)Cl$_2$ (0.024 g; 0.029 mmol) and DIBAL-H (6 mL; 0.058 mmol; 1.0 M in PhMe)and a small quantity of THF followed by dimethylzinc (0.29 mL; 0.58 mmol; 2.0 M in PhMe). After addition was completed the ice bath was removed and the reaction allowed to warm to rt and then heated to reflux for 1 h. The reaction was carefully quenched with a small quantity of water, filtered through a pad of CELITE® and the solids washed thoroughly with EtOAc. The combined organic extracts were washed with water and brine, dried (MgSO$_4$) and the solvent evaporated to afford 0.240 g (85%) of ethyl 3-methoxy-4-methylphenylacetate (4c).

step 3—To a solution of 4c (2.2 g; 8.0 mmol) and 250 mL CH$_2$Cl$_2$ cooled to −78° C. was added dropwise via syringe BBr$_3$ (9.8 mL; 0.104 mol). After 1 h at −78° C. the reaction was stirred for 4 h in an ice-water bath. The reaction mixture was recooled to −78° C. and the reaction quenched aqueous NaHCO$_3$ then warmed to rt and the organic phase washed with water, saturated NaHCO$_3$ and brine. The organic phase was dried (MgSO$_4$) and the solvent evaporated to afford 1.4 g of ethyl 3-hydroxy-4-methylphenylacetate (6).

step 4—A solution of 3-chloro-5-fluorobenzonitrile (59a, 9.2 g, 59.14 mmol), 6 (10.44 g, 53.76 mmol), K$_2$CO$_3$ (22.29 g, 161.3 mmol) and NMP (100 mL) was stirred and heated to 120° C. for 6 h. The reaction mixture was cooled to 0° C. and diluted with saturated NaHSO$_3$ (100 mL) and twice extracted with EtOAc. The combined organic extracts were washed sequentially with water (6 times) and brine, dried (Na$_2$SO$_4$), filtered and concentrated in vacuo. The crude product was purified by SiO$_2$ column chromatography eluting with a EtOAc/hexane gradient (0 to 10% EtOAc) to afford 9.28 g (48% theory) of 112a.

steps 5-7—were carried out by the procedure described in steps 7-9 of Example 1 except in step 7, 4-amino-benzenesulfonamide was replaced with 4-amino-3-methyl-benzenesulfonyl fluoride which afforded 114.

step 8—A mixture of 114 (0.150 g, 0.317 mmol)and N-methyl-piperazine (0.176 µL, 0.159 g, 1.59 mmol) was heated to 120° C. without any solvent. The reaction mixture was cooled to RT and partitioned between EtOAc (25 mL) and 10% HCl (mL). The aqueous phase was extracted with EtOAc (25 mL). The aqueous phase was made basic with 10% NaOH and extracted twice with EtOAc and the combined organic extracts were washed sequentially with water and brine, dried (Na$_2$SO$_4$), filtered and evaporated in vacuo. The crude product was purified by column chromatography on SiO$_2$ eluting with DCM:MeOH (95:5) to afford I-116.

Compound I-115 was prepared using a similar procedure except in step 8 N-methyl-piperazine was replaced with morpholine.

Compound I-117 was prepared using a similar procedure except in step 8, N-methyl-piperazine was replaced with thiomorpholine.

Compound I-118 was prepared using a similar procedure except in step 8, N-methyl-piperazine was replaced with 2-morpholin4-yl-ethylamine.

Compound I-119 was prepared using a similar procedure except in step 8, N-methyl-piperazine was replaced with 3-amino-propan-1-ol.

Compound I-121 was prepared using a similar procedure except in step 8, N-methyl-piperazine was replaced with trans4-amino-cyclohexanol.

Compound I-122 was prepared using a similar procedure except in step 7, 4-amino-3-methyl-benzenesulfonyl fluoride was replaced with 4-amino-3-methyl-benzenesulfonamide and step 8 was omitted Compound I-123 was prepared using a similar procedure except in step 7, 4-amino-3-methyl-benzenesulfonyl fluoride was replaced with 4-amino-3-chloro-benzenesulfonamide and step 8 was omitted Compound I-128 was prepared using a similar procedure except in step 8, N-methyl-piperazine was replaced with tetrahydro-pyran4-ylamine.

Compound I-129 was prepared using a similar procedure except in step 8, N-methyl-piperazine was replaced with 1-amino-propan-2-ol.

Compound I-130 was prepared using a similar procedure except in step 8, N-methyl-piperazine was replaced with 2-methylsulfanyl-ethylamine.

Compound I-131 was prepared using a similar procedure except in step 8, N-methyl-piperazine was replaced with 3-methylsulfanyl-propylamine.

Compound I-224 was prepared using a similar procedure except in step 7, 4-amino-3-methyl-benzenesulfonyl fluoride was replaced with 3-amino4-methyl-pyridine and step 8 was omitted.

Compound I-225 was prepared using a similar procedure except in step 7, 4-amino-3-methyl-benzenesulfonyl fluoride was replaced with 2-amino-3-methyl-pyridine and step 8 was omitted.

Compound I-226 was prepared using a similar procedure except in step 7, 4-amino-3-methyl-benzenesulfonyl fluoride was replaced with 2,5-dimethyl-2H-pyrazol-3-ylamine and step 8 was omitted.

Compound I-227 was prepared using a similar procedure except in step 7, 4-amino-3-methyl-benzenesulfonyl fluoride was replaced with 2-methyl-2H-pyrazol-3-ylamine and step 8 was omitted.

Compound I-228 was prepared using a similar procedure except in step 7, 4-amino-3-methyl-benzenesulfonyl fluoride was replaced with N-(5-amino-4-methyl-pyridin-2-yl)-acetamide and step 8 was omitted.

Compound I-229 was prepared using a similar procedure except in step 7, 4-amino-3-methyl-benzenesulfonyl fluoride was replaced with 3-amino-6-methoxy-2-methyl-pyridine and step 8 was omitted.

Compound I-230 was prepared using a similar procedure except in step 7, 4-amino-3-methyl-benzenesulfonyl fluoride was replaced with 2-methyl-5-methylsulfanyl-2H-[1,2,4]triazol-3-ylamineand step 8 was omitted.

Compound I-235 was prepared using a similar procedure except in step 7, 4-amino-3-methyl-benzenesulfonyl fluoride was replaced with (4-amino-3-methyl-phenyl)-acetic ac id methyl ester and step 8 was omitted.

Compound I-236 was prepared base hydrolysis I-235 with LiOH in EtOH/H$_2$O.

Compound I-237 was prepared using a similar procedure except in step 7, 4-amino-3-methyl-benzenesulfonyl fluoride was replaced with N-(4-amino-3-methyl-phenyl)-methanesulfonamide and step 8 was omitted. N-(4-Amino-3-methyl-phenyl)-methanesulfonamide was prepared by mesylation of 3-methyl4-nitro-phenylamine followed by catalytic hydrogenation of the nitro group.

Compound I-238 was prepare as described for I-237 except N-(3-methyl4-nitro-phenyl)-methanesulfonamide (113a) was N-methylated to produce N-methyl-N-(3-methyl4-nitro-phenyl)-methanesulfonamide (113b) prior to reduction and acylation.

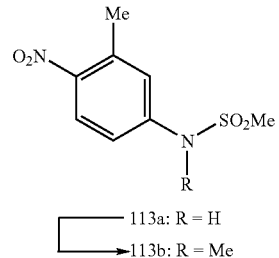

113a: R = H
113b: R = Me

NaH (0.057 g of a 60% dispersion in mineral oil, 1.1 equiv) was added to a solution of 113a (0.30 g, 1.3 mmol) in DMF (6 mL) cooled to 0° C. The solution was stirred for 10 min, and iodomethane (0.12 mL, 1.5 equiv) was added dropwise. The solution was stirred for 16 h and poured into a saturated NH$_4$Cl solution. The solution was extracted with EtOAc, and the combined organic layers were washed with water, brine, and dried (MgSO$_4$). Evaporation of the volatile materials 113b as a yellow oil (0.30 g, 94%).

EXAMPLE 7

2-[3-(3,5-Dicyano-phenoxy)4-methyl-phenyl]-N-(2-methyl-4-sulfamoyl-phenyl)-acetamide (I-43)

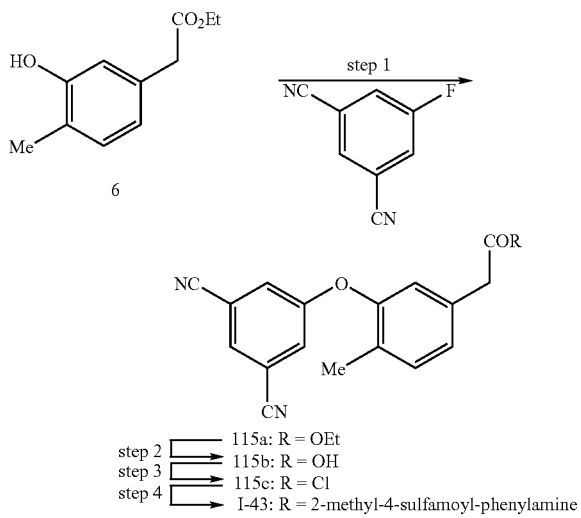

115a: R = OEt
step 2
115b: R = OH
step 3
115c: R = Cl
step 4
I-43: R = 2-methyl-4-sulfamoyl-phenylamine 5-Fluoro-isophthalonitrile was prepared from 3,5 dibromo-fluoro-benzene (59b) with $Zn(CN)_2/Pd[P(Ph)_3]_4$ mediated coupling.

step 1—A solution of 5-fluoro-isophthalonitrile (0.3742 g), 6 (0.450 g, 2.55 mmol), $K_2CO_3$ (0.962 g, 6.96 mmol) and NMP (5 mL) was stirred and heated to 120° C. for 6 h. The reaction mixture was cooled to RT and diluted with $H_2O$ (25 mL) and twice extracted with EtOAc. The combined organic extracts were washed sequentially with water (6 times) and brine, dried ($Na_2SO_4$), filtered and concentrated in vacuo. The crude product was purified by $SiO_2$ column chromatography eluting with a EtOAc/hexane gradient (100% to 75% hexane) to afford 115a.

steps 2-4—were carried out by the procedure described in steps 7-9 of Example 1 except in step 4 4-amino-3-methyl-benzenesulfonamide replaced 4-amino-3-benzenesulfonamide which afforded I-43

Compound I-34 was prepared using a similar procedure except in step 4, 2-chloro-phenylamine replaced 4-amino-3-methyl-benzenesulfonamide.

Compound I-44 was prepared using a similar procedure except in step 4, 4-amino-3-chloro-benzenesulfonamide replaced 4-amino-3-methyl-benzenesulfonamide.

EXAMPLE 8

2-[3-(2-Bromo-5-chloro-phenoxy)-4-methyl-phenyl]-N-(4-sulfamoyl-phenyl)-acetamide (I-30)

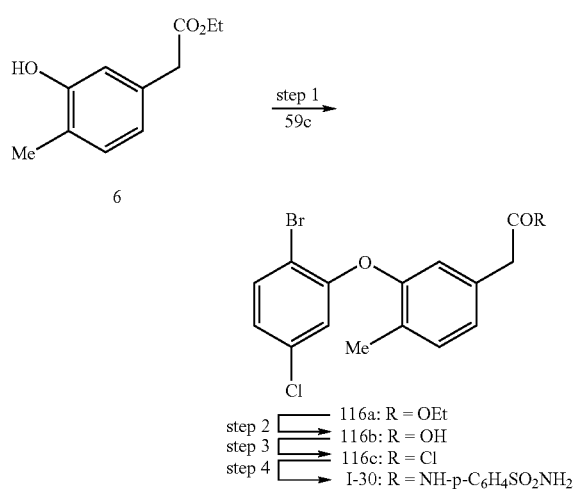

step 1—A solution of 1-bromo-4-chloro-2-fluoro-benzene (59c, 0.415 g, 1.98 mmol), 6 (0.350 g, 1.8 mmol), $K_2CO_3$ (0.746 g, 5.4 mmol) and NMP (4 mL) was stirred and heated to 120° C. for 6 h. The reaction mixture was cooled to RT and diluted with $H_2O$ (25 mL) and twice extracted with EtOAc. The combined organic extracts were washed sequentially with water (6 times) and brine, dried ($Na_2SO_4$), filtered and concentrated in vacuo. The crude product was purified by $SiO_2$ column chromatography eluting with a EtOAc/hexane (100% to 75% hexane) to afford 116a.

steps 2-4—were carried out by the procedure described in steps 7-9 of Example 1 which afforded I-30.

Compound I-31 was prepared using a similar procedure except in step 4, 4-amino-sulfonamide was replaced by 4-amino-3-methyl-sulfonamide.

Compound I-33 was prepared using a similar procedure except in step 4, 4-amino-sulfonamide was replaced by 2-chloro-phenylamine.

EXAMPLE 9

(4-{2-[3-(3-Chloro-5-cyano-phenoxy)-4-methyl-phenyl]-acetylamino}-3-methyl-benzenesulfonyl)-acetic acid (I-152)

The reactions are depicted in SCHEME 13 step 1—To a solution of 98a (7.76 g, 50 mmol) and EtOH (15 mL) was added portion wise a hot solution of $Na_2S_9.H_2O$ (9.6 g, 40 mmol), powdered sulfur (1.28 g, 40 mmol) and EtOH (50 mL). The solution was heated at reflux for 10 min after the addition was completed. To the solution was added portion wise NaOH (2 g, 50 mmol) over 5 min and the solution was stirred for an additional 10 min. The reaction mixture was cooled to RT and poured into ice water (200 mL), stirred, filtered and the solid washed with water. The filtrate was acidified with aqueous HCl to pH 2 and the resulting orange precipitate was washed with water and air dried. The crude product was chromatographed on $SiO_2$ and eluted with 20% EtOAc/hexane to afford 3 g of 98b as an orange powder.

step 2—To a solution of 98b (0.508 g, 3 mmol) and MeCN (10 mL) was added TEA (0.83 mL, 6 mmol). To the dark red solution was added methyl bromoacetate (0.31 mL, 3.3 mmol) and the reaction mixture was stirred overnight at RT. The reaction mixture was diluted with saturated $NH_4Cl$ and twice extracted with EtOAc, dried ($MgSO_4$) and concentrated in vacuo. The crude product was purified by $SiO_2$ chromatography eluting with a gradient of hexane/EtOAc (20% to 30% EtOAc) which afford 0.5 g of 98c as a yellow oil.

step 3—To a solution of 98c (0.484 g, 2 mmol) in DCM (20 mL) was added MCPBA (1.44 g, 5 mmol, 60% assay) and the reaction stirred at RT. Stirring was continued until the reaction was complete. m-Chlorobenzoic acid precipitated from the reaction. The precipitated solid was dissolved by addition of DCM until the precipitate dissolved and the DCM solution then was washed sequentially with saturated sodium bisulfite and 5% $NaHCO_3$, dried ($MgSO_4$) and evaporated to afford 0.538 g of 98d as an oil which solidified upon standing.

step 4—A mixture of 98d (0.537 g, 1.96 mmol), iron powder (0.55 g, 9.8 mmol, Fischer electrolyte iron powder), $NH_4Cl$ (0.53 g, 9.8 mmol) and EtOH/water (1: 1, 40 mL) was stirred at 85° C. for 2 h. The red solution was cooled to RT and filtered through a pad of CELITE® and the pad washed with EtOAc. The organic solvents were removed in vacuo and the residue suspended in water and twice extracted with EtOAc. The combined extracts were dried ($MgSO_4$), filtered and evaporated to afford 0.449 g of 100 as a brown oil which solidified upon standing.

step 5—To a solution of 94b (0.140 g) dissolved in DCM (10 mL) and 1 drop of DMF was added oxalyl chloride (1 mL). The reaction was stirred at RT for 1 h and the volatile solvents removed in vacuo to afford [3-(3-chloro-5-cyano-phenoxy) 4-methyl-phenyl]-acetyl chloride (94c). To a solution of 94c (0.113 g, 0.465 mmol), TEA (0.13 mL, 0.93 mmol) and EtOAc (6 mL) was added dropwise a solution of the acid chloride and EtOAc (4 mL) over a 2 h period. The reaction was stirred at RT for 2 h. The reaction mixture was diluted with water, twice extracted with EtOAc and the combined extracts washed sequentially with diluted HCl, saturated $NaHCO_3$, water and brine. The organic phase was dried ($MgSO_4$), filtered and concentrated in vacuo. The crude product was redissolved in a minimum volume of warm EtOAc and hexane was added until slightly cloudy. The white powder which precipitated was filtered and washed with 20% EtOAc/hexane to afford 0.161 g of 122.

Step 6—To a solution of 122 (0.161 g, 0.036 mmol), THF (12 mL) and water (6 mL) was added LiOH.H$_2$O (0.0384 g, 0.916 mmol) and the reaction stirred at RT for 2 h. The reaction mixture was evaporated, 1 N HCl was added and the resulting mixture twice extracted with EtOAc. The combined extracts were washed with brine, dried (MgSO$_4$), filtered and concentrated in vacuo. The crude product was purified by SiO$_2$ chromatography eluting with MeOH/DCM/HOAc (5:94.5:0.5) which afforded 0.255g of I-152 as a white foam.

Compounds I-137, I-154 and I-157 were prepared similarly except in step 3 methyl bromoacetate was replaced with bromoacetonitrile, (2-bromo-ethyl)-carbamic acid tert-butyl ester and 3-bromoporpanol respectively. After condensation of [2-(4-amino-3-methyl-benzenesulfonyl)-ethyl]-carbamic acid tert-butyl ester with 112c, the Boc group was removed by treatment with TFA/DCM.

EXAMPLE 10

2-[3-(3-Chloro-5-cyano-phenoxy)4-ethyl-phenyl]-N-(4-sulfamoyl-phenyl)-acetamide (I-45)

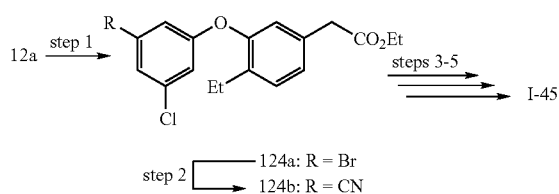

(4-Ethyl-3-hydroxy-phenyl)-acetic acid ethyl ester (12a) was prepared as depicted in SCHEME 1. Alternatively, 12a can be prepared by the procedures in steps 1-3 of example 6 except diethylzinc was used in place of dimethylzinc in step 2

To a stirred solution of ethyl 3-methoxyphenylacetate (16.0 g; 82.38 mmol) in CH$_2$Cl$_2$ (200 mL) at rt was added dropwise AcCl (9.88 mL; 138.9 mmol) followed by stannic chloride (16.9 mL; 169 mmol; 1.0 M solution in CH$_2$Cl$_2$). The reaction mixture was stirred at rt for 6 h and poured into an ice-water mixture. The aqueous phase was extracted with CH$_2$Cl$_2$ and the combined extracts were washed with water, dried (Na$_2$SO$_4$) and the solvent removed in vacuo. The crude product 8 was purified by chromatography on silica gel and eluting with CH$_2$Cl$_2$:EtOAc (20:1) to yield 13.96 g (69.5%) of a white solid.

To a solution of 8 (19g; 80.42 mmol) and 200 mL of TFA cooled to 0° C. was added an excess of Et$_3$SiH and the reaction allowed to warm to rt for 3 h. Excess TFA was removed in vacuo and the residue partitioned between water and CH$_2$Cl$_2$. The crude product was purified by chromatography on silica gel and eluting with CH$_2$Cl$_2$:hexane (3:1) to yield 3.0 g (16%) of 10.

A solution of ethyl 4-ethyl-3-methoxyphenylacetate (10; 3.0 g; 13.50 mmol) and CH$_2$Cl$_2$ (80 mL) was cooled to −78° C. and a solution of BBr$_3$ (5.10 mL; 53.94 mmol; 1.0 M in CH$_2$Cl$_2$) over 30 min. After 1 h at −78° C. the reaction was allowed to warm to rt and stirred for 12 h. The reaction was cooled in an ice-water bath and the reaction quenched with 20 mL of water. The aqueous phase was extracted with CH$_2$Cl$_2$: EtOAc (4:1 v/v), dried (Na$_2$SO$_4$), filtered and evaporated. The crude product was purified by silica gel chromatography and eluting with a CH$_2$Cl$_2$:EtOAc gradient (100:1 to 100:4) to yield 12a (2.0 g; 71%): ms 209.2 (M+H)$^+$.

Step 1—To a solution of ethyl 4-ethyl-3-hydroxyphenylacetate (12a, 0.700 g; 3.36 mmol) and NMP (8 mL) was added K$_2$CO$_3$ (1.393 g; 10.08 mmol) and 1-bromo-3-chloro-5-fluorobenzene (59b, 0.774 g; 3.7 mmol). The reaction was heated to 120° C. and monitored by TLC. After 8 h the reaction was cooled to RT and 10% HCl was added. The mixture was extracted with EtOAc and the combined extracts were washed with H$_2$O and brine. The extracts were dried (Na$_2$SO$_4$) filtered and evaporated. The crude product was chromatographed with silica gel and eluted with a gradient of hexane/EtOAc (100 to 60% hexane) to afford 124a.

Step 2—To a solution of the 124a (0.300 g; 0.754 mmol) in DMF (5mL) was added Zn(CN)$_2$ (0.354 g; 3.017 mmol) and Pd(PPh$_3$)$_4$ (0.131 g; 0.113 mmol). The solution was purged with N$_2$ and heated at 85° C. overnight. H$_2$O and EtOAc were added and the mixture stirred for 30 min. The suspension was filtered and the combined filtrate extracted with EtOAc. The organic phase was washed with H$_2$O and brine, dried (Na$_2$SO$_4$) and evaporated. The crude product was chromatographed with silica gel and eluted with a gradient of hexane/EtOAc (100 to 70% hexane) to afford 124b Step 3—A dried round bottom purged with nitrogen was charged with 124b (0.380 g; 1.1 mmol) and THF (15 mL) and stirred under a stream of nitrogen. To the reaction vessel was added LiOH (0.079 g; 3.32 mmol) was added followed by deionized water (4 mL). The reaction was allowed to stir for an additional hour under nitrogen. The homogeneous mixture was cooled to 0° C. and quenched with 10% aqueous HCl. The reaction mixture was stirred for an additional 15 min. The crude mixture was extracted with DCM and washed with water and brine. The organic layers were dried (Na$_2$SO$_4$) and filtered. Solvent removed in vacuo to yield a crude oil which was used without any further purification.

step 4—A round bottom flask was charged with carboxyl acid from step 3 (1.1 mmol) and DCM (5 mL) and the solution stirred under nitrogen at RT. To the solution was added SOCl$_2$ (0.192 mL; 2.2 mmol) dropwise followed by a single drop of DMF. The reaction was stirred for 1 h at RT. Excess solvent and oxalyl chloride were removed in vacuo, to yield acid chloride as a crude yellow oil which was used without any further purification.

step 5—The acid chloride (0.15 mmol) from the previous step was dissolved in acetone (1 mL) and purged with nitrogen. NaHCO$_3$ (0.025 g; 0.3 mmol) was added followed by 4-amino-benzenesulfonamide (0.026 g; 0.15 mmol) and water (2 mL). The mixture was sonicated for 5 min and allowed to stir for 12 h at RT. The reaction mixture was filtered and the crude product was washed sequentially with water and diethyl ether to afford I-45.

Compound I-46 was prepared in the same manner except 4-amino-benzenesulfonamide was replaced with 4-amino-3-methyl-benzenesulfonamide.

Compound I-47 was prepared in the same manner except 4-amino-benzenesulfonamide was replaced with 4-amino-3-chloro-benzenesulfonamide.

Compound I-207 was prepared in the same manner except 4-amino-benzenesulfonamide was replaced with phenylamine.

Compound I-48 was prepared in the same manner except 4-amino-benzenesulfonamide was replaced with 4-amino-3, N-dimethyl-benzenesulfonamide.

Compound I-73 was prepared in the same manner except 4-amino-benzenesulfonamide was replaced with 2-chlorophenylamine.

EXAMPLE 11

2-[3-(3-Cyano-5-fluoro-phenoxy)4-methyl-phenyl]-
N-(4-sulfamoyl-phenyl)-acetamide (I-11)

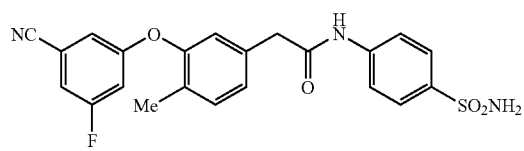

Compound I-11 was prepared by condensation of 6b with 1,3-dibromo-5-fluorobenzene as described in step 1 of Example 10 which affords [3-(3-bromo-5-fluoro-phenoxy)4-methyl-phenyl]-acetic acid ethyl ester. Displacement of the bromide with Zn(CN)$_2$ as described in step 2 of Example 10 affords [3-(3-cyano-5-fluoro-phenoxy)4-methyl-phenyl]-acetic acid ethyl ester which was converted to I-11 as described in step 7 to 9 of Example 1.

Compound I-12 was prepared in the same manner except 4-amino-benzenesulfonamide was replaced with 2-chloro-phenylamine.

EXAMPLE 12

2-[3-(3-Chloro-5-cyano-phenoxy)4-methyl-phenyl]-
N-[4-((S)-2,3-dihydroxy-propoxy)-2-methyl-phenyl]-acetamide (I-150)

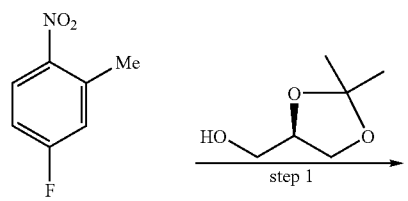

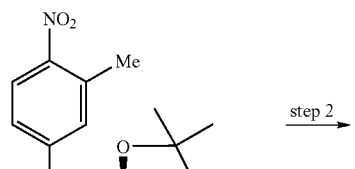

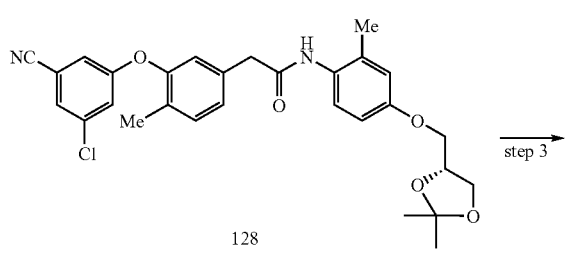

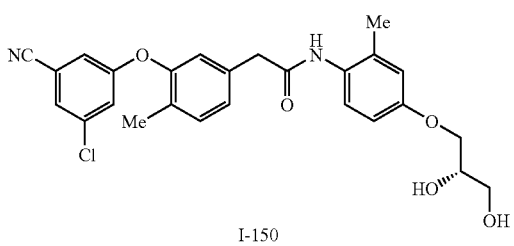

Step 1—The (R)-dioxolane (1.04g, 7.86 mmol) was added to a suspension of NaH (0.35 g of a 60% dispersion in mineral oil, 1.1 equiv) in DMF (30 mL) under N$_2$ atmosphere at 0° C. The solution was stirred for 10 min, and 118a (0.96 mL, 1 equiv) was added dropwise. The resulting red solution was stirred overnight, poured into a saturated solution of NH$_4$Cl, and extracted with a 1:1 EtOAc/hexane solution. The organic solution was washed with water, brine, and dried (MgSO$_4$). The solvent was evaporated and the crude product purified by SiO$_2$ chromatography eluting with a EtOAc/hexane gradient (5 to 25% EtOAc) to afford 1.10 g (52%) of the nitro compound. The oil was dissolved in EtOH (40 mL), and 10% Pd/C (0.09 g) was added. The solution was shaken under 40 psi of hydrogen for 3 h, filtered, and evaporated to afford 0.95 g (97%) of 126.

step 2—Condensation of 94c and 126 was carried out as described in step 9 of example 1 which afforded 128.

step 3—The amide 128 (0.23 g, 0.44 mmol) was dissolved in a mixture of 2 M HCl (2 mL) and dioxane (2 mL). The solution was stirred at RT for 3 h. DCM was added, and the organic extracts were dried (MgSO$_4$) and concentrated in vacuo. The crude product was purified by SiO$_2$ chromatography eluting with a MeOH/DCM gradient (0% to 5% MeOH) which afforded 0.12 g (55%) of I-150.

Compound I-151 was prepared as described above except the acetonide of 1,2,4-butanetriol was used in step 1.

EXAMPLE 13

2-[3-(3-Chloro-5-cyano-phenoxy)4-methyl-phenyl]-
N-[2-methyl4-(2-morpholin-4-yl-acetyl)-phenyl]-acetamide; compound with trifluoro-acetic acid
(I-163)

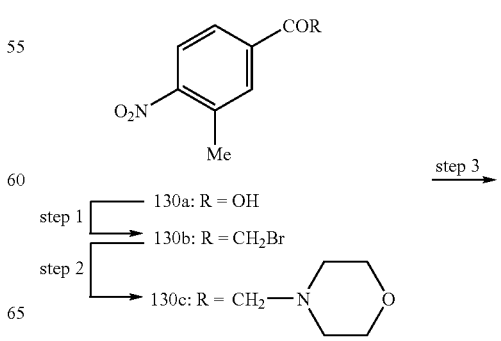

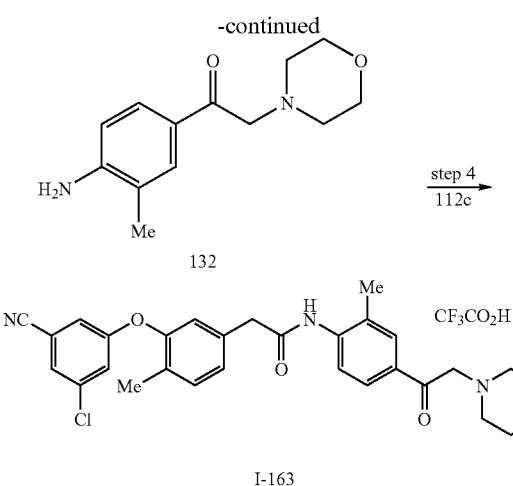

step 1—Thionyl chloride (7.55 g, 1.1 equiv) was added to a suspension of 130a (10.45 g, 57.7 mmol) in anhydrous toluene (50 mL) under $N_2$ atmosphere. DMF (0.44 mL, 0.1 equiv) was added, and the reaction was heated to reflux. The solution became homogenous, and was heated 4 h, cooled to RT and stirred for 2 d. The volatile materials were removed. Dry benzene (40 mL) was added and the volatile materials were again removed. This was repeated two more times. NMR of the resulting oil ($C_6D_6$) showed formation of the acid chloride. The resulting oil (11.3 g) was divided into 3 portions for conversion into the (x-bromoketone. To a solution of the acid chloride in dry $Et_2O$ (60 mL) that had been cooled to −78° C. was quickly added an excess of a fresh ethereal solution of diazomethane. The solution was warmed to 0° C. and bubbling was observed. The reaction was monitored by TLC, and after 20 min at 0° C. a solution of 48% HBr (25 mL) was added. A precipitate formed, and the reaction mixture was diluted with an additional 100 mL of ether. The three reaction solutions were combined, the aqueous layer was separated and extracted with ether. The organic layers were combined, washed sequentially with water, $NaHCO_3$ and brine, and dried ($MgSO_4$). The solvent was removed, and the material was crystallized from EtOAc/hexanes which afforded 130b. NMR of the resulting solid (shows a 8:1 ratio of bromomethyl product to chlororomethyl impurity and was used in the subsequent reactions.

step 2—Morpholine (1.35 mL, 5 equiv) was added dropwise to a 0° C. solution of 130b (0.80 g, 3.1 mmol) in dry THF (10 mL) under $N_2$ atmosphere. The solution was warmed to 10° C. After 30 min, the solution was added dropwise to a mixture of EtOAc and saturated $NaHCO_3$ solution. The mixture was extracted with EtOAc, the volatile materials were removed, and the residue was purified by $SiO_2$ chromatography eluting with a EtOAc/hexane gradient (25% to 75% EtOAc) to afford 0.51 g (62%) of 130c.

step 3—The nitro compound 130c (0.50 g, 1.9 mmol) was dissolved in EtOH (10 mL) and $PtO_2$ (21 mg, 0.05 equiv) was added. The solution was degassed and placed under a $H_2$ atmosphere (balloon pressure). After 1 h, a grey solid precipitated. The solution was stirred for 2 h, filtered and the precipitate washed with EtOAc and MeCN. The solvent was removed, and the residue was purified by $SiO_2$ chromatography eluting with a MeOH/DCM gradient (2% to 5% MeOH) to afford 0.21 g (47%) of 132.

step 4—Condensation of 94c and 132 was carried out as described in step 9 of example 1 which afforded I-163.

Compound I-159 was prepared in a similar manner except N-methyl piperazine was used in place of morpholine. I-161 and I-163 were prepared in a similar manner except thiomorpholine was used in place of morpholine. The sulfur atom was oxidized to the corresponding sulfoxide and sulfone with $HIO_4$ and MCPBA.

EXAMPLE 14

2-[3-(3-Chloro-5-cyano-phenoxy)-4-methyl-phenyl]-N-[4-(1,1-dioxo-1λ6-isothiazolidin-2-yl)-2-methyl-phenyl]-acetamide (I-170)

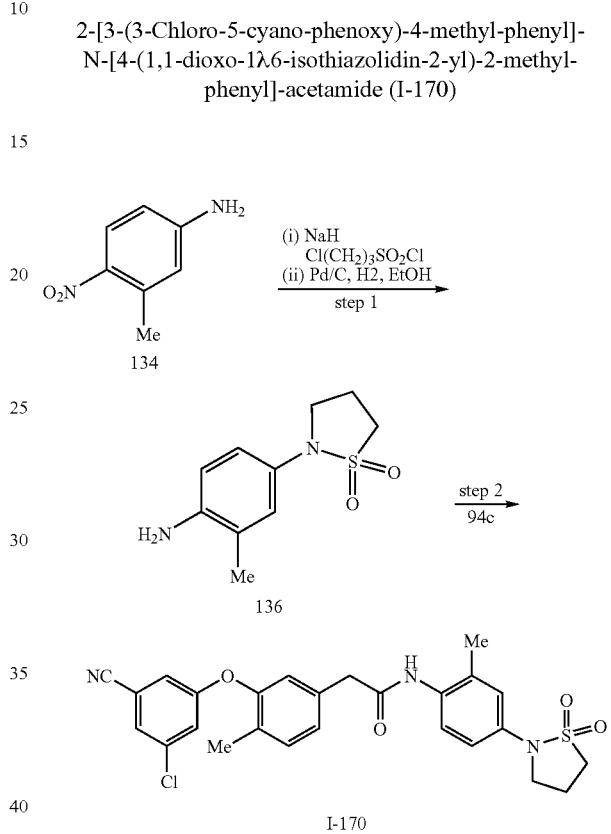

step 1—NaH (0.40 g of a 60% dispersion, 3 equiv) was added to a solution of the 134 (0.50 g, 3.29 mmol) in DMF (18 mL) at 0° C. The solution was warmed to RT. After 30 min, a DMF (4 mL) solution of 3-chloro-propane-1-sulfonyl chloride (0.81 g, 1.4 equiv) was added. The solution was stirred at RT for 45 min, and then heated to reflux for 4 h. The reaction mixture was cooled to RT and quenched with ice water. The aqueous layer was extracted with EtOAc, and the organic layers were dried ($gSO_4$). Filtration and evaporation of the volatile materials afforded an oil that was purified by $SiO_2$ chromatography eluting with an EtOAc/hexane gradient (50% to 70% EtOAc) to afford the sulfonamide as a yellow solid (0.49 g, 59%). This sulfonamide was dissolved in EtOH (20 mL). 10% Pd/C (0.05 g) was added, the solution was placed under a $H_2$ atmosphere (50 psi), and the solution was shaken for 3 h. Filtration of the reaction mixture and evaporation of the volatile materials afforded 0.44 g of 136.

step 2—Condensation of 94c and 136 was carried out as described in step 9 of example 1 which afforded I-170.

Compound I-158 was made by a similar procedure except in 3-chloro-propane-1-sulfonyl chloride was replaced with 3-chloro-butane-1-sulfonyl chloride

EXAMPLE 15

N-(4-{2-[3-(3-Chloro-5-cyano-phenoxy)4-methyl-phenyl]-acetylamino}-3-methyl-phenyl)-oxalamic acid ethyl ester (I-178)

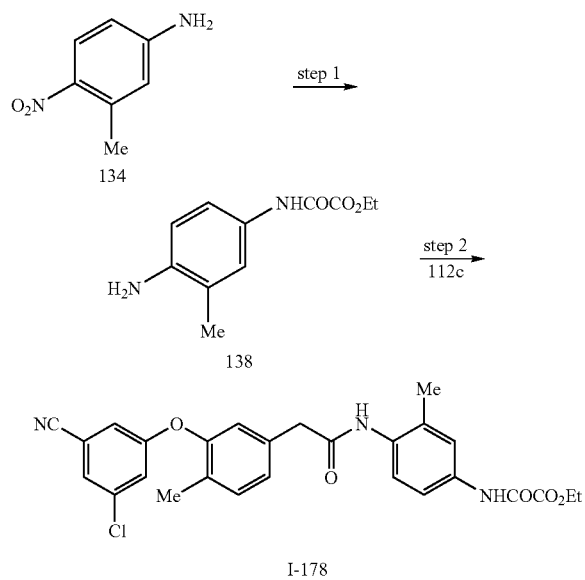

step 1—TEA (1 mL, 1.1 equiv) and chloro-oxo-acetic acid ethyl ester (0.9 mL, 1.2 equiv) were added consecutively to a 0° C. solution of 134 (1.0 g, 6.57 mmol) in THF (60 mL). The reaction was stirred overnight at RT, evaporated to dryness, and dissolved in DCM. The organic layer was washed with water, dried (MgSO$_4$), and concentrated to give a yellow solid. The solid was purified by SiO$_2$ chromatography eluting with a EtOAc/hexane gradient (0% to 30% EtOAc) to afford 0.847 g (51%) of the amide as a yellow solid. The amide (500 mg) was dissolved in EtOH (20 mL), 10% Pd/C (50 mg) was added, and the reaction was placed under H$_2$ (50 psi) and shaken for 2 h. Filtration of the catalyst and concentration of the filtrate afforded 0.320 g (73%) of 138a as a light yellow oil (0.320 g, 73%)

step 2—Condensation of 84c and 138 was carried out as described in step 9 of example 1 which afforded I-178.

EXAMPLE 16

2-[3-(3-Bromo-5-chloro-phenoxy)4-ethyl-phenyl]-N-(4-sulfamoyl-phenyl)-acetamide (I-15)

step 1—A dried round bottom purged with nitrogen was charged with [3-(3-bromo-5-chloro-phenoxy)4-ethyl-phenyl]-acetic acid ethyl ester (124a (example 10), 0.200 g; 0.5 mmol) and THF (6 mL) and maintained under a stream of nitrogen. To the reaction vessel was added LiOH (0.036 g; 1.5 mmol) and deionized water (2 mL). The reaction was allowed to stir for 1 h under N$_2$. The homogeneous mixture cooled to 0° C. and 10% aqueous HCl was added. The reaction mixture was stirred for an additional 15 min. The crude mixture was extracted with DCM and washed with water and brine. The organic layers were dried (Na$_2$SO$_4$), filtered and the solvent removed in vacuo to yield [3-(3-bromo-5-chloro-phenoxy)-4-ethyl-phenyl]-acetic acid as a crude oil which was used without any further purification.

step 2—The acid chloride was prepared from the acid obtained in step 1 as described in step 8 of Example 1.

step 3—The acid chloride (0.25 mmol) from step 2 was dissolved in acetone (3 mL) and purged with nitrogen. NaHCO$_3$ (0.042 g; 0.5 mmol) was added followed by 4-amino-benzenesulfonamide (0.043 g; 0.25 mmol) and water (6 mL). The mixture was sonicated for 5 min and allowed to stir for 12 h at RT. The reaction mixture was filtered and the crude product was washed sequentially with water and diethyl ether to afford I-22.

Compound I-16 was prepared in the same manner except 4-amino-benzenesulfonamide was replaced with 2-chloro-phenylamine.

EXAMPLE 17

2-[3-(2-Bromo-5-chloro-phenoxy)4-ethyl-phenyl]-N-(4-sulfamoyl-phenyl)-acetamide (I-15)

step 1—To a solution of ethyl 4-ethyl-3-hydroxyphenylacetate (12a, 1.000 g; 4.8 mmol) and NMP (10 mL) was added K$_2$CO$_3$ (1.99 g; 14.4 mmol) and 1-bromo4-chloro-2-fluorobenzene (1.106 g; 5.28 mmol).

The reaction was heated to 120° C. and monitored by TLC. After 8 h the reaction was cooled to RT and 10% HCl was added. The mixture was extracted with EtOAc and the combined extracts were washed with H$_2$O and brine. The extracts were dried (Na$_2$SO$_4$) filtered and evaporated. The crude product was chromatographed with SiO$_2$ and eluted with a gradient of hexane/EtOAc (100:0 to 60:40) to afford [3-(2-bromo-5-chloro-phenoxy)4-ethyl phenyl]-acetic acid ethyl ester.

steps 2 and 3—Hydrolysis and formation of the acid chloride were carried as described in step 7and 8 of Example 1 and used without additional purification.

step 4—[3-(2-Bromo-5-chloro-phenoxy)-4-ethyl-phenyl]-acetic acid ethyl ester (0.5 mmol) was dissolved in acetone (2 mL) and the flask was purged with N$_2$. NaHCO$_3$ (0.084 g; 1.0 mmol) was added followed by 4-amino-benzenesulfonamide (0.086 g; 0.5 mmol) and water (6 mL). The mixture was sonicated for 5 min and allowed to stir for 12 h at RT. The reaction mixture was filtered and the crude product was washed sequentially with water and diethyl ether to afford I-15.

EXAMPLE 18

2-[3-(5-Chloro-2-cyano-phenoxy)-4-ethyl-phenyl]-N-(4-sulfamoyl-phenyl)-acetamide (I-17)

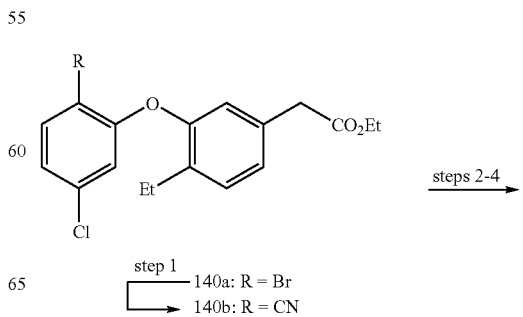

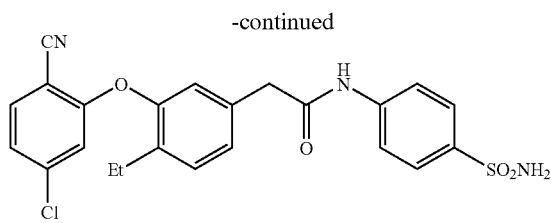

step 1—To a solution of 140b (step 1 of example 17, 0.629 g; 1.58 mmol) in DMF (14 ml) was added Zn(CN)₂ (0.929 g; 7.9 mmol) and Pd(PPh₃)₄ (0.366 g; 0.32 mmol). The solution was purged with N₂ and heated at 85° C. overnight. The reaction mixture was partitioned between H₂O and EtOAc and the mixture stirred for 30 min. The suspension was filtered and the combined filtrate extracted with EtOAc. The organic extracts were washed with H₂O and brine, dried (Na₂SO₄) and evaporated. The crude product was purified by SiO₂ chromatography and eluted with a gradient of hexane/EtOAc (100:0 to 70:30) to afford 140b.

steps 2 and 3—Hydrolysis and formation of the acid chloride were carried as described in step 7 and 8 of Example 1 and used without additional purification.

step 4—The acid chloride from step 3 (0.29 mmol) was dissolved in acetone (1 mL) of acetone and purged with nitrogen. NaHCO₃ (0.049 g; 0.58 mmol) was added followed by 4-amino-benzenesulfonamide (0.050 g; 0.29 mmol) and water (2 mL). The mixture was sonicated for 5 min and allowed to stir for 12 h at RT. The reaction mixture was filtered and the crude product was washed sequentially with water and diethyl ether to afford I-17.

Compound I-18 was prepared in the same manner except 4-amino-benzenesulfonamide was replaced by 2-chloro-phenylamine.

EXAMPLE 19

2-[3-(2,5-Dichloro-phenoxy)4-ethyl-phenyl]-N-(4-sulfamoyl-phenyl)-acetamide (I-19)

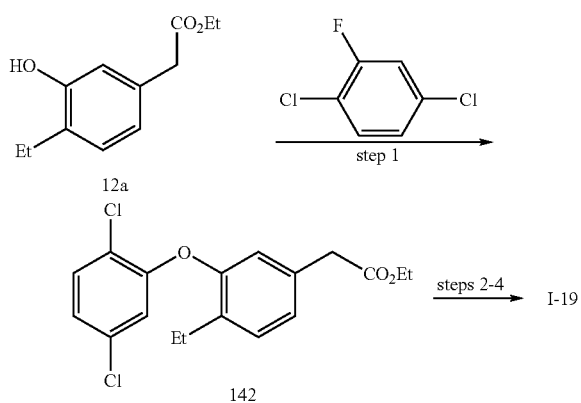

step 1—To a solution of 12a (0.200 g; 0.960 mmol) and NMP (4 mL) was added K₂CO₃ (0.398 g; 2.88 mmol) and 1,4-dichloro-2-fluoro-benzene (0.124 mL; 1.056 mmol). The reaction was heated to 120° C. and monitored by TLC. After 8 h the reaction was cooled to RT and 10% HCl was added. The mixture was extracted with EtOAc and the combined extracts were washed with H₂O and brine. The extracts were dried (Na₂SO₄) filtered and evaporated. The crude product was purified by SiO₂ chromatography eluting with a gradient of hexane/EtOAc (100:0 to 60:40) to afford 142.

steps 2 and 3—Hydrolysis and formation of the acid chloride were carried as described in step 7 and 8 of Example 1 and used without additional purification.

step 4—The acid chloride from step 3 (0.415 mmol) was dissolved in acetone (2 mL) and the flask and purged with nitrogen. NaHCO₃ (0.070 g; 0.83 mmol) was added followed by 4-amino-benzenesulfonamide (0.072 g; 0.415 mmol) and water (4 mL). The mixture was sonicated for 5 min and allowed to stir for 12 h at RT. The reaction mixture was filtered and the crude product was washed sequentially with water and diethyl ether to afford I-19

Compound I-21 was prepared in the same manner except 4-amino-benzenesulfonamide was replaced with 2-chloro-phenylamine.

EXAMPLE 20

2-[3-(2,6-Dichloro-phenoxy)4-ethyl-phenyl]-N-(4-sulfamoyl-phenyl)-acetamide (I-20)

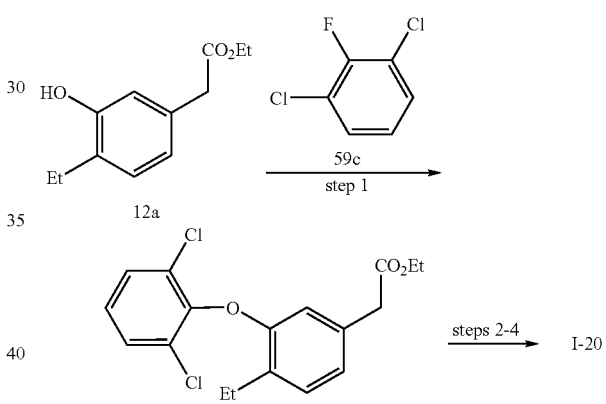

step 1—To a solution of 12a (0.200 g; 0.960 mmol) and NMP (4 mL) was added K₂CO₃ (0.398 g; 2.88 mmol) and 1,3-dichloro-2-fluoro-benzene (0.174 g; 1.056 mmol). The reaction was heated to 120° C. and monitored by TLC. After 8 h the reaction was cooled to RT and 10% HCl was added. The mixture was extracted with EtOAc and the combined extracts were washed with H₂O and brine. The extracts were dried (Na₂SO₄) filtered and evaporated. The crude product was purified by SiO₂ chromatography eluting with a hexane/EtOAc gradient (0 to 40% EtOAc) to afford 144.

steps 2 and 3—Hydrolysis and formation of the acid chloride were carried as described in step 7 and 8 of Example 1 and used without additional purification.

step 4—The acid chloride from step 3 (0.14 mmol) was dissolved in acetone (2 mL) and the flask was purged with nitrogen. NaHCO₃ (0.024 g; 0.28 mmol) was added followed by 4-amino-benzenesulfonamide (0.024 g; 0.14 mmol) and water (4 mL). The mixture was sonicated for 5 min and allowed to stir for 12 h at RT. The reaction mixture was filtered and the crude product was washed sequentially with water and diethyl ether to afford I-20.

Compound I-23 was prepared in the same manner except 4-amino-benzenesulfonamide was replaced by 2-chloro-phenylamine.

EXAMPLE 21

2-[3-(3-Bromo-2,5-dichloro-phenoxy)4-ethyl-phenyl]-N-(4-sulfamoyl-phenyl)-acetamide (I-35)

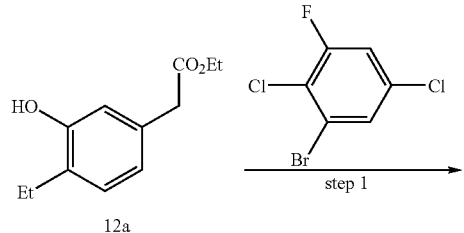

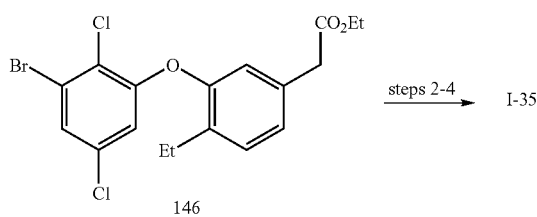

step 1—To a solution of 12a (0.450 g; 2.160 mmol) and NMP (5 mL) was added K₂CO₃ (0.896 g; 6.48 mmol) and 1-bromo-2,5-dichloro-3-fluoro-benzene (0.580 g; 2.38 mmol). The reaction was heated to 120° C. and monitored by TLC. After 8 h the reaction was cooled to RT and 10% HCl was added. The mixture was extracted with EtOAc and the combined extracts were washed with H₂O and brine. The extracts were dried (Na₂SO₄), filtered and evaporated. The crude product was purified by SiO₂ chromatography eluting with a gradient of hexane/EtOAc (100:0 to 60:40) to afford 146.

steps 2 and 3—Hydrolysis and formation of the acid chloride were carried as described in step 7and 8 of Example 1 and used without additional purification.

step 4—The acid chloride from step 3 (0.112 mmol) was dissolved in acetone (1 mL) and the flask was purged with nitrogen. NaHCO₃ (0.019 g; 0.224 mmol) was added followed by 4-amino-benzenesulfonamide (0.019 g; 0.112 mmol) and water (2 mL). The mixture was sonicated for 5 min and allowed to stir for 12 h at RT. The reaction mixture was filtered and the crude product was washed sequentially with water and diethyl ether to afford I-35.

Compound I-36 was prepared in the same manner except 4-amino-benzenesulfonamide was replaced with 4-amino-3-methyl-benzenesulfonamide.

Compound I-37 was prepared in the same manner except 4-amino-benzenesulfonamide was replaced with 2-chloro-phenylamine.

EXAMPLE 22

N-(2-Chloro-phenyl)-2-[3-(3,5-dibromo-2-chloro-phenoxy)4-ethyl-phenyl]-acetamide (I-38)

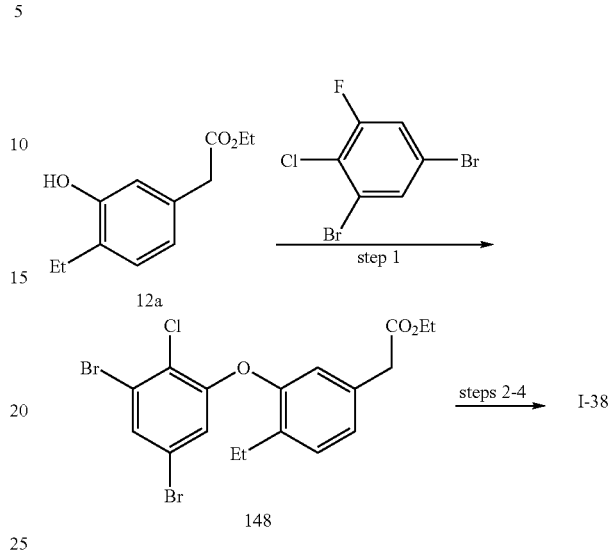

step 1—To a solution of 12a (0.500 g; 2.4 mmol) and NMP (5 mL) was added K₂CO₃ (0.995 g; 7.2 mmol) and 2-chloro-1,5-dibromo-3-fluoro-benzene (0.762 g; 2.64 mmol). The reaction was heated to 120° C. and monitored by TLC. After 8 h the reaction was cooled to RT and 10% HCl was added. The mixture was extracted with EtOAc and the combined extracts were washed with H₂O and brine. The extracts were dried (Na₂SO₄), filtered and evaporated. The crude product was purified by SiO₂ chromatography eluting with a hexane/EtOAc gradient (0 to 40% EtOAc) to afford 148.

steps 2 and 3—Hydrolysis and formation of the acid chloride were carried as described in step 7and 8 of Example 1 and used without additional purification.

step 4—The acid chloride from step 3 (0.155 mmol) was dissolved in acetone (1 mL) and purged with nitrogen. NaHCO₃ (0.026 g; 0.31 mmol) was added followed by (0.027 g; 0.155 mmol) and water (2 mL). The mixture was sonicated for 5 min and allowed to stir for 12 h at RT. The reaction mixture was filtered and the crude product was washed sequentially with water and diethyl ether to afford I-38.

EXAMPLE 23

2-[3-(2-Chloro-3,5-dicyano-phenoxy)4-ethyl-phenyl]-N-(4-sulfamoyl-phenyl)-acetamide (I-52)

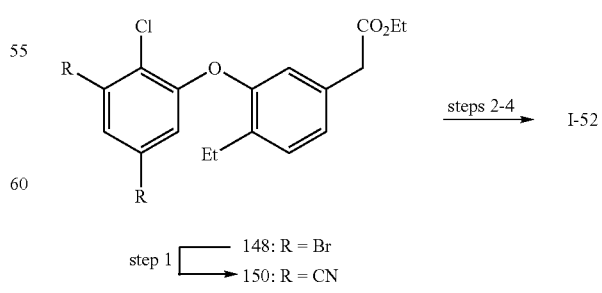

step 1—To a solution of the ester 148 (0.660 g; 1.43 mmol) in THF (7 ml) was added Zn(CN)₂ (0.673 g; 5.73 mmol) and Pd(PPh$_3$)$_4$ (0.248 g; 0.215 mmol). The solution was purged with N$_2$ and heated at 85° C. overnight. The reaction mixture was partitioned between H$_2$O and EtOAc and the mixture stirred for 30 min. The suspension was filtered and the combined filtrate extracted with EtOAc. The organic extracts were washed with H$_2$O and brine, dried (Na$_2$SO$_4$) and evaporated. The crude product was purified by SiO$_2$ chromatography eluting with a hexane/EtOAc gradient (0 to 30%) to afford 150.

steps 2 and 3—Hydrolysis and formation of the acid chloride were carried as described in step 7 and 8 of Example 1 and used without additional purification.

step 4—The acid chloride from step 3 (0.12 mmol) was dissolved in acetone (1 mL) and the flask was purged with nitrogen. NaHCO$_3$ (0.020 g; 0.24 mmol) was added followed by 4-amino-benzenesulfonamide (0.021 g; 0.12 mmol) and water (2 mL). The mixture was sonicated for 5 min and allowed to stir for 12 h at RT. The reaction mixture was filtered and the crude product was washed sequentially with water and diethyl ether to afford I-52.

Compound I-53 was prepared in the same manner except in step 4, 4-amino-benzenesulfonamide was replaced with 4-amino-3-methyl-benzenesulfonamide.

Compound I-54 was prepared in the same manner except in step 4, 4-amino-benzenesulfonamide was replaced with 4-amino-3-chloro-benzenesulfonamide.

Compound I-60 was prepared in the same manner except in step 4, 4-amino-benzenesulfonamide was replaced with 2-chlorophenylamine.

Compound I-208 was prepared in the same manner except in step 4, 4-amino-benzenesulfonamide was replaced with phenylamine.

EXAMPLE 24

2-[3-(2-Chloro-5-cyano-3-fluoro-phenoxy)4-ethyl-phenyl]-N-(4-sulfamoyl-phenyl)-acetamide (I-49)

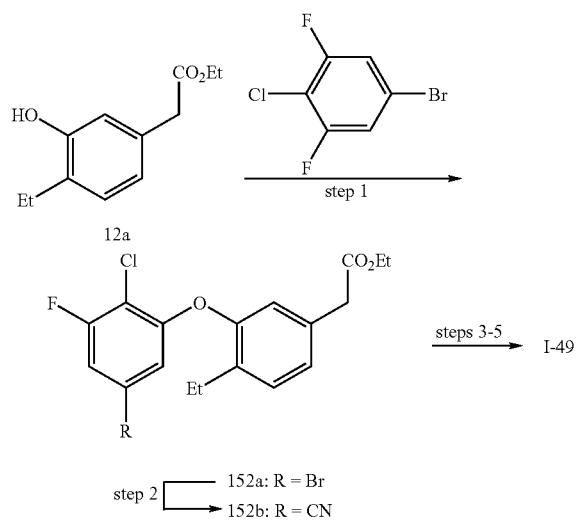

step 1—To a solution of 12a (0.400 g; 1.920 mmol) and NMP (5 mL) was added K$_2$CO$_3$ (0.796 g; 5.76) and 5-bromo-2-chloro-1,3-difluoro-benzene (0.481 g; 2.11 mmol). The reaction was heated to 120° C. and monitored by TLC. After 8 h the reaction was cooled to RT and 10% HCl was added. The mixture was extracted with EtOAc and the combined extracts were washed with H$_2$O and brine. The extracts were dried (Na$_2$SO$_4$), filtered and evaporated. The crude product was purified by SiO$_2$ chromatography eluting with a hexane/EtOAc gradient (0 to 40% EtOAc) to afford 152a.

step 2—To a solution of 152a (0.420 g; 1.01 mmol) in DMF (5 ml) was added Zn(CN)$_2$ (0.475 g; 4.04 mmol) and Pd(PPh$_3$)$_4$ (0.175 g; 0.152 mmol). The solution was purged with N$_2$ and heated at 85° C. overnight. The reaction mixture was cooled to RT and partitioned between H$_2$O and EtOAc and the mixture stirred for 30 min. The suspension was filtered and the combined filtrate extracted with EtOAc. The organic extracts were washed with H$_2$O and brine, dried (Na$_2$SO$_4$) and evaporated. The crude product was purified by SiO$_2$ chromatograph eluting with a hexane/EtOAc gradient (0 to 30% EtOAc) to afford 152b.

steps 3 and 4—Hydrolysis and formation of the acid chloride were carried as described in step 7 and 8 of Example 1 and used without additional purification.

step 5—The acid chloride from step 4 (0.1 mmol) was dissolved in acetone (1 mL) and the flask was purged with nitrogen. NaHCO$_3$ (0.017 g; 0.2 mmol) was added followed by 4-amino-benzenesulfonamide (0.017 g; 0.1 mmol) and water (2 mL). The mixture was sonicated for 5 min and allowed to stir for 12 h at RT. The reaction mixture was filtered and the crude product was washed sequentially with water and diethyl ether to afford I-49.

Compound I-50 was prepared in the same manner except 4-amino-benzenesulfonamide was replaced with 4-amino-3-methyl-benzenesulfonamide.

Compound I-59 was prepared in the same manner except 4-amino-benzenesulfonamide was replaced with 2-chlorophenylamine.

EXAMPLE 25

2-[3-,(5-Bromo-2-chloro-3-fluoro-phenoxy)4-ethyl-phenyl]-N-(4-sulfamoyl-phenyl)-acetamide (I-39)

I-39 was prepared as described in the previous example except cyanide displacement of the aryl bromide (step 2) was omitted.

Compound I-40 was prepared in the same manner except in step 4, 4-amino-benzenesulfonamide was replaced by 4-amino-3-methyl-benzenesulfonamide.

Compound I-41 was prepared in the same manner except in step 4, 4-amino-benzenesulfonamide was replaced with 2-chlorophenylamine.

EXAMPLE 26

2-[3-(3-Cyano-5-difluoromethyl-phenoxy)4-ethyl-phenyl]-N-(4-sulfamoyl-phenyl)-acetamide (I-91, see SCHEME 8)

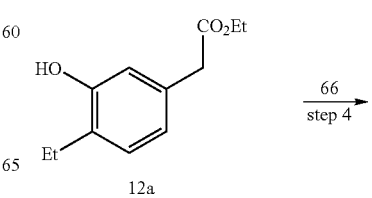

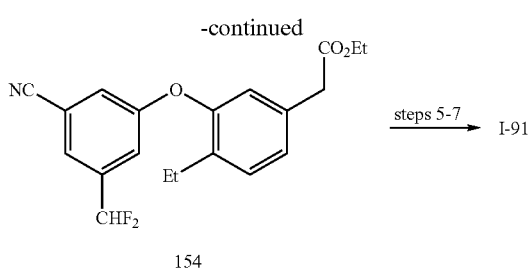

step 1—To a solution of 64a (25.39 g, 0.1 mol) and anhydrous Et$_2$O (125 mL) cooled to −78° C. and maintained under an Ar atmosphere was added dropwise over 30 min n-BuLi (40 mL, 0.1 mol, 2.5 M in hexane). The yellow solution was stirred at −78° C. for 10 min. To the reaction mixture was added dropwise dry DMF (8.52 mL, 2.2 mmol) over 5 min and the reaction stirred at −78° C. for 10 min before the cooling bath was removed and the reaction allowed to warm to −30° C. over 30 min. The reaction vessel was placed in an ice-water bath and warmed to −10° C. The mixture was slowly added to an ice cold saturated aqueous NH$_4$Cl solution (400 mL). The organic layer was separated and the aqueous phase thrice extracted with Et$_2$O. The combined extracts were washed with water, dried (MgSO$_4$), filtered and evaporated to afford an oil which solidified on standing. The crude product was purified by SiO$_2$ chromatography eluting with a hexane/EtOAc gradient (97:3 to 95:5) to afford 15g of 64b.

step 2—To a solution of 64b (32.4 g, 0.15 mol) and DCM (160 mL) cooled to −10° C. in an ice/MeOH/water bath under an Ar atmosphere in a septum-capped I L Nalgene narrow-neck bottle is added dropwise DAST (35.85 mL. 0.27 mol). The reaction mixture was stirred overnight. The reaction mixture was added dropwise over a 30 min period to saturated aqueous NaHCO$_3$ (400 mL) cooled to 0° C. Additional saturated NaHCO$_3$ was added to maintain the reaction at a slightly basic pH. The phases were separated and the aqueous phase was extracted twice with Et$_2$O and the combined extracts dried (MgSO$_4$) and concentrated at 30° C. under house vacuum to afford 36 g of an orange oil which was purified by bulb-to-bulb distillation in a Kugel-Rohr at 100° C. under house vacuum to afford 30.65 g of 64c.

step 3—A solution of 64c (41.6 g, 0.182 mol), Pd[P(Ph)$_3$]$_4$ (0) (15 g, 13 mmol), and zinc cyanide (12.82 g, 0.109 mol) in dry DMF (400 mL) under nitrogen was heated to 80° C. for 5.5 h. The reaction mixture was cooled to RT, the yellow solid filtered and the filtrate added to water (500 mL). The filtrate was thrice extracted with Et$_2$O and the combined extracts washed twice with water, dried (MgSO$_4$), filtered and evaporated at 30° C. The crude was purified by SiO$_2$ chromatography eluting with a hexane/EtOAc gradient (100:0 to 95:5 to 90:10) to provide 26.3 g of 66 as a colorless oil which partially crystallizes.

step 4—To a solution of 12a (0.400 g; 1.920 mmol) and NMP (4 mL) was added K$_2$CO$_3$ (0.796 g; 5.76) and 3-fluoro-5-(difluoromethyl)-benzonitrile (66, 0.362 g; 2.11 mmol). The reaction was heated to 120° C. and monitored by TLC. After 8 h the reaction was cooled to RT and 10% HCl was added. The mixture was extracted with EtOAc and the combined extracts were washed with H$_2$O and brine. The extracts were dried (Na$_2$SO$_4$) filtered and evaporated. The crude product was purified by SiO$_2$ chromatographed eluting with a gradient of hexane/EtOAc (100:0 to 60:40) to afford 154.

steps 5 and 6—Hydrolysis and formation of the acid chloride were carried as described in step 7 and 8 of Example 1 and used without additional purification.

step 7—The acid chloride from step 6 (0.25 mmol) was dissolved in acetone (1 mL) and purged with nitrogen. NaHCO$_3$ (0.042 g; 0.5 mmol) was added followed by 4-amino-benzenesulfonamide (0.043 g; 0.25 mmol) and water (2 mL). The mixture was sonicated for 5 min and allowed to stir for 12 h at RT. The reaction mixture was filtered and the crude product was washed sequentially with water and diethyl ether to afford I-91.

Compound I-101 was prepared in the same manner except in step 7, 4-amino-benzenesulfonamide was replaced with 4-amino-3-methyl-benzenesulfonamide.

Compound I-140 was prepared in the same manner except in step 7, 4-amino-benzenesulfonamide was replaced with 4-amino-3-chloro-benzenesulfonamide.

EXAMPLE 27

N-(2-Chloro-phenyl)-2-[3-(3,5-dicyano-phenoxy)4-ethyl-phenyl]-acetamide (I-25)

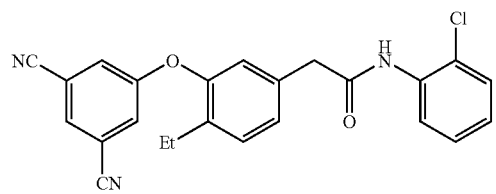

step 1—Coupling of 5-fluoroisophthalonitrile and 12a was carried out as described in step 1 of example 7.

steps 2 and 3—Hydrolysis and formation of the acid chloride were carried as described in step 7 and 8 of Example 1 and used without additional purification.

step 4—To a solution of the acid chloride from step 3 (0.15 mmol), TEA (22.7 µL, 0.225 mmol) and DCM (4 mL) cooled in an ice bath and maintained under a nitrogen atmosphere was added a solution of 2-chloro-phenylamine (15 µL, 0.0182 g; 0.1425 mmol) was added dropwise. The mixture was stirred for 12 h at RT. The solvents were removed in vacuo and the residue partitioned between H$_2$O. The aqueous phase was extracted with EtOAc and the combined extracts sequentially washed with I N HCL, saturated NaHCO$_3$ and brine. The organic extracts were dried (Na$_2$SO$_4$), filtered and the solvents remove in vacuo. The solid was triturated with Et$_2$O and filtered I-25.

EXAMPLE 28

2-[3-(3-Chloro-5-cyano-phenoxy)4-methoxy-phenyl]-N-(4-sulfamoyl-phenyl)-acetamide (I-62)

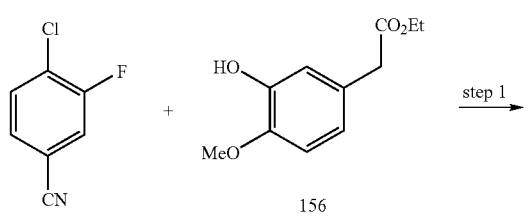

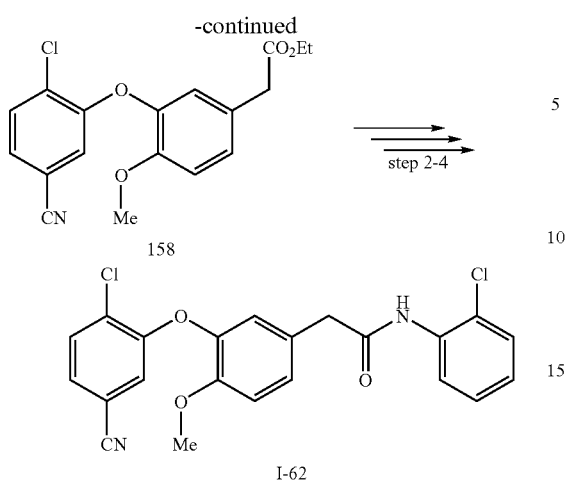

158

I-62 step 1—To a solution of ethyl 4-methoxy-3-hydroxyphenylacetate (156, 1.0 g; 4.46 mmol) and NMP (10 mL) was added $K_2CO_3$ (1.85 g; 13.38) and 4-chloro-3-fluoro-benzonitrile (0.0.763 g; 4.9 mmol). The reaction was heated to 120° C. and stirred overnight. The reaction was cooled to RT and 10% HCl was added. The mixture was extracted with EtOAc and the combined extracts were washed with $H_2O$ and brine. The extracts were dried ($Na_2SO_4$), filtered and evaporated. The crude product was purified by $SiO_2$ chromatography eluting with a gradient of hexane/EtOAc (100:0 to 60:40) to afford 158.

steps 2 and 3—Hydrolysis and formation of the acid chloride were carried as described in step 7 and 8 of Example 1 and used without additional purification.

step 4—To a solution of the acid chloride from step 3 (0.36 mmol), TEA (75.2 µL, 0.0546 g, 0.54 mmol) and DCM (3 mL) cooled in an ice bath and maintained under a nitrogen atmosphere was added 2-chloro-phenylamine (36 µL, 0.0436 g; 0.342 mmol) was added dropwise. The mixture was stirred for 12 h at RT. The solvents were removed in vacuo and the residue partitioned between $H_2O$ and EtOAc. The aqueous phase was extracted with EtOAc and the combined extracts sequentially washed with I N HCl, saturated $NaHCO_3$ and brine. The organic extracts were dried ($Na_2SO_4$), filtered and the solvents remove in vacuo. The solid was triturated with $Et_2O$ and filtered to afford I-62.

Compound I-65 was prepared in the same manner except in step 4, 2-chloro-phenylamine was replaced by 4-amino-benzenesulfonamide.

Compound I-66 was prepared in the same manner except in step 4, 2-chloro-phenylamine was replaced by 4-amino-3-methyl-benzenesulfonamide.

Compound I-67 was prepared in the same manner except in step 4, 2-chloro-phenylamine was replaced by 4-amino-3-chloro-benzenesulfonamide.

EXAMPLE 29

2-[3-(3-Chloro-5-cyano-phenoxy)-4-methoxy-phenyl]-N-(4-sulfamoyl-phenyl)-acetamide (I-61)

Compound I-61 was prepared by the procedures described in the previous example except in step 1, 4-chloro-3-fluoro-benzonitrile was replaced by 3-chloro-5-fluoro-benzonitrile.

Compound I-57 was prepared in the same manner except in step 4, 2-chloro-phenylamine was replaced with 4-amino-benzenesulfonamide.

Compound I-64 was prepared in the same manner except in step 4, 2-chloro-phenylamine was replaced with 4-amino-3-chloro-benzenesulfonamide.

Compound I-210 was prepared in the same manner except in step 4, 2-chlorophenylamine was replaced with phenylamine.

EXAMPLE 30

2-[3-(3-Cyano-5-difluoromethyl-phenoxy)4-methoxy-phenyl]-N-(4-sulfamoyl-phenyl)-acetamide (I-92)

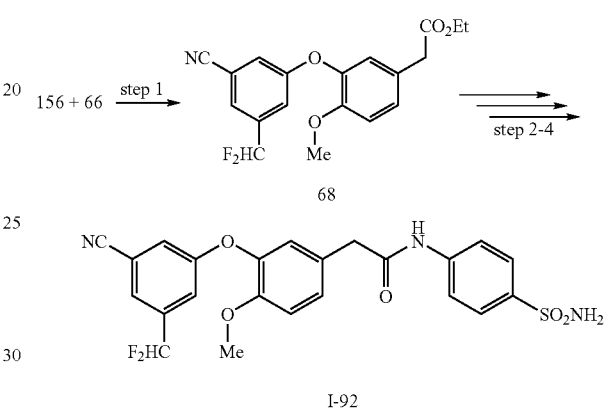

I-92 step 1—Coupling of 66 and 156 to afford 68 was carried out as described in step 4 of example 26.

steps 2 and 3—Hydrolysis and formation of the acid chloride were carried as described in step 7and 8 of Example 1 and used without additional purification.

step 4—was carried out as described in step 4 of example 26 to afford I-92.

Compound I-93 was prepared in the same manner except in step 7, 4-aminobenzenesulfonate was replaced with 4-amino-3-methyl-benzenesulfonamide.

Compound I-94 was prepared in the same manner except in step 7, 4-aminobenzenesulfonate was replaced with 4-amino-3-chloro-benzenesulfonamide.

EXAMPLE 31

2-[4-Chloro-3-(3-chloro-5-cyano-phenoxy)-2-fluoro-phenyl]-N-(2-methyl4-sulfamoyl-phenyl)-acetamide (I-42)

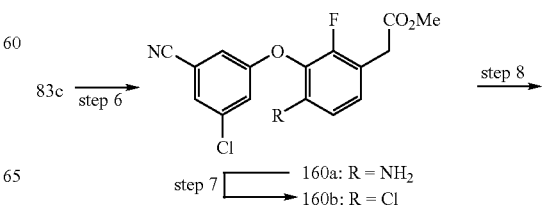

-continued

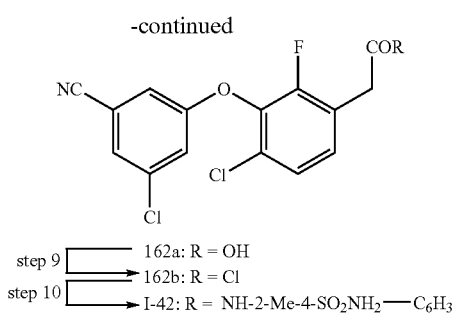

step 9 [ 162a: R = OH
       → 162b: R = Cl
step 10 [→ I-42: R = NH-2-Me-4-SO₂NH₂—C₆H₃ step 1—(Steps 1-5 are depicted in Scheme 9) A 100 ml round bottom flask was charged under a stream of nitrogen with 3,5-dichlorobenzonitrile (81a, 7.0 g, 40.69 mmol) and anhydrous DMF (75 mL). To the solution was added sodium methoxide (2.26 g, 44.76 mmol) and resulting solution was stirred further at RT for 24 h. When the reaction was complete, aqueous 10% hydrochloric acid added drop wise to the reaction vessel. The crude mixture was extracted with EtOAc and sequentially washed with aqueous acid, water and brine. The EtOAc extracts were dried (Na₂SO₄), filtered and the solvent was removed in vacuo to afford a crude solid which was recrystallized from hexane/acetone to afford 5.9 g (86%) of 81b.

step 2—A 250 mL flask was charged with 81b (7.0 g, 41.766 mmol) and 2,4,6-collidine (100 mL). The mixture was heated to 170° C. and LiI (16.76 g, 125.298 mmol) was added and the reaction mixture was heated for 4 h. When 81b was consumed the reaction was cooled to RT and quenched with 10% aqueous HCl. The resulting mixture was extracted with EtOAc and washed with water and brine. The EtOAc extract was dried over (Na₂SO₄) and filtered. The solvent was removed in vacuo to afford a yellow oil which was purified by silica gel chromatography eluting with EtOAc/hexane (10:90) to afford 6.0 g (94%) of 81c.

step 3—A 250 mL round-bottom flask was charged with 81c (6.0 g, 39.070 mmol) and anhydrous THF (100 mL) and the solution was cooled to 0° C. To the cooled solution was added sodium tert-butoxide (46.89 g, 4.51 mmol) and the resulting solution stirred for 1 h. 2,3,4-Trifluoro-nitro-benzene (6.92 g, 39.070 mmol) was added dropwise while maintaining the reaction at 0° C. until phenol was completely consumed. The mixture was quenched by addition of 10% aqueous HCl and the resulting mixture was stirred for an additional hour. The mixture was extracted with EtOAc and washed with water and brine. The EtOAc was dried (Na₂SO₄) and filtered. The solvent was removed in vacuo to yield a yellow oil which was purified by SiO₂ column chromatography eluting with hexane/EtOAc (92:8) to afford 10 g (82%) of 83a.

step 4—To a solution of tert-butyl ethyl malonate (10.31 g, 54.80 mmol) and anhydrous NMP (200 mL) cooled to 0° C. and stirred under a nitrogen atmosphere. To this solution was added NaH 40% in mineral oil (1.84 g, 76.70 mmol). The mixture was allowed to stir at 0° C. for an additional 1 h. The bis-aryl ether 83a (15.00 g, 49.80 mmol) was then added to the reaction vessel and stirred under nitrogen at RT until the reaction was complete. The mixture was quenched by addition of aqueous 10% HCl at RT. The mixture was extracted with EtOAc and washed with water and brine. The EtOAc was dried (Na₂SO₄) and filtered. The solvent was removed in vacuo to afford 83b as a light yellow oil which was used in the next step without any further purification.

step 5—The diester 83b (24.0 g, 50.117 mmol) was dissolved in dichloroethane (300 mL) and TFA (6.29 g,55.13 mmol) and heated to 75° C. for 24 h. The mixture was cooled to RT and solvent and excess TFA were removed in vacuo. The crude oil was redissolved in DCM and cooled to 0° C. and aqueous NaHCO₃ was added. The mixture was extracted with DCM and washed with water and brine. The DCM was dried (Na₂SO₄), filtered and the solvent was removed in vacuo to afford a yellow oil. The crude oil was purified by SiO₂ chromatography eluting with hexane/EtOAc (90:10) to afford 15.0 g (80%) of 83c step 6—A 250 mL round bottom flask was charged with 83c (8.0 g, 21.12 mmol) and absolute EtOH. To the reaction vessel was added ammonium chloride (2.26 g, 42.244 mmol), water (30 mL) and iron (1.17 g, 21.12 mmol). The reaction was stirred and heated to 80° C. for 4 h. When 83c was consumed, the heterogeneous mixture was filtered through a pad of CELITE® and the filter cake was washed with EtOAc. The aqueous filtrate was extracted with EtOAc and washed with water and brine. The combined EtOAc extracts were dried over (Na₂SO₄) and filtered. The solvent was removed in vacuo to afford a pale oil which was purified by SiO₂ chromatography eluting with hexane:EtOAc (85:15) to afford 6.0 g (87%) of 160a.

step 7—A 100 mL round bottom flask was charged with anhydrous MeCN (15 mL) under a continuous stream of nitrogen. To this mixture was added Cu(H)Cl₂ (0.083 g, 0.624 mmol) and tert-butyl nitrite (0.064 g, 0.624 mmol). The mixture was heated to 70° C. 30 min. To this mixture was added 160a (0.100 g, 0.624 mmol) in a single portion and stirring continued for an additional 2 h. Upon consumption of starting materials the mixture was cooled to RT and reaction mixture quenched with aqueous 10% HCl. The mixture was extracted with EtOAc and the combined extracts were washed with water and brine. The EtOAc extract was dried (Na₂SO₄) and filtered. The solvent was removed in vacuo to afford a light brown oil which was purified by SiO₂ chromatography eluting with hexane/EtOAc (96:4) to afford 0.080 g (76%) of 160b.

step 8—A dried 100 mL round bottom flask purged with nitrogen and charged with 160b (2.0 g; 5.43 mmol) and dissolved in THF (20 mL) and stirred under a stream of nitrogen. To the reaction vessel was added LiOH (0.46 g; 10.86 mmol) followed by 5 mL deionized water. The reaction was stirred for 1 h under a continuous stream of nitrogen. The homogeneous mixture was quenched at 0° C. with 10% aqueous HCl. The reaction mixture was stirred for an additional 15 minutes. The crude mixture was extracted with EtOAc and washed with water and brine. The organic extracts were dried (Na₂SO₄) and filtered. The solvent was removed in vacuo and the crude acid 162a was used without any further purification.

step 9—A 100 mL round bottom was charged with 162a (0.200 g, 0.520 mmol) and 5 mL of DCM and the solution was stirred under nitrogen at RT. To the solution was added thionyl chloride (0.061 g, 0.520 mmol) dropwise followed by a single drop of DMF. The reaction was stirred for 1 h at RT. Excess solvent and thionyl chloride were removed in vacuo to afford the carboxylic acid 162b as a crude yellow oil which was used in the next reaction without any further purification.

step 10—A 100 mL round bottom was charged with 4-amino-3-methyl-benzenesulfonamide (0.260 g, 1.40 mmol) and dissolved in 5 mL of acetone and NaHCO₃ (0.117 g, 1.40 mmol) under nitrogen. To the stirred mixture was added dropwise 162b (0.500 g, 1.40 mmol) dissolved in 7 mL of acetone and resulting mixture stirred for 24 h at RT. When starting material was consumed the reaction mixture was cooled to 0° C. and quenched with 10% aqueous HCl. The reaction mixture was extracted with EtOAc and washed with aqueous 10% HCl, water, and brine. The organic extracts were dried (Na$_2$SO$_4$) and filtered. The solvent was removed in vacuo to yield a crude solid which was purified by SiO$_2$ chromatography eluting with DCM/MeOH (93:7) to afford 0.64 g (90%) of I-42: ms (M−H)$^−$=507; mp.:250.1-252.3° C.; Elemental Analysis: calcd; C, 51.98; H, 3.17; N, 8.27; found: C, 51.20; H, 3.01; N, 8.10 (with 0.4M H$_2$O).

Compound I-98 was prepared in the same manner except in step 10, 4-amino-benzenesulfonamide was replaced by 2-chlorophenylamine.

Compound I-100 was prepared in the same manner except in step 10, 4-amino-benzenesulfonamide was replaced by 4-amino-3-chloro-benzenesulfonamide.

Compound I-108 was prepared in the same manner except in step 10, 4-amino-benzenesulfonamide was replaced by 4-amino-3,N-dimethyl-benzenesulfonamide.

Compound I-239 was prepared in the same manner except in step 10, 4-amino-benzenesulfonamide was replaced by 4-amino-3-methyl-benzamide.

Compound I-111 was prepared in the same manner except in step 10, 4-amino-benzenesulfonamide was replaced by 3-methyl4-methylamino-benzenesulfonamide.

Compound I-168 was prepared in the same manner except in step 10, 4-amino-benzenesulfonamide was replaced by 4-amino-3-chloro-N-methyl-benzenesulfonamide.

EXAMPLE 32

N-[4-(3-Amino-propionylsulfamoyl)-2-chloro-phenyl]-2-[4-chloro-3-(3-chloro-5-cyano-phenoxy)-2-fluoro-phenyl]-acetamide; compound with hydrochloric acid (I-153)

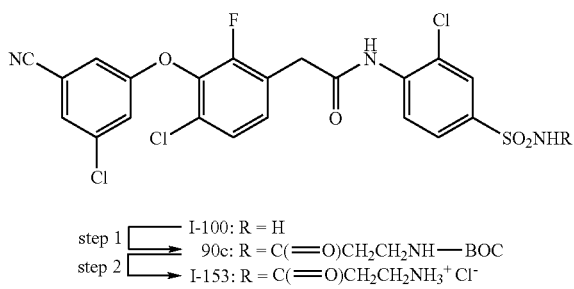

step 1 — To a solution of I-100 (0.100 g, 0.189 mmol) and Boc-β-alanine (0.05 g, 0.264 mmol) and DCM (10 mL) was added EDCI hydrochloride (0.04 g, 0.21 mmol) and DMAP (0.01 g, 0.09 mmol). The reaction was stirred at RT for 2 h. The reaction mixture was cooled to 0° C. and 25 mL of ice was added. The reaction mixture was allowed to warm to RT and extracted with DCM. The organic extracts were washed sequentially with 10% HCl, water and brine. The DCM solution was dried (Na$_2$SO$_4$), filtered and evaporated in vacuo. The solid was purified by recrystallization with EtOAc/acetone to afford 90c.

step 2 — 90c was dissolved in Et$_2$O (10 mL) and 1 N HCl (10 mL) was added and the reaction stirred until deprotection of the BOC protecting group was compete. The solvents were evaporated in vacuo and the resulting solid triturated in toluene to afford I-153.

Compound I-77 was prepared in the same manner except 2-[4-chloro-3-(3-chloro-5-cyano-phenoxy)-2-fluoro-phenyl]-N-(2-methyl4-sulfamoyl-phenyl)-acetamide (I-42) replaced I-100 and BOC-NH-Val-OH replaced BOC-β-Ala.

Compound I-127 was prepared in the same manner except BOC-NH-Val-OH replaced BOC-β-Ala.

Compound I-181 was prepared in the same manner except 2-[4-chloro-3-(3-chloro-5-cyano-phenoxy)-2-fluoro-phenyl]-N-(2-chloro4-methylsulfamoyl-phenyl)-acetamide (1-168) replaced I-100.

EXAMPLE 33

2-[4-Chloro-3-(3-chloro-5-cyano-phenoxy)-2-fluoro-phenyl]-N-(2-chloro4-pentanoysulfamoyl-phenyl)-acetamide; sodium salt (I-173)

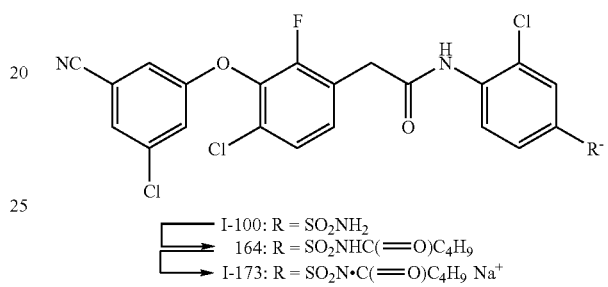

To a solution of the sulfonamide I-100 (0.166 g, 0.314 mmol), THF (2 mL) and DCE (2 mL) was added valeric anhydride (0.064 g, 0.345 mmol) followed by a single crystal of DMAP. The solution was stirred for 24 h and partitioned between water and DCM. The organic phase was washed sequentially with 10% HCl, water and brine. The organic phase was dried (Na$_2$SO$_4$), filtered and the solvents removed in vacuo. The residue was triturated with Et$_2$O and filtered to afford 2-[4-chloro-3-(3-chloro-5-cyano-phenoxy)-2-fluoro-phenyl]-N-(2-chloro4-pentanoylsulfamoyl-phenyl)-acetamide (164).

The acyl sulfonamide 164 was suspended in THF and stirred until the solution was homogenous. To the solution cooled to 0° C. was added 1 equivalent of 1 M NaOH. The reaction was stirred for 10 min then allowed to warm to RT and the solvents were removed in vacuo. The resulting material was triturated with Et$_2$O and EtOAc to afford I-173 as a crystalline solid which was dried at 100° C. for 24 h.

Compound I-51 was prepared in the same manner except 2-[4-chloro-3-(3-chloro-5-cyano-phenoxy)-2-fluoro-phenyl]-N-(2-methyl4-sulfamoyl-phenyl)-acetamide (I-42) replaced I-100 and propionic anhydride replaced valeric anhydride.

Compound I-87 was prepared in the same manner except 2-[4-chloro-3-(3-chloro-5-cyano-phenoxy)-2-fluoro-phenyl]-N-(2-methyl4-sulfamoyl-phenyl)-acetamide (I-42) replaced I-100 and nicotinoyl chloride hydrochloride replaced valeric anhydride. The compound was isolated as the hydrochloride salt rather then as a sodium salt.

Compound I-99 was prepared by alkylation of the sodium salt of I-126 in DMF. Sodium salts of the acylsulfonamides are prepared by adding 1 equivalent of aqueous NaOH to a THF solution of I-99 and evaporating the solvent.

Compound I-126 was prepared in the same manner except valeric anhydride was replaced with propionic anhydride.

Compound I-138 was prepared in the same manner except valeric anhydride was replaced with butyric anhydride.

Compound I-139 was prepared by alkylation of the sodium salt I-138 with methyl iodide in DMF.

Compound I-155 was prepared in the same manner except I-100 methoxyacetic acid replaced valeric anhydride. The EDIC coupling from the previous procedure was used.

Compound I-156 was prepared in the same manner except acetoxyacetyl chloride replaced valeric anhydride and the acetoxy ester was subsequently cleaved by basic hydrolysis.

Compound I-162 was prepared by alkylation of the sodium salt of I-126 with methyl iodide in DMF.

Compound I-171 was prepared by alkylation of the sodium salt of I-155 with methyl iodide in DMF.

Compound I-172 was prepared by alkylation of the sodium salt of I-164 with methyl iodide in DMF.

Compound I-174 was prepared in the same manner except isovaleric acid replaced valeric anhydride. The EDIC coupling from the previous procedure was used.

Compound I-175 was prepared in the same manner except N,N-diethylglycine hydrochloride replaced valeric anhydride. The EDIC coupling from the previous procedure was used.

Compound I-176 was prepared in the same manner except 4-methylvaleric acid replaced valeric anhydride. The EDIC coupling from the previous procedure was used.

Compound I-177 was prepared in the same manner except morpholin4-yl-acetic acid replaced valeric anhydride. The EDIC coupling from the previous procedure was used.

Compound I-188 was prepared in the same manner except succinic acid replaced valeric anhydride.

EXAMPLE 34

2-[4-Chloro-3-(3,5-dicyano-phenoxy)-2-fluoro-phenyl]-N-(4-sulfamoyl-phenyl)-acetamide (I-9)

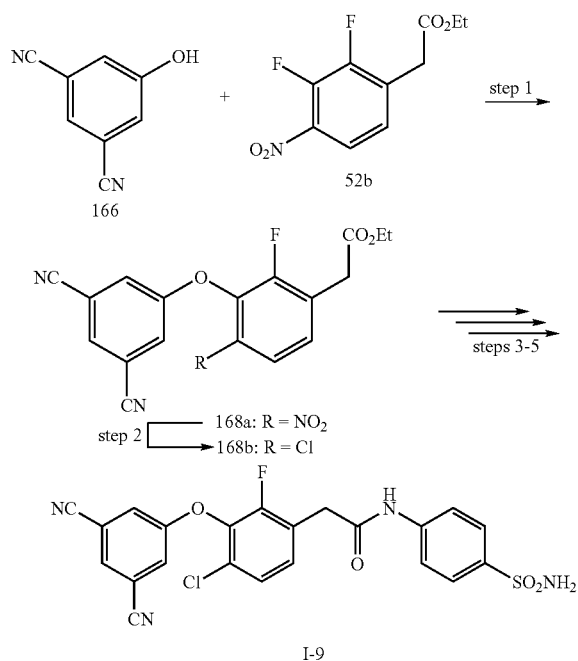

step 1
A solution of anhydrous THF (100 mL) and 5-hydroxy-isophthalonitrile (166, 10.00 g, 69.38 mmol) cooled to 0° C. was treated with sodium tert-butoxide (7.34 g, 76.32 mmol). The mixture was stirred for 30 min at 0° C. then 52b (17.01, 69.38 mmol) was added and allowed to stir for an additional 3 h. The reaction was quenched with 10% aqueous HCl. The crude mixture was extracted with EtOAc and the combined extracts washed with water and brine. The organic phase was dried (Na$_2$SO$_4$) and filtered. The solvent was removed in vacuo to afford a crude oil which was purified by SiO$_2$ chromatography eluting with hexanes:EtOAc (90:10) to afford 20 g (78%) of 168a.

Introduction of the chloro substituent (step 2) was carried out as described in steps 6 and 7 of Example 31. Steps 3-5 were carried out by the procedure described in steps 7-9 of Example 1 which afforded I-9.

Compound I-28 was prepared in the same manner except in step 5 of the present example, 4-amino-3-methyl-benzenesulfonamide was replaced with 2-chlorophenylamine.

Compound I-32 was prepared in the same manner except in step 5 of the present example, 4-amino-3-methyl-benzenesulfonamide was utilized.

EXAMPLE 35

2-[4-Chloro-3-(3-cyano-5-difluoromethyl-phenoxy)-2-fluoro-phenyl]-N-(4-sulfamoyl-phenyl)-acetamide (I-13)

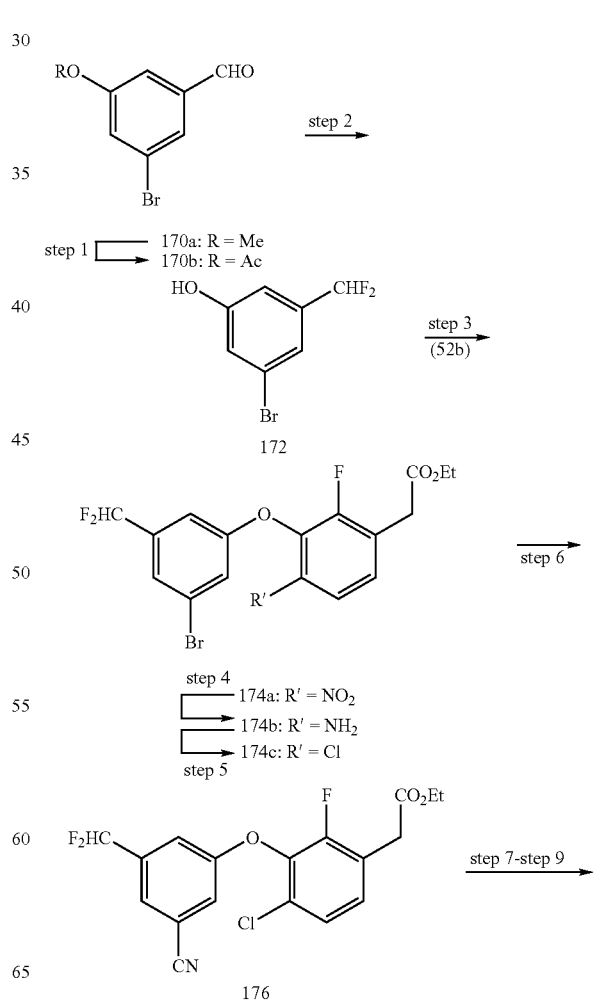

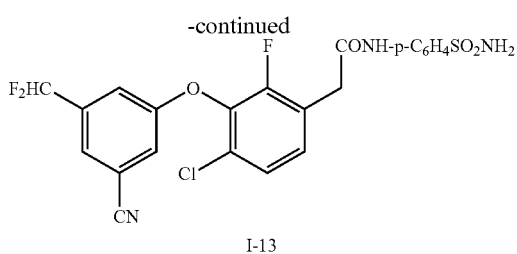

I-13 step 1—A solution of BBr$_3$ (29.1 mL of a 1.0 M solution in DCM, 29.1 mmol) was added slowly to a solution of 170a (2.5 g, 11.62 mmol) in anhydrous DCM (25 mL) maintained under N$_2$ at −78° C. The orange solution was warmed to RT, stirred for 2 h, and poured onto ice. The mixture was extracted with CH$_2$Cl$_2$ (100 mL), and the organic layer was washed with H$_2$O (50 mL) and brine (50 mL). The solvents were evaporated, and the remaining oil was purified by flash chromatography on silica gel eluting with a EtOAc/hexanes gradient (0% to 20% EtOAc) to provide the desired phenol. To a solution of this phenol in pyridine (10 mL) under argon was slowly added acetic anhydride (0.6 mL, 6.33 mmol). After 2 h, the volatile materials were removed to provide 3-bromo-5-formyl-phenyl acetate (170b, 1.02 g, 40%).

step 2—DAST (1.02 mL, 7.69 mmol) was added to a solution of the 3-bromo-5-formyl-phenyl acetate (170b, 1.1 g, 4.52 mmol) in DCM (5 mL) under nitrogen contained in a NALGENE® bottle. EtOH (0.013 mL, 0.23 mmol) was added, and the mixture was stirred for 16 h. The reaction mixture was then added slowly to an aqueous solution of saturated NaHCO$_3$. After the bubbling was finished, DCM (50 mL) was added and the layers were separated. The organic layer was washed with brine (30 mL) and dried with anhydrous MgSO$_4$. The solvent was removed to provide a yellow oil that was placed in a mixture of THF (15 mL) and H$_2$O (4 mL). LiOH monohydrate (474 mg, 11.3 mmol) was added, and the reaction mixture was stirred at RT for 2 h. The solution was then added dropwise to 5% aqueous HCl (50 mL), and the mixture was extracted with EtOAc (3×30 mL). The combined organic fractions were washed with brine (30 mL), and dried with anhydrous MgSO$_4$. Evaporation of the volatile materials gave an oil that was purified by flash chromatography on silica gel (0% to 25% EtOAc/hexanes) to provide 800 mg (79%) of 3-bromo-5-difluoromethylphenol (172).

The phenol 172 was condensed with ethyl 2,3-difluoro4-nitro-phenyl acetate (58c, step 3) as described in step 1 of Example 34. Reduction of the nitro group and diazotization and displacement of the diazonium salt by chloride (steps 4 and 5) were carried out as described in steps 6 and 7 of Example 31 to afford 174c.

step 6—A solution of 174c (757 mg, 1.73 mmol), Pd[P(Ph)$_3$]$_4$(0) (300 mg, 0.26 mmol), and zinc cyanide (122 mg, 1.04 mmol) in DMF (8 mL) under nitrogen was heated to 80° C. for 4 h. The reaction mixture was cooled to RT and added to 2 M aqueous NH$_4$OH. The solution was extracted with 1:1 EtOAc/hexanes (3×30 mL), and the combined organic fractions were washed with H$_2$O (3×20 mL) and dried (MgSO$_4$). The solvent was evaporated, and the remaining oil was purified by SiO$_2$ chromatography eluting with an EtOAc/hexanes gradient (0% to 25% EtOAc) to provide 580 mg (87%) of [4-chloro-3-(3-cyano-5-difluoromethyl-phenoxy)-2-fluoro-phenyl]-acetic acid ethyl ester (176).

steps 7-9 were carried out by the procedure described in steps 7-9 of Example 1 which afforded I-13.

Compound I-14 was prepared in the same manner except in step 9 of the present example, 2-chlorophenylamine was utilized.

Compound I-75 was prepared in the same manner except in step 9 of the present example, 4-amino-3-methyl-benzenesulfonamide was utilized.

EXAMPLE 36

2-[4-Chloro-3-(3-cyano-5-difluoromethoxy-phenoxy)-2-fluoro-phenyl]-N-(4-sulfamoyl-phenyl)acetamide (I-166)

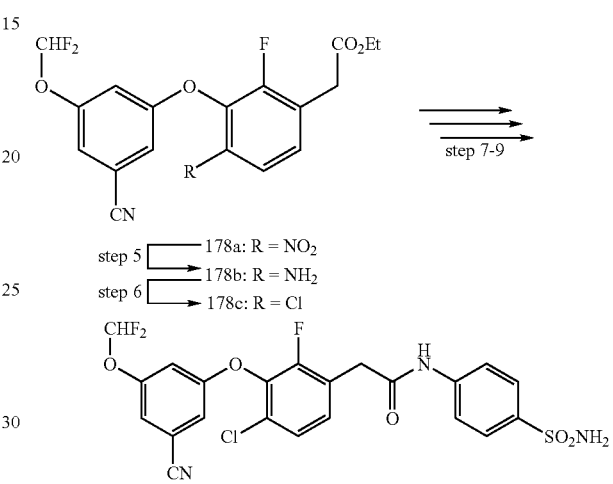

Steps 1-4 are depicted in SCHEME 10 step 1—Acetic anhydride (30 mL, 4 equiv) was added to a solution of 3,5-dihydroxybenzonitrile (84a, 10.36 g, 77 mmol) in anhydrous pyridine (60 mL) cooled to 0° C. and blanketed with nitrogen. The reaction was warmed to RT and stirred for 16 h. The volatile materials were removed in vacuo, and the remaining oil was dissolved in EtOAc, washed with water, 5% HCl solution, brine, and dried (MgSO$_4$). The volatile materials were removed to afford 14.5 g (86%) of the diacetate. The diacetate (14 g, 64 mmol) was dissolved in a mixture of EtOH (100 mL) and benzene (100 mL) and cooled to 0° C. A solution of KOH (3.6 g, 1 equiv) in EtOH was added dropwise. After 1 h, the solution was added to an ice-cold solution of saturated ammonium chloride, extracted with ether, and washed with brine. The Et$_2$O extracts were concentrated and purified by SiO$_2$ chromatography eluting with a hexane/EtOAc gradient (0% to 25% EtOAc) which afforded 10 g (88%) of 84b.

step 2—(2-Trimethylsilyl-ethoxy)-methyl-chloride (2.2 mL, 1.1 equiv) was added to a solution of the 84b (2.0 g, 11.3 mmol) and DIPEA (2.4 mL, 1.2 equiv) in DCM (50 mL) cooled to 0° C. The solution was warmed to RT, stirred for 16 h, and poured into a saturated sodium bicarbonate solution. The aqueous solution was extracted with DCM, and the combined organic extracts washed with water and brine and dried (MgSO$_4$). The solvents were removed in vacuo and the acetylated product was dissolved in a mixture of water (8 mL) and THF (32 mL). LiOH.H$_2$O (0.71 g, 1.5 equiv) was added. The mixture was stirred for 2 h, acidified to pH 5 and extracted with ether. The organic layer was dried (MgSO$_4$) and evaporated to provide 2.5 g (80%) of the 84c.

step 3—F$_2$ClCCO$_2$Na (2.84 g, 2.3 equiv) was added to a solution of Cs$_2$CO$_3$ (3.69 g, 1.4 equiv), 84b (2.26 g, 8.09 mmol), DMF (32 mL) and water (2 mL). The solution was heated to 100° C. for 2 h, cooled to RT, and poured into a solution of ammonium chloride. The solution was extracted with a mixture of EtOAc and hexanes, and the organic layer was washed with brine and dried (MgSO₄). The crude product was purified by SiO₂ chromatography eluting with a EtOAc/hexane gradient (0% to 10%) which afforded 1.83 g (70%) of 86a. The difluoromethyl ether 86a was dissolved in MeOH (30 mL), and 5.6 mL of a 1.0 M solution of HCl was added. The solution was heated to 50° C. for 5 h, and stirred at RT for 16 h. The volatile materials were evaporated, and the aqueous residue was partitioned between DCM and water. The aqueous layer was extracted with DCM, and the combined extracts were washed with water and brine. The volatile materials were removed in vacuo to afford 780 mg (73%) of 86b.

step 4—Potassium t-butoxide (4.29 mL of a 1 M solution, 1 equiv) was added to a solution of 86b (795 mg, 4.3 mmol) in THF (10 mL) cooled to 0° C. under nitrogen atmosphere. The solution was stirred for 10 min, and a solution of the 52b (1.05 g, 1 equiv) in THF (8 mL) was added dropwise. The solution was warmed to RT, stirred overnight, and poured into a saturated ammonium chloride solution. The mixture was extracted with EtOAc, washed with water and brine and dried (MgSO₄). The solvents were evaporated and the crude product purified by SiO₂ chromatography elution with an EtOAc/hexane gradient (0% to 25%) to afford 1.6 g (93%) of 178a.

step 5—A solution of 178a (1.59 g, 3.98 mmol), iron filings (0.93 g, 4.2 equiv), NH₄Cl (0.89 g, 4.2 equiv) in EtOH (25 mL) and water (15 mL) was heated to reflux for 4 h. The solution was cooled, diluted with methylene chloride, and filtered through a pad of SiO₂. Evaporation of the volatile materials afforded 1.43 g (94%) of 178b.

step 6—A solution of the 178b (1.43 g, 3.76 mmol) in dry MeCN(15 mL) was added slowly to a rapidly stirred solution of CuCl₂ (1.01 g, 2 equiv) and tert-butyl nitrite (0.89 mL of a 90% solution, 1.8 equiv) that had been heated to 60 C. under a N₂ atmosphere. After 1 h, the reaction was cooled to RT, and 5 mL of 5% HCl was added. The solution was partitioned between EtOAc and brine. The organic extracts were dried (MgSO₄), filtered and concentrated in vacuo. The crude product was purified by SiO₂ chromatography and eluted with an EtOAc/hexane gradient (0% to 35%) to afford 1.04 g (69%) of 178c.

steps 7 to 9 were carried out as described in steps 7-9 of Example 1 to afford I-166.

Compound I-167 was prepared in the same manner except in step 9 of the present example, 4-amino-3-chloro-benzene-sulfonamide replaced 4-amino-benzenesulfonamide.

EXAMPLE 37

2-{4-Chloro-3-[3-cyano-5-(1,1-difluoro-ethyl)-phenoxy]-2-fluoro-phenyl}-N-(4-sulfamoyl-phenyl)-acetamide (I-95)

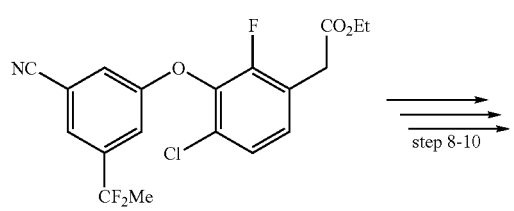

76

-continued

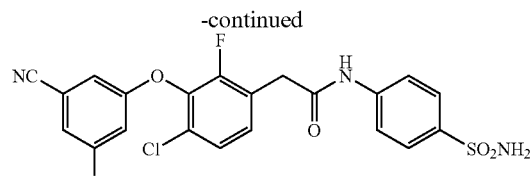

I-96

Steps 1-7 are depicted in reacti-on C of SCHEME 8 step 1—n-BuLi (13.4 mL of a 1.6 M solution, 1.1 equiv) was added slowly to a solution of the tert-butyl-(3,5-dibromo-phenoxy)-dimethyl-silane (70, 7.16 g, 19.5 mmol) in Et₂O (60 mL) cooled to −78° C. under a blanket of N2. The solution was stirred for 25 min, and N-methoxy-N-methyl-acetamide was added via syringe. The solution was warmed slowly to RT, added to saturated ammonium chloride, and extracted with ether. The combined organic layers were washed with brine and dried (MgSO₄), filtered and concentrated in vacuo. The crude product material was dissolved in THF (50 mL), and a solution of Bu₄NF (approximately 1.2 equiv) Was added. The solution was stirred for 2 h and partitioned between EtOAc and brine. The organic layer was washed with water, brine, and dried (MgSO₄) to afford 3.35 g (80%) of 72a.

step 2—Acetic anhydride (1.1 mL, 1.2 equiv) was added to a solution of the 72a (2.0 g, 9.3 mmol) in pyridine (30 mL) cooled to 0° C. The solution was warmed to RT, stirred for 2h, and the volatile materials were removed in vacuo. The residue was dissolved in ether, and washed with 5% HCl solution, water, brine, and dried (MgSO4). The solvents were evaporated to afford 2.3 g (98%) of 72b.

step 3—A suspension of 72b (2.35 g, 9.1 mmol) and Deoxy-Fluore® (2.9 mL, 1.7 equiv) (Caution: EXPLOSIVE REAGENT) under N₂ atmosphere in a Teflon bottle was heated to 85° C. The solution was stirred for 20 h at 85° C. then for 24 h at RT. The resulting solution was added slowly to a cooled solution of saturated NaHCO₃. The aqueous solution was extracted with DCM, and the organic layer was washed with brine. Evaporation of the volatile materials afforded crude 72c which was dissolved in THF (22 mL) and water (6 mL). LiOH.H₂O (1.12 g, ca. 3 equiv) was added, and the solution was stirred for 2 h. The mixture was then poured into a 5% HCl aqueous solution, extracted with ether, and the organic layer was washed with brine. Evaporation of the volatile solvents afforded the crude residue which was purified by SiO₂ chromatography eluting with an EtOAc/hexane gradient (3% to 10%) which afforded 0.95 g (44%) of 72c.

steps 4 to 6 were carried out by the procedure described in steps 4 and 6 of example 36 to afford 74c.

step 7—A solution of the 74c (0.78 g, 1.73 mmol), Zn(CN)₂ (0.12 g, 0.6 equiv), and (Ph₃P)₄P (0.30 g, 0.15 equiv) in DMF (7 mL) was heated to 80° C. for 4 h. The solution was cooled, added to 2 M ammonium hydroxide solution and extracted with ether. The organic extract was washed with brine and dried (MgSO₄) and concentrated in vacuo. The crude product was purified by SiO₂ chromatography eluting with a EtOAc/hexane gradient (0% to 25%) to afford 0.55 g (80%) of 76.

steps 8 to 10 were carried out as described in steps 7-9 of the example 1 to afford I-95.

Compound I-96 was prepared in the same manner except in step 10 of the present example, 4-amino-3-methyl-benzene-sulfonamide replaced 4-amino-benzenesulfonamide.

Compound I-97 was prepared in the same manner except in step 10 of the present example, 4-amino-3-chloro-benzenesulfonamnide replaced 4-amino-benzenesulfonamide.

EXAMPLE 38

2-[3-(3-Bromo-5-cyano-phenoxy)4-chloro-2-fluoro-phenyl]-N-(2-methyl4-sulfamoyl-phenyl)-acetamide (I-185)

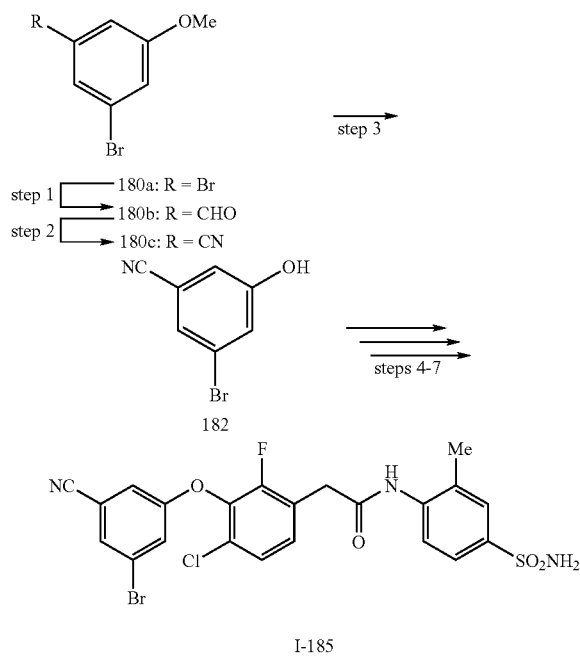

step 1—n-BuLi (2.6 mL of a 1.6 M solution, 1.1 equiv) was added slowly to a solution of the 180a (1.0 g, 3.8 mmol) in Et$_2$O (20 mL) cooled to −78° C. under an N$_2$ atmosphere. The solution was stirred for 45 min, and DMF was added via syringe. The solution was warmed slowly to RT, added to saturated ammonium chloride, and extracted with ether. The organic phase was washed with brine and dried (MgSO$_4$), filtered and evaporated to afford 0.80 g (98%) of 180b.

step 2—A solution of the aldehyde 180b (12.0 g, 56 mmol), hydroxylamine hydrochloride (19.4 g, 5 equiv), EtOH (100 mL) and pyridine (10 mL) was heated to 65° C. for 16 h. The mixture was cooled to RT, and partitioned between 50% EtOAc/hexanes and water. The organic layer was washed with brine and dried (MgSO$_4$). The volatile materials were evaporated to afford 12.4 g (97%) of the oxime. This material was dissolved in anhydrous dioxane (100 mL) and pyridine (26 mL, 6 equiv). The solution was cooled to 0° C., TFAA (15 mL, 2 equiv) was added, and the mixture was allowed to warm to RT. The solution was stirred for 2 d, and warmed to 60 C for 1 h. The mixture was cooled to RT, and added carefully to ice water. The mixture was extracted with methylene chloride, and the combined organic layers were washed with water, 1 M HCl, and brine. The organic layer was dried (MgSO$_4$) and evaporated to afford 10.4 g (90%) of 180c.

step 3—Anhydrous collidine (100 mL) was added to a dry flask containing 180c (10.4 g, 49 mmol) and LiI (19.6 g, 3 equiv). The solution was heated under nitrogen to 150° C. overnight, cooled to RT, and poured into an ice cold 1 M HCl solution. The mixture was extracted with a 1:1 EtOAc/hexanes solution, washed with water, and dried (MgSO$_4$). Concentration in vacuo afforded 8.7 g (89%) of 182.

step 4—The condensation of 182 and 52b was carried out as described in step 4 of example 36. Steps 5 to 7 were carried out as described in steps 7 to 9 of example 1 except in the present case 4-amino-3-methyl-benzensulfonamide replaced 4-amino-benzenesulfonamide.

EXAMPLE 39

2-[4-Bromo-3-(3-chloro-5-cyano-phenoxy)-2-fluoro-phenyl]-N-(2-chloro4-sulfamoyl-phenyl)-acetamide (I-189)

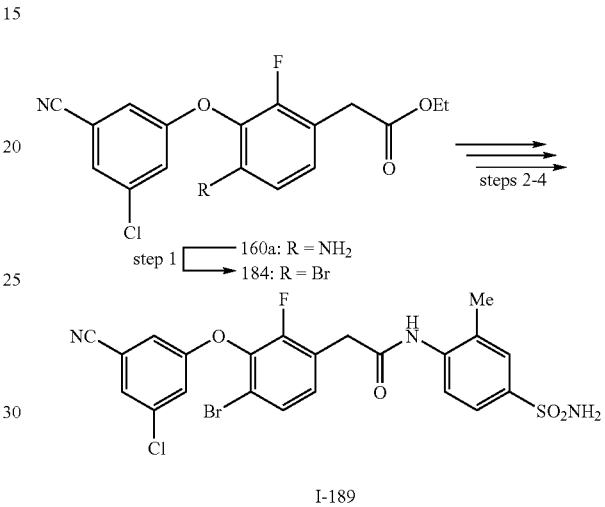

The phenyl acetic acid 160a was prepared as described in steps 1-6 of example 31 step 1—A 150 mL three-neck round bottom flask was charged with MeCN (50 mL), CuBr (2.8 g, 12.61 mmol) and t-butyl nitrite (1.4 g, 13.76 mmol), degassed and maintained under an Ar atmosphere and heated to 70° C. To the mixture was added dropwise a solution of 160a (4.0 g, 11.47 mmol) dissolved MeCN (20 mL). The reaction mixture was stirred at 70° C. for 4 h and then cooled to 0° C. The reaction was quenched by addition of 10% HCl (30 mL) and extracted with EtOAc. The combined extracts were sequentially washed with 10% HCl and brine. The organic extract was dried (Na$_2$SO$_4$), filtered and the volatile solvents removed in vacuo to yield a black oil which was purified by flash chromatography on silica gel (hexanes:EtOAc 95:5) to afford 2.5 g (52.8% theory) of 184.

steps 2 and 4 were carried out as described steps 7 and 8 of Example 1.

step 5—A 100 mL round bottom flask was charged with 4-amino-3-methyl-benzenesulfonamide (0.092 g, 0.495 mmol), dissolved in 2 mL of acetone and NaHCO$_3$ (0.040 g, 0.495 mmol) was added. To the stirred suspension under a nitrogen atmosphere was added dropwise a solution of the acid chloride from step 4 (0.200 g, 0.495 mmol) dissolved in 3 mL acetone and the reaction was stirred for 24 h at RT. The reaction mixture was cooled to 0° C. and quenched with 10% aqueous HCl. The aqueous phase was extracted with EtOAc and the combined extracts were washed with aqueous 10% HCl, water, and brine. The organic phase was dried over (Na$_2$SO$_4$), filtered and the solvent was removed in vacuo. The crude product was purified by SiO$_2$ chromatography eluting with DCM/MeOH (93:7) to afford 0.240 g (87%) of I-189: ms (M–H)=551, mp 244.0-245.1, CHN; calcd C, 47.80; H, 2.92; N, 7.60; found C, 47.51; H, 2.80; N, 7.49.

EXAMPLE 40

2-[4-Bromo-3-(3-cyano-5-difluoromethyl-phenoxy)-2-fluoro-phenyl]-N-(2-chloro4-sulfamoyl-phenyl)-acetamide (I-169)

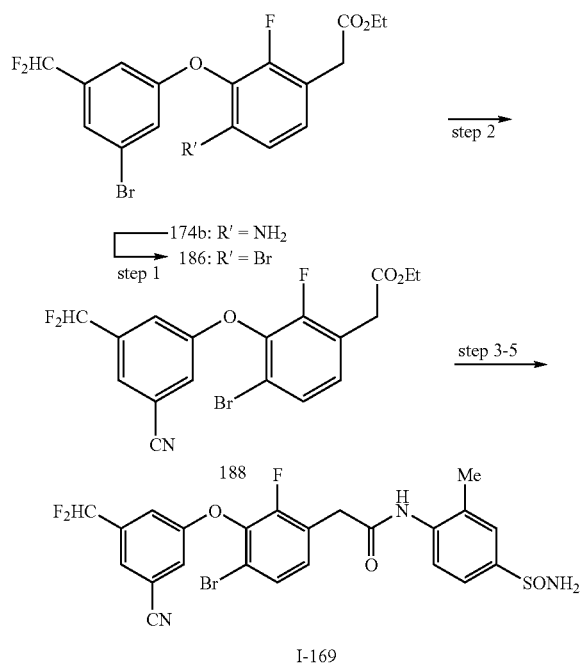

Step 1 was carried out by the procedure described in step 1 of example 39. Step 2 was carried out by the procedure described in step 7 of example 37. Steps 3 to 5 were carried out by the procedures described in steps 7 to 9 of Example 1 except in step 9, 4-amino-benzenesulfonamide was replaced by 4-amino-3-methyl-bezenesulfonamide which afforded in I-169.

EXAMPLE 41

2-[3-(3-Cyano-5-difluoromethyl-phenoxy)-2-fluoro4-methyl-phenyl]-N-(2-methyl4-sulfamoyl-phenyl)-acetamide (I-85) and 2-[3-(3-Cyano-5-difluoromethyl-phenoxy)4-ethyl-2-fluoro-phenyl]-N-(2-methyl4-sulfamoyl-phenyl)-acetamide (I-180)

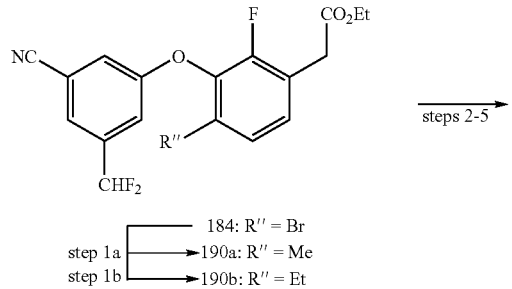

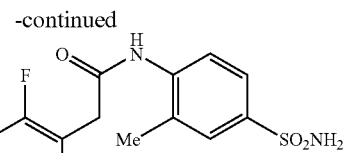

I-85: R″ = Me
I-180: R″ = Et step 1a—To a degassed ice-cold solution of THF (15 mL), Pd(dppf)Cl$_2$ (0.09 g, 0.121 mmol) was added DIBAL-H (0.012 mmol; 1M in toluene). The reaction mixture was allowed to warm to RT. A solution of 184 (1.0 g, 2.42 mmol) was added followed by Me$_2$Zn (1 M in THF, 4.240 mmol). The reaction was heated to 65° C. for 4 h, cooled to RT and quenched with aqueous NH$_4$Cl. The resulting mixture was extracted with EtOAc and washed sequentially with NH$_4$Cl and brine. The EtOAc extract was dried (Na$_2$SO$_4$), filtered and the volatile solvent removed in vacuo to yield a dark brown oil that was purified by flash chromatography on silica gel eluting with hexanes:EtOAc (95:5) to yield 190a (0.50 g, 59% theory)

step 1b—190b was prepared by a procedure identical to that described in step 1a except Me$_2$Zn was replaced with Et$_2$Zn. The product was purified by flash chromatography on silica gel eluting with hexanes:EtOAc (95:5) to afford 0.62 g (74%) of 190b.

I-85 and I-180 were prepared from 190a and 190b respectively following the procedure described in steps 7-9 of example 1 except in step 5 of the present example 4-amino-benzenesulfonamide was replaced by 4-amino-3-methyl-bezenesulfonamide.

Compound I-84 was prepared in the same manner from I-190a except in step 5 of the present, example 4-amino-benzenesulfonamide was replaced by 4-amino-3-chloro-bezenesulfonamide. The crude product recrystallized from EtOAc/hexane to afford 0.182 g (28%) of I-84: MS: (M–H)=522, mp. 218.0-218.7, Elemental Analysis Found: C: 52.54; 3.04; 7.99.

Compound I-86 was prepared in the same manner from I-190a except in step 5 of the present example, 4-amino-benzenesulfonamide was replaced by 2-chloro-phenylamine.

Compound I-110 was prepared in the same manner from I-190a except in step 5 of the present, example 4-amino-benzenesulfonamide was replaced by methyl 4-amino-3-chloro-benzoate and in a subsequent step the benzoic acid methyl ester was converted to the corresponding benzoic acid present in I-110.

Compound I-112 was prepared in the same manner except in step 8 of the present example, 4-amino-3-chloro-benzenesulfonamide was replaced with 2-chloro4-methanesulfonyl-phenylamine.

EXAMPLE 42

2-[3-(3-Chloro-5-cyano-phenoxy)-2-fluoro4-methyl-phenyl]-N-(2-chloro4-sulfamoyl-phenyl)-acetamide (I-83)

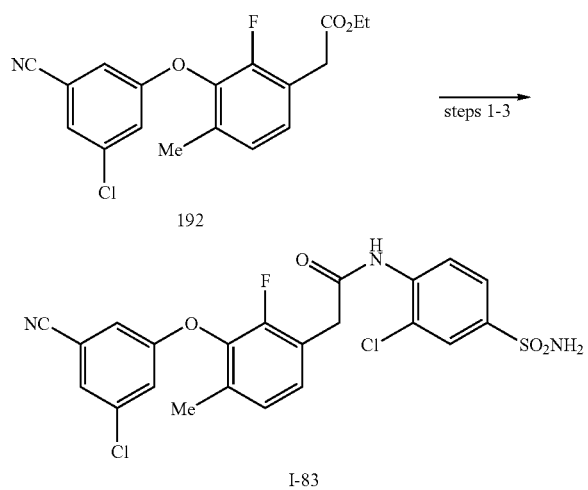

[3-(3-Chloro-5-cyano-phenoxy)-2-fluoro4-methyl-phenyl]-acetic acid ethyl ester (192) was prepared from 160 (example 31) by reduction of the nitro group followed by the diazotization/bromination and Negishi methylation of 160 as described in step 1a of example 41.

Steps 1-3 of the present example were carried out as described in steps 7 to 9 of example 1 except in the present example 4-amino-benzenesulfonamide was replaced by 4-amino-3-chloro-benzenesulfonamide to afford I-83.

EXAMPLE 43

2-[3-(3-Chloro-5-cyano-phenoxy)-2-fluoro4-methoxy-phenyl]-N-(2-chloro4-sulfamoyl-phenyl)-acetamide (I-190)

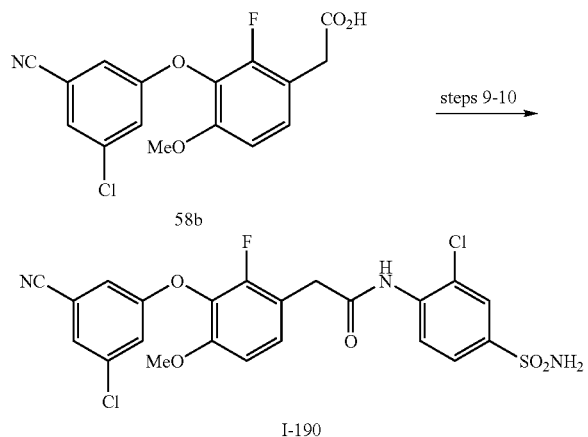

See SCHEME 7 for steps 1 to 8.

step 1—To a solution of di-iso-propylamine (150 mL, 108.3 g, 1.07 mol) in THF (500 mL) cooled to −78° C. and maintained under a $N_2$ atmosphere was added over 1 15 min period, n-BuLi (100 mL, 1.00 mol, 10 M in hexanes). The resulting mixture was stirred for 30 min at −78° C. A mixture of 54a (45 mL, 52.110 g, 0.457 mol) and chlorotrimethylsilane (130.0 1L, 111.28 g, 1.024 mol) was added at a rate which maintained the internal reaction temperature below −50° C. The solution was stirred at −78° C. for 1 h. The reaction was quenched at −78° C. by addition of 1 M $H_2SO_4$, diluted with MTBE and the mixture was saturated with solid NaCl. The phases were separated and the aqueous phase was extracted with MTBE (300 mL). The combined organic extracts were dried ($MgSO_4$), filtered and the solvents evaporated to afford 118 g (100%) of 54b as a white solid.

step 2—To neat bromine (76.9 mL, 1.50 mol) cooled to 0° C. in an ice bath was added portion wise solid 54b (126.23 g, 0.500 mol) while maintaining the internal temperature between 20-45° C. (caution: exothermic!). The reaction mixture was stirred at 58° C. for 2 h. After 1 h of this period had elapsed additional bromine (45.48 g) was added and the addition funnel was rinse with cyclohexane (10 mL). The reaction mixture was cooled to 0° C. and slowly poured into ice-cold saturated $NaHSO_3$ solution. After the addition the resulting mixture was saturated with solid NaCl, extracted with MTBE (500 mL and 200 mL), dried ($MgSO_4$) and concentrated in vacuo to afford 191 g of 54c. The reaction mixture was distilled at ca. 60 mbar which afforded 161.53 g of colorless liquid which boiled at 110° C. and contained about 11% of the monobromo derivative. The product was redistilled through a bubble ball column at ca. 50 mbar which afforded 141.3 (78.5%) of 54c with a boiling point of 93-94° C. which was >99.6 pure.

step 3—Preparation of iso-PrMgCl.LiCl—A sample of LiCl (4.56 g, 107.6 mmol) was dried under high vacuum with a heat gun for 10 min. To the dry solid under a $N_2$ atmosphere at 23° C. was added iso-PrMgCl (53.8 mL, 107.6 mmol, 2M solution in THF) and the resulting mixture was stirred at 23° C. for 3 days.

To a solution of 54c (1.29 mL, 10 mmol) in THF (5 mL) at −40° C. was added the iso-PrMgCl.LiCl solution (5.5 mL, 11 mmol, 2.0 M in THF) at a rate that maintained the reaction temperature below −30° C. Stirring was continued at −35 to −30° C. for 1 h then warmed to −7° C. for an additional 1 h. The reaction mixture was cooled to −30° C. and DMF (1.00 mL, 13 mmol) was added in one portion (temperature rose to −23° C.) and stirring continued for 3.5 h at −25 to +15° C. The reaction mixture was poured into 1 M $H_2SO_4$ and ice and the resulting mixture was saturated with solid NaCl and twice extracted with MTBE.

The combined extracts were dried ($MgSO_4$), filtered and concentrated in vacuo to afford 2.17 g (98%) of 54d as a white solid.

step 4—To a solution of 3-chloro-5-hydroxy-benzonitrile (3.84 g), $K_2CO_3$ powder (4.2 g) and n-butyl nitrile was added 54d (5.57 g). The reaction mixture was heated to reflux for 4.5 h when the reaction appeared complete by gc/ms. The reaction mixture was cooled, poured into water and EtOAc was added. The resulting mixture was allowed to stand until the layers separated. Some crystals were present at the interface and along the walls of the upper layer which were filtered and washed with water and hexanes. The filtrate was evaporated in vacuo, the residue taken up in IPA and re-evaporated. The solid was triturated with hexane and filtered. The mother liquor was evaporated and the residue purified by $SiO_2$ chromatography eluting with hexane/EtOAc (80:20). The product was triturated with IPA, filtered and washed with hexanes and the product fractions combined to afford 1.45 g (83%) of 56a.

step 5—Trifluoroacetic anhydride (8.88, 4.231 mmol) was added to a 100 mL round bottom and stirred at 0° C. 30% Hydrogen peroxide (0.290, 8.46 mmol) was then added dropwise to the reaction vessel and stirred for 2 hours at zero to produce trifluoroperacetic acid (TFPA).

To a solution of 56a (2.0, 5.64 mmol) in DCM (20 mL) stirred at 0° C. was added $KH_2PO_4$ (15.35 g, 112.82 mmol). To this suspension was added dropwise at 0° C. the TFPA. The reaction was stirred for 48 h. Upon consumption of starting material reaction mixture was cooled to 0° C., and diluted with brine, and quenched with aqueous 10% sodium bisulfite. The resulting mixture was extracted with DCM and washed with brine, dried ($Na_2SO_4$), filtered and the solvent removed in vacuo to yield a yellow solid which was purified by $SiO_2$ chromatography eluting with hexane/EtOAc (92:8) to afford 1.8 g (94%) of 56b.

step 6—To a solution of 56b (1.8 g, 5.26 mmol) in DMF (15 mL) was added $Cs_2CO_3$ (3.43, 10.52 mmol) and iodomethane (0.74 g, 5.26 mmol). The reaction mixture was stirred at 85° C. for 12 h. When 56b was consumed, the reaction mixture was cooled to RT and the cured mixture extracted with EtOAc and the combined extracts washed with water and brine. The EtOAc was dried ($Na_2SO_4$), filtered and concentrated in vacuo to afford 56c as a yellow oil which was used in the next step without additional purification.

step 7—A dry 100 mL round bottom was purged with nitrogen and charged with 56c (1.6 g, 4.50 mmol) and anhydrous THF (20 mL). The mixture was cooled to −20° C. and a solution of iso-PrMgCl—LiCl (5.40 ml, 5.40 mol, 2 M in THF, see step 3) was added dropwise. The reaction was stirred for 2 h at −20° C. and a solution of CuCN LiCl (0.100 mL, 0.100 mol 1 M in THF) was added and stirred continued at −20° C. To this mixture was added allyl bromide (1.08 g, 9.0 mmol) and the mixture stirred for an additional two h. The reaction was quenched by addition of aqueous $NH_4Cl$. The mixture extracted with EtOAc and washed with water and brine. The extracts were dried ($Na_2SO_4$), filtered and the solvent was removed in vacuo to yield a yellow oil. The crude product was purified by $SiO_2$ chromatography eluting with hexane/EtOAc (95:5) to afford I g (70%) of 58a.

step 8—To a solution of 58a (0.100 g, 0.315 mmol), EtOAc (2 mL), MeCN (2 mL) and water (3 mL) was added $NaIO_4$ (0.437 g, 2.050 mmol) and $RuCl_3$ (0.001 g, 0.006 mmol). When 58a was consumed, the crude mixture was filtered through a pad of CELITE®, washed with EtOAc and the combined EtOAc washes were washed with brine, dried ($Na_2SO_4$) filtered and evaporated in vacuo to afford 0.090 g (85%) of 58b as a yellow solid. extracted with ethyl acetate, and washed with brine. The ethyl acetate was dried over sodium sulfate and filtered. Solvent was removed in vacuo to yield 58b as a yellow solid (0.090 g, 85%).

step 9 and 10 were carried as described in steps 8 and 9 of Example 1 except in step 9, 4-amino-3-methyl-benzene-sulfonamide was replaced by 4-amino-3-chloro-benzene-sulfonamide to afford I-190.

Compound I-191 was made by a similar procedure except in step 10, 4-amino-3-chloro-benzenesulfonamide was replaced by 4-amino-3-chloro-benzenesulfonamide

EXAMPLE 44

2-[3-(2-Chloro-5-cyano-phenoxy)-5-methoxy-phenyl]-N-(4-sulfamoyl-phenyl)-acetamide (I-102)

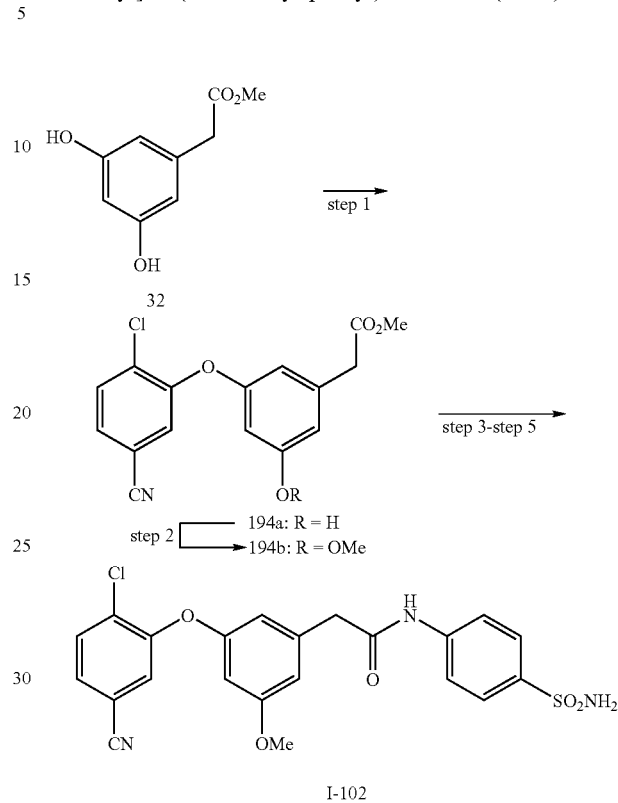

I-102 step 1—A solution of 4-chloro-3-fluoro-benzonitrile (5.977 g, 38.42 mmol), methyl 3,5-dihydroxy-phenylacetate (7.0 g, 38.42 mmol), $K_2CO_3$ (15.9 g, 0.115 mol) and NMP (70 mL) was stirred and heated to 120° C. for 12 h. The reaction mixture was cooled to RT and diluted with $H_2O$ (150 mL), acidified with 10% aqueous HCl and twice extracted with EtOAc. The combined organic extracts were washed sequentially with water (6 times) and brine, dried ($Na_2SO_4$), filtered and concentrated in vacuo. The crude product was purified by $SiO_2$ column chromatography eluting with a EtOAc/hexane gradient (0 to 25% EtOAc) to afford 194a.

step 2—A solution of 194a (0.500 g, 1.57 mmol), methyl iodide (196 µL, 0.447 g, 3.15 mmol), $K_2CO_3$ (0.594 g, 3.93 mmol) and NMP (5 mL) was stirred at 85° C. for 1 h. The reaction mixture was cooled to RT, diluted with $H_2O$ (25 mL) and twice extracted with EtOAc. The combined organic extracts were washed sequentially with water (6 times) and brine, dried ($Na_2SO_4$), filtered and concentrated in vacuo. The crude product was purified by $SiO_2$ column chromatography eluting with EtOAc/hexane to afford 194b.

steps 3 to 5 were carried out by the procedure described in steps 7-9 of Example 1 which afforded of I-102.

Compound I-103 was prepared using a similar procedure except in step 5 of the present example, 4-amino-benzene-sulfonamide was replaced with 4-amino-2-methyl-benzene-sulfonamide.

Compound I-113 was prepared using a similar procedure except in step 5 of the present example, 4-amino-benzene-sulfonamide was replaced with 4-amino-2-chloro-benzene-sulfonamide.

EXAMPLE 45

2-[3-(3-Chloro-5-cyano-phenoxy)-5-methoxy-phenyl]-N-(4-sulfamoyl-phenyl)-acetamide (I-132)

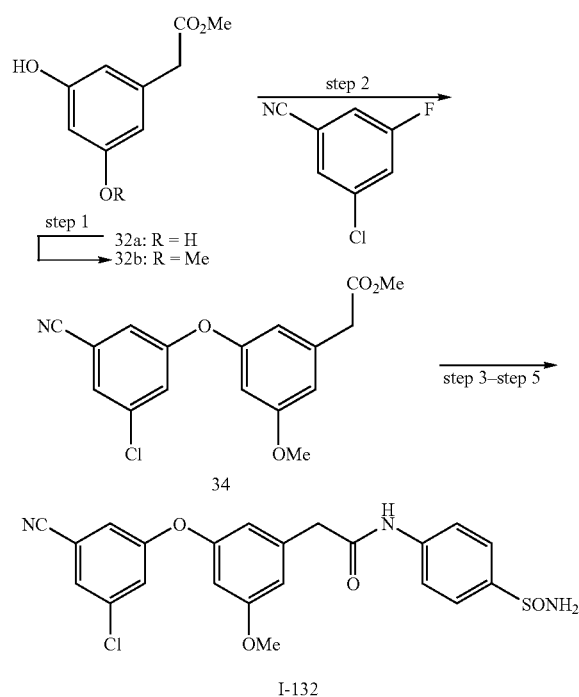

step 1—A solution of methyl iodide (10.25 mL, 23.374 g, 0.165 mol), methyl 3,5-dihydroxy-phenylacetate (32a, 30.0 g, 0.165 mol), $K_2CO_3$ (34.15 g, 0.247 mol) and NMP (300 mL) was stirred and heated to 85° C. for 2 h. An additional 5 mL of methyl iodide and 10 g of $K_2CO_3$ was added and stirred for an additional 2 h. The reaction mixture was cooled to RT and diluted with $H_2O$ (150 mL), acidified with 10% aqueous HCl and twice extracted with EtOAc. The combined organic extracts were washed sequentially with water (6 times) and brine, dried ($Na_2SO_4$), filtered and concentrated in vacuo. The crude product was purified by $SiO_2$ column chromatography eluting with a EtOAc/hexane gradient (0 to 25% EtOAc) to afford 32b.

step 2—A solution of methyl 3-hydroxy-5-methoxy-phenyl acetate (32b, 0.500 g, 2.55 mmol), 3-chloro-5-fluorobenzonitrile (0.3964 g, 2.55 mmol), $K_2CO_3$ (1.057 g, 7.65 mmol) and NMP (5 mL) was stirred and heated at 120° C. for 12 h. The reaction mixture was cooled to RT and diluted with $H_2O$ (35 mL), adjusted to pH 11 with 1 N NaOH and twice extracted with EtOAc. The combined organic extracts were washed sequentially with water (6 times) and brine, dried ($Na_2SO_4$), filtered and concentrated in vacuo. The crude product was purified by $SiO_2$ column chromatography eluting with a EtOAc/hexane gradient (0 to 25% EtOAc) to afford 34.

steps 3 to 5 were carried out by the procedure described in steps 7-9 of Example 1 which afforded I-132.

Compound I-133 was prepared using a similar procedure except in step 5 of the present example, 4-amino-benzenesulfonamide was replaced with 4-amino-2-methyl-benzenesulfonamide.

Compound I-136 was prepared using a similar procedure except in step 5 of the present example, 4-amino-benzenesulfonamide was replaced with 4-amino-2-chloro-benzenesulfonamide.

EXAMPLE 46

2-[3-(3-Chloro-5-cyano-phenoxy)-5-methyl-phenyl]-N-(4-sulfamoyl-phenyl)-acetamide (I-141)

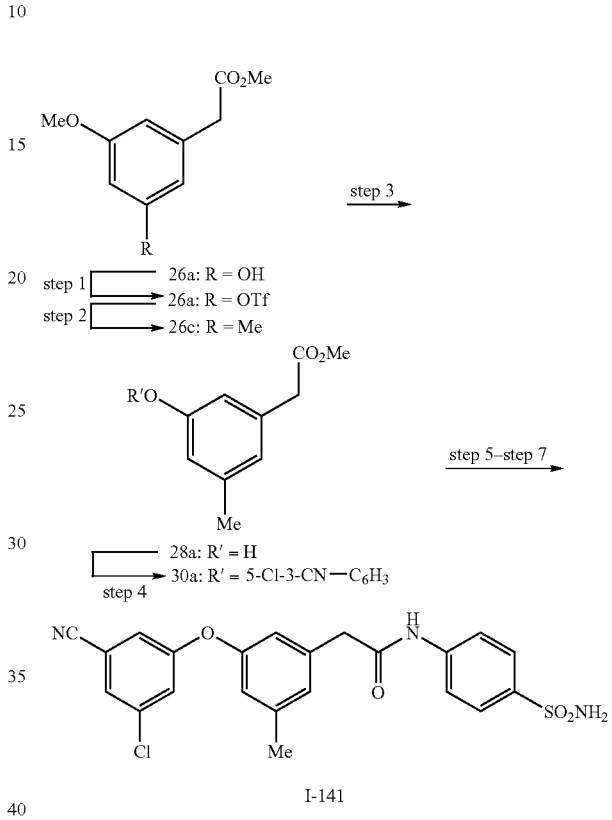

step 1—A solution of 26a (4.8 g, 024.46 mmol) was dissolved in DCM (50 mL) and pyridine (3.957 mL, 3,896 g, 48.92 mmol) was added. The reaction mixture was cooled to 0° C. and triflic anhydride (4.83 g, 7.593 g, 26.9 mmol) was added dropwise and the reaction mixture stirred for 1 h. The cold reaction mixture was transferred to a separatory funnel and washed quickly with ice-cold 1 N HCl, cold saturated bicarbonate, water and brine. The resulting DCM solution was dried ($Na_2SO_4$), filtered and the volatile solvents removed in vacuo. The resulting crude triflate 26b was used directly in step 2.

step 2—A three-neck round bottom flask was flameed and flushed with Ar. The flask was charged with Pd(dppf)$Cl_2$ (0.649 g, 7.95 mmol) and anhydrous THF (30 mL). The reaction mixture was cooled to 0° C. and DIBAL-H was added dropwise (1.1 mL, 0.2261 g, 1.59 mmol). The reaction mixture was warmed to RT and stirred for 1 h. A solution of 26a (5.22 g, 0.0159 mmol) and THF (30 mL) was added and the resulting solution was stirred at RT for 3h. $Me_2Zn$ (7.95 mL, 0.159 mmol, 2.0 M solution in toluene) was added dropwise and the reaction mixture was stirred at 50° C. for 1 h. The reaction was carefully quenched with a small quantity of water, filtered through a pad of CELITE® and the solids washed thoroughly with EtOAc. The combined organic extracts were washed with water and brine, dried ($MgSO_4$) and the solvent evaporated. The crude product was purified by SiO₂ chromatography eluting with a EtOAc/hexane gradient (0 to 25% EtOAc) to afford 26c.

step 3—The ester 26c (2.64 g, 0.136 mmol) was dissolved in DCM (20 mL) and the reaction mixture was cooled to −78° C. A solution of BBr₃ (67.96 mL, 67.96 mmol, 1.0 M in DCM) was added dropwise. After the addition was completed the reaction mixture was allowed to warm to RT and stirred for 2 h. The reaction mixture was recooled to −78° C. and the reaction quenched aqueous NaHCO₃ then warmed to RT and the organic phase washed with water, saturated NaHCO₃ and brine. The organic phase was dried (MgSO₄) and the solvent evaporated to afford 28a.

step 4—A solution of 28a (0.500 g, 2.77 mmol), 3-chloro-5-fluoro-benzonitrile (0.4316 g, 2.77 mmol), K₂CO₃ (1.150 g, 8.32 mmol) and NMP (5 mL) was stirred and heated for 8 h at 120° C. The reaction mixture was cooled to RT and diluted with H₂O (150 mL), acidified with 10% aqueous HCl and twice extracted with EtOAc. The combined organic extracts were washed sequentially with water (6 times) and brine, dried (Na₂SO₄), filtered and concentrated in vacuo. The crude product was purified by SiO₂ column chromatography eluting with EtOAc/hexane gradient (0 to 25% EtOAc) to afford 30a.

steps 5 to 7 were carried out by the procedure described in steps 7-9 of Example 1 which afforded I-141.

Compound I-142 was prepared using a similar procedure except in step 7 of the present example, 4-amino-benzenesulfonamide was replaced with 4-amino-2-methyl-benzenesulfonamide.

Compound I-143 was prepared using a similar procedure except in step 7 of the present example, 4-amino-benzenesulfonamide was replaced with 4-amino-2-chloro-benzenesulfonamide.

Compound I-146 was prepared using a similar procedure except in step 7 of the present example, 4-amino-benzenesulfonamide was replaced with 4-chloro-3-fluorobenzonitrile.

Compound I-147 was prepared using a similar procedure except in step 4 of the present example, 3-chloro-5-fluoro-benzonitrile was replaced with 4-chloro-3-fluorobenzonitrile and in step 7, 4-amino-benzenesulfonamide was replaced with 4-amino-2-methyl-benzenesulfonamide.

Compound I-148 was prepared using a similar procedure except in step 4 of the present example, 3-chloro-5-fluoro-benzonitrile was replaced with 4-chloro-3-fluorobenzonitrile and in step 7, 4-amino-benzenesulfonamide was replaced with 4-amino-2-chloro-benzenesulfonamide.

Compound I-105 was prepared using a similar procedure except in step 2 of the present example, dimethylzinc was replaced with diethylzinc to afford 26 (R=Et) and in step 4, 3-chloro-5-fluoro-benzonitrile was replaced with 4-chloro-3-fluorobenzonitrile.

Compound I-106 was prepared using a similar procedure except in step 2 of the present example, dimethylzinc was replaced with diethylzinc to afford 26 (R=Et), in step 4, 3-chloro-5-fluoro-benzonitrile was replaced with 4-chloro-3-fluorobenzonitrile and in step 7, 4-amino-benzenesulfonamide was replaced with 4-amino-2-methyl-benzenesulfonamide.

Compound I-107 was prepared using a similar procedure except in step 2 of the present example, dimethylzinc was replaced with diethylzinc to afford 26 (R=Et), in step 4, 3-chloro-5-fluoro-benzonitrile was replaced with 4-chloro-3-fluorobenzonitrile and in step 7, 4-amino-benzenesulfonamide was replaced with 4-amino-2-chloro-benzenesulfonamide.

EXAMPLE 47

2-[7-(3-Cyano-phenoxy)-benzofuran-5-yl]-N-(2-methyl-4-sulfamoyl-phenyl)-acetamide (I-145)

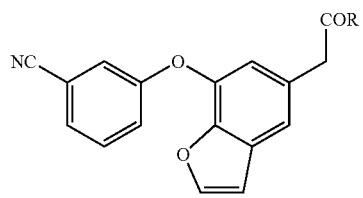

step 6 ⌈——— 105a: R = OEt
step 7 ⌊———▶ 105b: R = OH
step 8 ⌊———▶ 105c: R = Cl
       ⌊———▶ 105d: R = NH-2-Me-4-SO₂NH₂—C₆H₃ step 1—To a solution of 101a (5.0 g; 24.2 mmol; SCHEME 14) and anhydrous DCM (75 ML) was added sequentially acetyl chloride ((2.42 mL; 33.9 mmol) and SnCl₄ (5.39 mL; 46.1 mmol; 1 M solution in DCM). The reaction was stirred at RT for 50 minutes and poured into a mixture of ice and 2 N HCl (200 mL). The organic phase was separated and diluted with about 50 mL of CH₂Cl₂ and thrice washed with water (100 mL) and once with brine (100 mL). The organic phase was dried (MgSO₄), filtered and evaporated to yield 101b (6.0 g) which contained about 10% of 101a. The crude product was used without further purification.

step 2—To an ice-cold solution of 101b (6.01 g; 24.2 mmol) and DCM (100 mL) under a nitrogen atmosphere was added sequentially a solution of MCPBA (11.9 g; 48.4 mmol) and DCM (12 mL) followed by TFA (2.14 mL; 27.8 mmol). The reaction mixture was stirred at RT overnight. The reaction nixture was cooled to 0° C. and a 5% aqueous Na₂SO₃ solution (150 mL) was added slowly with stirring. The mixture was stirred for 5 minutes after addition was completed and precipitated m-chlorobenzoic acid was filtered. The solid was washed with DCM and the combined filtrates were washed with 10% NaOH (2×250 mL), 2 N HCl (200 mL), water and brine. The resulting solution was dried (MgSO₄), filtered through a pad of CELITE and concentrated in vacuo to yield 101c (4.1g).

step 3—A solution of 101c (10.3 g; 39.3 mmol), EtOH (250 mL) and saturated NaHCO₃ (100 mL) were heated to reflux for 1 h. The reaction mixture was cooled to room temperature and the EtOH removed in vacuo. Ice was added to the residue aqueous solution and the reaction carefully acidified to about pH 2 with 2 N HCl. The resulting mixture was extracted with EtOAc (2×300 mL) and the combined organic phase washed with brine, dried (Na₂SO₄), filtered and evaporated to yield a brown oil (8.8 g). The crude product was run through a silica gel column with 15% EtOAc:hexane to yield 101d (5.44g; 62.9%) as a white solid.

step 4—A dry 50 mL round bottom flask was charged with 101d (0.5 g, 2.27 mmol), 3-bromobenzonitrile (0.620 g, 3.4 mmol), Cs₂CO₃ (1.48 g, 4.54 mmol), Cu(I)Cl (0.112 g, 1.14 mmol), 2,2,6,6-tetramethyl-3,5-heptanedione (50 μL, 0.23 mmol) and NMP (10 mL). The reaction was heated at 120° C. under an Ar atmosphere for 55 h. The reaction mixture was partitioned between EtOAc and 10% aqueous HCl. The aqueous extracts were diluted with hexane and the hexane extracts were washed thoroughly with water, dried (NgSO₄), filtered and evaporated. The crude product was purified by SiO$_2$ chromatography eluting with 20% EtOAc/hexane to afford 0.373 g of 103.

step 5—To a solution of 103 (0.350 g; 1.052 mmol) and CCl$_4$ (15 mL) was added NBS (0.197 g; 1.104 mmol) and AIBN (0.0035 g). The reaction was heated at reflux for 50 min, an additional 5 mg of AIBN was added and refluxing continued for an additional 0.5 h. The reaction mixture was cooled to RT, diluted with DCM, washed with 10% NaHSO$_4$, water and brine. The resulting solution was dried, filtered and evaporated in vacuo. The crude product was purified by flash chromatography eluting with 5% EtOAc/hexane to afford 0.277 g of 105.

steps 6 to 8 were carried out by the procedure described in steps 7-9 of Example 1 except 4-amino-3-methyl-benzenesulfonamide replaced 4-amino-benzenesulfonamide which 1-145.

Compound I-144 was prepared using a similar procedure except in step 8 of the present example, 4-amino-2-methyl-benzenesulfonamide was replaced with 4-amino-benzene-sulfonamide.

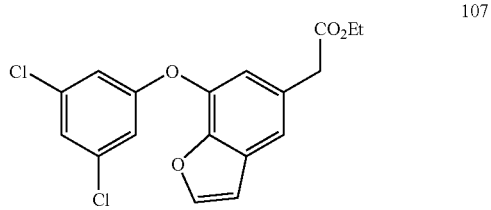

107

Compound I-149 was prepared from 107 which was prepared by Cu(II)(OAc)$_2$ mediated coupling of 101d and 3,5-dichlorobenzeneboronic acid. Conversion of 107 to I-149 was carried out by the procedure described in steps 7-9 of Example 1 except 4-amino-3-chloro-benzenesulfonamide replaced 4-amino-benzene-sulfonamide.

EXAMPLE 48

2-[3-(3-Chloro-5-cyano-phenoxy)4,5-dimethyl-phenyl]-N-(2-methyl4-sulfamoyl-phenyl)-acetamide (I-183)

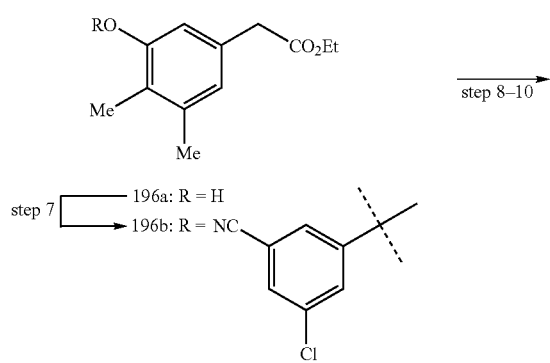

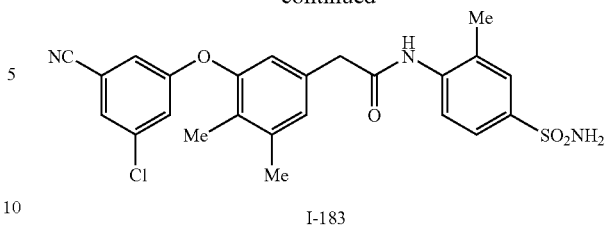

I-183 step 1—A mixture of 4-hydroxy-3-methoxyphenylacetic acid (20; 1.0 g; 5.49 mmol, SCHEME 2) and hexamethylene-tetramine (0.808 g; 5.76 mmol) and TFA (7 mL) were stirred and heated at 90° C. for 4 h. The reaction was cooled and excess TFA removed in vacuo and 35 mL of ice and water was added to the residue. The resulting dark brown solution was stirred at RT for 20 min. The aqueous solution was extracted with Et$_2$O (40 mL) and the extract was dried (Na$_2$SO$_4$), filtered and evaporated to afford 0.70 g of 22a (61%); ms (M+H)$^+$=211.13.

step 2—To a solution of 22a (4.0 g; 19.03 mmol) in EtOH (80 mL) was added con H$_2$SO$_4$ (1 mL). The reaction was heated at reflux for 6 h. Approximately 80% of the EtOH was removed in vacuo and the residue partitioned between EtOAc/H$_2$O (1:1) the organic phase residue washed with 10% NaHCO$_3$, water (100 mL), dried (Na$_2$SO$_4$), filtered and evaporated to afford a brown oil 22b (88%); ms (M+H)$^+$=239.19.

step 3—A mixture of 22b (3.70 g; 15.53 mmol), 5% Pd/C (0.350 g), HOAc (45 mL) were shaken under a H$_2$ atmosphere (40 psi) for 8 h. TLC showed product and the corresponding benzyl alcohol. An additional 300 mg of Pd/C in 25 mL HOAc was added and hydrogenation continued for another 8 h. A second portion of 0.15 g of Pd/C in HOAc (15 mL) was added and reaction continued for another 12 h. The mixture was diluted with EtOAc and filtered through a pad of CELITE®. The catalyst was washed with EtOAc and the combined organic extracts dried (Na$_2$SO$_4$) and evaporated. The product was purified by silica gel chromatography and eluted with CH$_2$Cl$_2$:hexane (4:1) to afford 2.64 g of 22c (75.8%).

step4—To a solution of 22c (5.87 g; 26.175 mmol) in CH$_2$Cl$_2$ cooled to 0° C. was added pyridine (3.60 mL; 44.51 mmol) followed by dropwise addition of triflic anhydride (6.605 mL; 39.26 mmol) over about 20 min. The reaction was stirred at 0° C. for 3.5 h. The reaction mixture was extracted with dilute HCl and half-saturated NaHCO$_3$, dried (Na$_2$SO$_4$) and evaporated to yield 9.41 g of 24a as a brown oil (100%).

step5—To a suspension of PdCl$_2$(dppf) (0.650 g; 0.785 mmol) in THF (40 mL) cooled to 0° C. was added dropwise a solution of DIBAL-H (1.0 M in PhMe; 1.57 mL; 1.57 mmol). The resulting mixture was stirred at 0° C. for 5 minutes and a solution of 24a in 5 mL of THF was added followed by Me$_2$Zn (23 mL; 46.0 mmol; 1.0 M in PhMe). The mixture was stirred at 0° C. for 5 m and heated at reflux for 2.5 h then cooled to rt for 30 m. The reaction was poured into dilute HCl and extracted with EtOAc (2×100 mL), dried (Na$_2$SO$_4$), and evaporated. The crude product was purified by silica gel chromatography and eluted with CH$_2$Cl$_2$:hexane (1:2 to 1:1 to 2:1 v/v) to yield 5.1 g (87.6%) of 24b.

step6—A solution of ethyl 3,4-dimethyl-5-methoxyphenylacetate (24b; 0.560 g; 2.519 mmol) and CH$_2$Cl$_2$ (40 mL) was cooled to −78° C. and a solution of BBr$_3$ (10.1 mL; 10.1 mmol; 1.0 M in CH$_2$Cl$_2$) dropwise over 10 min. After 1 h at −78° C. the reaction was allowed to warm to rt and stirred for 12 h. The reaction was cooled in an ice-water bath and the reaction quenched with 15 mL of ice/water. The aqueous phase was extracted with CH$_2$Cl$_2$:EtOAc (3:1 v/v), dried (Na$_2$SO$_4$), filtered and evaporated to yield 0.52 g (99%) of 24c; ms 209.21 (M+H)$^+$.

steps 7-10 were carried out as described in steps 6 to 9 of Example 1 except in the final step of the present example, 4-amino-3-methyl-benzenesulfonamide replaced 4-amino-3-benzenesulfonamide.

Compound I-182 was prepared in the same manner except in the final step of the present example, 4-amino-3-methyl-benzenesulfonamide was replaced with 4-amino-benzene-sulfonamide.

Compound I-184 was prepared in the same manner except in the final step of the present example, 4-amino-3-methyl-benzenesulfonamide was replaced with 4-amino-3-chloro-benzenesulfonamide.

EXAMPLE 49

2-[3-(2-Bromo-5-chloro-phenoxy)-4-isopropyl-phenyl]-N-(4-sulfamoyl-phenyl)-acetamide (I-26)

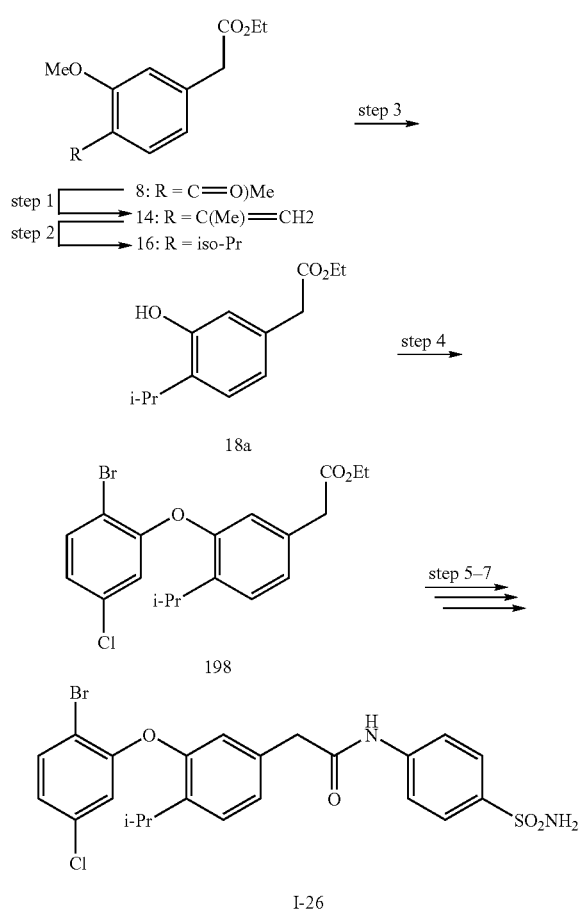

step 1

To a suspension of PPh$_3$CH$_3$$^+$Br$^-$ (36.29 g; 101.6 mmol) in THF (150 mL) cooled to −40° C. was added dropwise n-BuLi (40.6 mL; 1.6 M in hexanes) and the resulting solution was allowed to warm to −10° C. for 10 m and re-cooled to −40° C. To the resulting solution was added in one portion ethyl 4-acetyl-3-methoxyphenylacetate (8, see Example 10; ) and the reaction mixture was stirred at 0° C. for 30 m and warmed to rt and stirred for an additional 2 h. The reaction mixture was diluted with hexane filtered through a pad of CELITE ® and the solids washed with hexane:Et$_2$O (5:1 v/v; 60 mL). The combined organic layers were washed with water (50 mL) and brine (50 mL), dried (Na$_2$SO$_4$), filtered and evaporated to yield a yellow oil. The product was purified by silica gel chromatography and eluted with CH$_2$Cl$_2$:hexane (50- 66% DCM) to yield 9.1 g of 14.

step 2

A suspension of 14 (9.0 g; 38.41 mmol), 5% Pd/C (380 mg) in 50 mL HOAc and 50 mL EtOH was shaken under a hydrogen atmosphere (50 psi) for 7 h. The mixture was filtered through a pad of CELITE® and the filtered catalyst was washed with EtOAc. The solvents were evaporated under reduced pressure and the residue dissolved in MTBE and carefully washed with sat'd HaHCO$_3$, water and brine. The resulting solution was dried (Na$_2$SO$_4$), filtered and evaporated to yield ethyl 4-iso-propyl-3-methoxyphenylacetate (16; 9.0 g) as a yellow oil.

step 3—A solution of 16 (3.38 g; 14.30 mmol) and CH$_2$Cl$_2$ (150 mL) were cooled to −78° C. and a solution of BBr$_3$ (5.41 mL; 57.22 mmol) in 130 mL of CH$_2$Cl$_2$ were added dropwise over a 30 m period. The reaction mixture was stirred at −78° C. for 1 h, allowed to warm to rt for 4 h and re-cooled to −78° C. and carefully quenched with sat'd. NaHCO$_3$ (80 mL). The aqueous layer was extracted with CH$_2$Cl$_2$ (1×100 mL), EtOAc (50 mL) and the combined aqueous layers washed with water and brine, dried (Na$_2$SO$_4$) and evaporated to yield a light brown oil. The phenol was purified by silica gel chromatography and eluted with CH$_2$Cl$_2$:hexane (3:1) to CH$_2$Cl$_2$ to CH$_2$Cl$_2$:EtOAc (100:4) to yield ethyl 4-iso-propyl-3hydroxyphenylacetate (18a; 3.0 g; 94%)

Introduction of the aryloxy linkage (step 4) was accomplished by reacting 18a and 1-bromo4-chloro-2-fluorobenzene as described in step 1 of example 17 to afford 198. Steps 5 to 7 were carried out by the procedure described in steps 7-9 of example 1 to afford I-26.

Compound I-27 was prepared in the same manner except in the final step of the present example 2-chloro-benzeneamine replaced 4-amino-benzenesulfonamide.

EXAMPLE 50

2-[4,5-Dibromo-3-(3-cyano-5-difluoromethyl-phenoxy)-2-fluoro-phenyl]-N-(2-methyl4-sulfamoyl-phenyl)-acetamide (I-104)

[4,5-Dibromo-3-(3-cyano-5-difluoromethyl-phenoxy)-2-fluoro-phenyl]-acetic acid ethyl ester (200) was isolated as a byproduct in the Sandmeyer reaction used in the preparation of 186 described in step 1 of example 40. The dibromo compound was converted to I-104 by the procedure described in steps 7 to 9 of example 1 except in the present example, 4-amino-3-methyl-benzenesulfonamide replaced 4-amino-benzenesulfonamide.

EXAMPLE 51

(4-{2-[3-(3-Chloro-5-cyano-phenoxy)4-methyl-phenyl]-acetylamino}-3-methyl-phenoxy)-acetic acid (I-234)

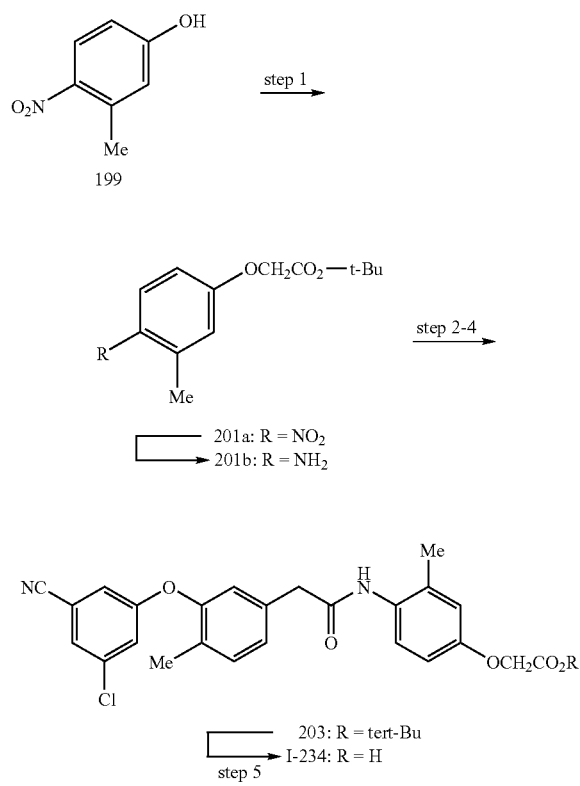

$K_2CO_3$ (2.7 g, 1 equiv) was added to a solution of 199 (3.0 g, 19.6 mmol) and DMF (20 mL). To this mixture was added the tert-butyl bromoacetate (4.09 g, 1.1 equiv). The reaction mixture was stirred for 2 h, poured into $NH_4Cl$ solution, and extracted with EtOAc. The organic layer was washed with water, dried ($MgSO_4$), filtered, and concentrated to provide a brown oil. This oil was purified by $SiO_2$ chromatography eluting with a EtOAc/hexane gradient (0% to 20% EtOAc) to afford 3.67 g (71%) of the 201a as a white solid. The solid was dissolved in EtOH, 10% Pd/C (0.3 g) was added, and the reaction was placed under a hydrogen atmosphere(45 psi). After 2 h, the catalyst was filtered and the filtrate concentrated in vacuo to afford 201b.

Hydrolysis of the ester, formation of the acid chloride and condensation with 201b were carried out as described in steps 7 to 9 of Example 1 which afforded 203. The ester 203 (0.22 g, 0.42 mmol) was stirred in formic acid (4.6 mL) under $N_2$. After 2 h, the reaction was diluted with EtOAc and poured into water. The organic layer was washed with NaHCO3. The combined organic layers were ($MgSO_4$) and concentrated in vacuo to afford 0.103 g (53%) of I-234 as a white solid.

EXAMPLE 52

2-[3-(4-Chloro-benzoyl)-5-methyl-phenyl]-N-(2-methyl4-sulfamoyl-phenyl)-acetamide (I-255)

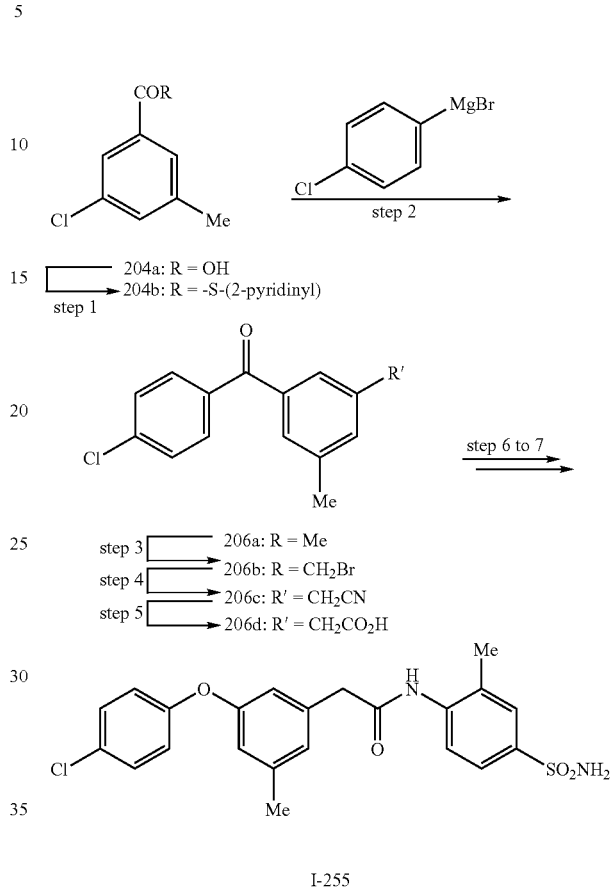

step 1—A solution of 204a (25 g, 0.166 mmol), triphenylphosphine (43.66 g, 0.166 mmol), 2,2'-dipyridyl disulfide (36.67 g, 0.166 mmol) and MeCN (250 mL) was heated under an Ar atmosphere for 2 h. The reaction mixture was cooled to RT and partitioned between EtOAc and $H_2O$. The aqueous phase was extracted with EtOAc and the combined EtOAc extracts were dried ($MgSO_4$), filtered and concentrated in vacuo. The crude product was purified by $SiO_2$ chromatography eluting with a EtOAc/hexane gradient (10 to 30% EtOAc) which afforded 37 g of 204b.

step 2—A dry flask was charged with fine Mg turnings (1.48 g, 60.8 mmol) and dry THF (50 mL) and a crystal of iodine was added. A solution of 1-bromo-4-chloro-benzene (11.64 g, 60.8 mmol) and dry THF was added dropwise. If the Grignard reagent does not form spontaneously the flask was gently warmed until the reaction began and stirring was continued until the Mg was consumed. To a solution of 204b (7.4 g, 30.4 mmol)and dry THF (50 mL) cooled to 0° C. and maintained under an Ar atmosphere was added dropwise the solution of 1-chloro-1-bromomagnesium-benzene over a 30 min period. After the reaction was complete the solution was warmed to RT and stirred overnight. The reaction mixture was cooled to 0° C. and the reaction was quenched with saturated $NH_4Cl$. The solution was extracted with EtOAc, dried ($MgSO_4$), filtered and evaporated. The crude product was purified by $SiO_2$ chromatography eluting with a EtOAc/hexane gradient (10 to 30% EtOAc) to afford 3.46 g of 206a.

step 3—A solution of 206a (3.46 g, 14.1 mmol), NBS (2.52 g, 14.1 mmol) and benzoyl peroxide (0.035 g) and CCl$_4$ (75 mL) was heated to reflux for 1.5 h while exposed to a 300 watt lamp. The solution was cooled and the precipitated succinimde was removed by filtration. The solvent was removed in vacuo and purified by flash chromatography eluting with a EtOAc/hexane gradient (1 to 2% EtOAc) to afford 206b.

step 4—A solution of 206b (1.97 g, 6.09 mmol), sodium cyanide (0.59 g, 12.1 mmol) and EtOH/H$_2$O (50 mL, 90% EtOAc was stirred at RT overnight. The reaction mixture was concentrated in vacuo and partitioned between EtOAc and H$_2$O. The aqueous phase was extracted with EtOAc and the combined extracts dried (MgSO$_4$), filtered and evaporated. The crude solid was recrystallized from hexane/EtOAc to afford 1.36 g of 206c.

step 5—A mixture of 206c (1.36 g, 5.04 mmol) and concentrated HCl/HOAc (50 mL, 1:1) was stirred at 100° C. for 2 h. The reaction mixture was concentrated in vacuo, H$_2$O was added and the aqueous phase extracted twice with EtOAc. The combined extracts were dried (MgSO$_4$), filtered and evaporated to afford 1.2 g of 206d as a white powder.

Steps 6 and 7 were carried out by the procedure in steps 8 and 9 of example 1 except in step 7 of the present example 4-amino-3-methyl-benzenesulfonamide replaced 4-amino-benzenesulfonamide to afford I-255.

Compound I-254 was prepared as described for I-255 except in step 7, 4-amino-3-methyl-benzenesulfonamide was replaced by 4-amino-benzenesulfonamide.

Compound I-256 was prepared as described for I-255 except in step 2, 2-bromo-1-chloro-benzene was used instead of 4-bromo-1-chloro-benzene.

Compound I-257 was prepared as described for I-255 except in step 7, 4-amino-3-chloro-benzenesulfonamide was used in place of 4-amino-3-methyl-benzenesulfonamide.

Compound I-258 was prepared as described for I-255 except in step 7, 2-chloro-phenylamine was used in place of 4-amino-3-methyl-benzenesulfonamide.

Compound I-259 was prepared as described for I-256 except in step 7, 2-chloro-phenylamine was used in place of 4-amino-3-methyl-benzenesulfonamide.

Compound I-260 was prepared as described for I-255 except in step 2, 1-bromo-3-chlorobenzene was used in place of I-bromo-4-chlorobenzene.

Compound I-261 was prepared as described for I-256 except in step 7, 4-amino-benzenesulfonamide replaced 4-amino-3-methyl-benzenesulfonamide.

Compound I-262 was prepared as described for I-260 except in step 7, 2-chloro-phenylamine replaced 4-amino-3-methyl-benzenesulfonamide.

Compound I-232 was prepared as described for I-255 except in step 2, 1-bromo4-chlorobenzene was replaced by 1-bromo-3,5-dichloro-benzene.

Compound I-231 was prepared as described for I-232 except in step 7, 4-amino-3-methyl-benzenesulfonamide was replaced by 2-chloro-phenylamine.

Compound I-247 was prepared as described for I-255 except in step 1 2-chloro-5-methyl benzoic acid was used in place of 3,5-dimethylbenzoic acid, in step 2, 1-bromo-3,5-dichloro-benzene was used instead of 4-bromo-1-chloro-benzene and in step 7, 4-amino-benzenesulfonamide was replaced by 2-chloro-phenylamine.

Compound I-252 was prepared as described for I-247 except in step 7, 4-amino-3-methyl-benzenesulfonamide was used in place of 2-chloro-phenylamine Compound I-248 was prepared as described for I-247 except in step 2, 2-bromo-1,4-dichloro-benzene was used instead of 1-bromo-3,5-dichloro-benzene and in step 7, 2-chloro-phenylamine was used instead of 4-amino-benzenesulfonamide.

Compound I-249 was prepared as described for I-248 except in step 7, 4-amino-3-methyl-benzenesulfonamide was used in place of 2-chloro-phenylamine Compound I-250 was prepared as described for I-248 except in step 7, 4-amino-benzenesulfonamide was used in place of 2-chloro-phenylamine.

Compound I-253 was prepared as described for I-248 except in step 7, 4-amino-3-chloro-benzenesulfonarmide was used in place of 2-chloro-phenylamine Compound I-251 was prepared as described for I-248 except in step 7, phenylamine was used in place of 2-chloro-phenylamine

EXAMPLE 53

2-[3-(2-Bromo-5-chloro-phenylsulfanyl)-4-chloro-phenyl]-N-(4-sulfamoyl-phenyl)-acetamide (I-243)

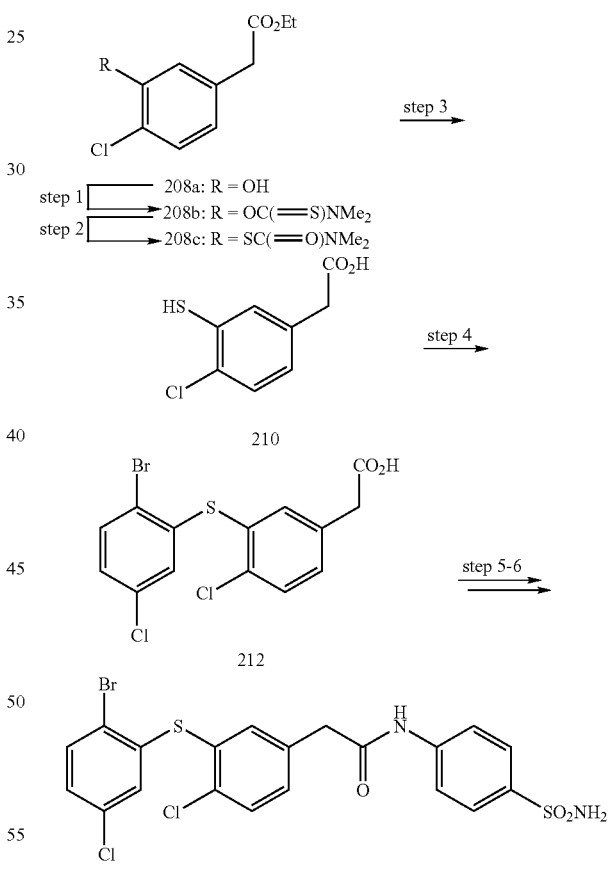

step 1—A solution of 208a (10.11 g, 47 mmol), dimethylthiocarbamoyl chloride (8.73 g, 70.6 mmol), DABCO (10.56 g, 94.2 mmol) and DMF (75 mL) was stirred at RT for 20 min then at 75° C. for an additional 30 min. The reaction mixture was cooled to RT, diluted with H$_2$O, and twice extracted with EtOAc. The combined EtOAc extracts were thrice washed with H$_2$O, dried (MgSO$_4$), filtered and evaporated. The impure product was purified by SiO$_2$ chromatography elution with an EtOAc/hexane gradient (10 to 20% EtOAc) to afford 11.27 g of 208b.

step 2—A flask was charged with 208b (11.27 g) and the melt was heated at 220° C. overnight. The crude product was purified by SiO$_2$ chromatography eluting with an EtOAc/hexane gradient (10 to 20% EtOAc) to afford 7.08 g of 208c. An additional 2.19 g was isolated form the column which contained a small amount of an impurity.

step 3—To a solution of 208c (7.08 g, 23.4 mmol) was added a solution of NaOH (3.75 g, 93.8 mmol) and H$_2$O (25 mL). The solution was heated for 1 h at 60° C. under an Ar atmosphere. The reaction mixture was cooled to RT and acidified with 1 N HCl. The resulting solid was filtered, washed well with water and dried to afford 4.6 g of product. The crude product along with an earlier batch was purified by SiO$_2$ chromatograph eluting with EtOAc/hexane/HOAc (39.5:60:0.5) to afford 5.26 g of 210.

step 4—A solution of 210 (0.26 g, 1.28 mmol), 1-bromo-2-fluoro4-chloro-benzene (0.16 mL, 1.28 mmol), K$_2$CO$_3$ (0.35 g, 2.56 mmol) and DMF (12 mL) maintained under an Ar atmosphere was warmed to 60° C. overnight. The reaction mixture was cooled to RT, diluted with H$_2$O (20 mL) and extracted with EtOAc. The aqueous phase was adjusted to pH 2 with dilute HCl and the resulting precipitate was collected by filtration and washed with H$_2$O. The crude product was preabsorbed onto SiO$_2$ and purified by flash chromatography elution 50% EtOAc/hexane to afford 0.053 g of 212.

Steps 5 and 6 were carried out as described for steps 8 and 9 of Example 1 to afford I-243.

Compound I-244 prepared as described for I-243 except in step 7, 4-amino-benzenesulfonamide was replaced with 2-chlorophenylamine.

Compound I-242 prepared as described for I-243 except in step 4, 1-bromo-2-fluoro4-chloro-benzene was replaced by 5-fluoroisophthalonitrile.

EXAMPLE 54

(3-Chloro4-{2-[3-(3-chloro-5-cyano-phenoxy)4-methyl-phenyl]-acetylamino}-phenyl)-acetic acid methyl ester (I-235) and (3-Chloro4-{2-[3-(3-chloro-5-cyano-phenoxy)4-methyl-phenyl]-acetylamino}-phenyl)-acetic acid (I-236)

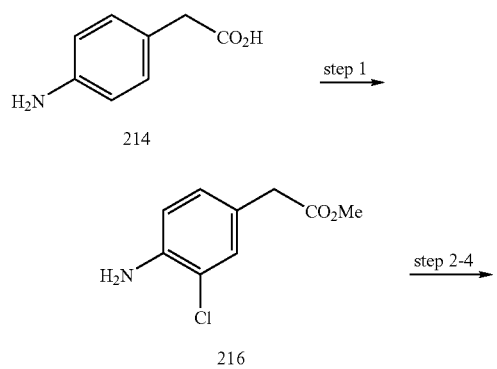

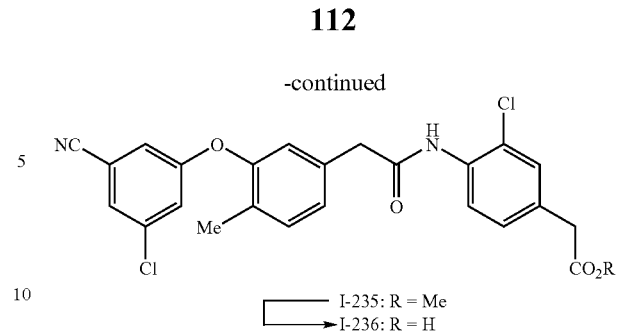

step 1

The aniline 214 (21.4 g, 140 mmol) was dissolved in MeOH (140 mL), and 1 mL of concentrated sulfuric acid was added. The solution was heated to reflux for 3 d, cooled, and poured into saturated NaHCO$_3$ solution. The aqueous solution was extracted with a 1:1 EtOAc/hexane, dried (MgSO$_4$) and evaporated in vacuo. Six grams of the resulting crude product was purified by SiO$_2$ chromatography eluting with a hexane/EtOAc gradient (10% to 50% EtOAc) to provide 5.5 grams of methyl ester. The methyl ester (0.50 g, 3.0 mmol) was dissolved in MeCN (10 mL). The solution was warmed to 30° C., and NCS (0.42 g, 1.05 equiv) was added in one portion. After 1 h, the reaction was warmed to 50 C. After an addition hour, the reaction was cooled to RT and the solvent was evaporated. The remaining oil was dissolved in DCM, and the organic layer was washed with a 5% NaOH solution, brine, and dried (MgSO$_4$). Evaporation of the volatile materials and SiO$_2$ chromatography of the residue provided 0.28 g (45%) of 216.

Steps 2-4 were carried out as described in steps 7 to 9 of example 1 except in the final step 4-amino-benzenesulfonate was replaced by 216 which afforded I-235.

The ester was hydrolyzed by adding LiOH (1.1 mL of a 2 M solution, 4 equiv) to a solution of the ester (0.29 g, 0.55 mmol) in THF (4 mL). The solution was stirred for 4 h. The mixture was quenched with 2 M HCl solution, and the aqueous layer was extracted with ethyl acetate. The combined organic extracts were washed with brine and dried over magnesium sulfate. Evaporation of the volatile materials afforded I-236.

EXAMPLE 55

(4-{2-[3-(3-Chloro-5-cyano-phenoxy)-4-methyl-phenyl]-acetylamino}-3-methyl-phenoxy)-acetic acid (I-234)

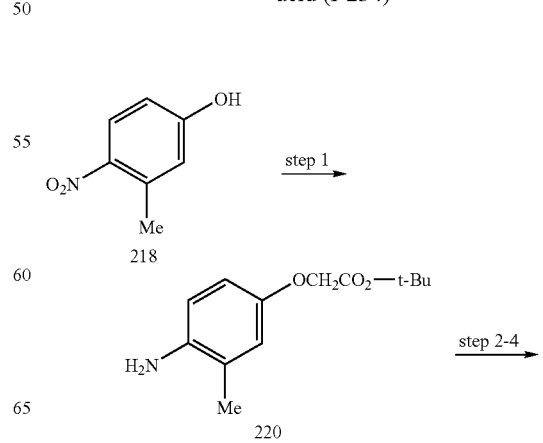

-continued

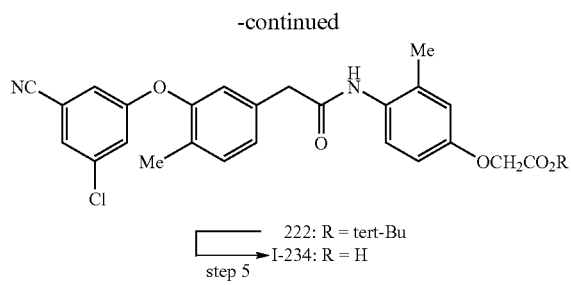

222: R = tert-Bu
I-234: R = H
step 5 step 1—K₂CO₃ (2.7 g, 1 equiv) was added to a solution of 218 (3.0 g, 19.6 mmol) and DMF (20 mL). To this mixture was added the tert-butyl bromoacetate (4.09 g, 1.1 equiv). The reaction mixture was stirred for 2 h, poured into NH₄Cl solution, and extracted with EtOAc. The organic layer was washed with water, dried (MgSO₄), filtered, and concentrated to provide a brown oil. This oil was purified by SiO₂ chromatography eluting with a EtOAc/hexane gradient (0% to 20% EtOAc) to afford 3.67 g (71%) of the nitro ether as a white solid. This solid was dissolved in EtOH, 10% Pd/C (0.3 g) was added, and the reaction was placed under a hydrogen atmosphere (45 psi). After 2 h, the catalyst was filtered and the filtrate concentrated in vacuo to afford 220

Steps 2-4 were carried out as described in steps 7 to 9 of example 1 except in the final step 4-amino-benzenesulfonate was replaced by 220.

The ester 220 (0.22 g, 0.42 mmol) was stirred in formic acid (4.6 mL) under N₂. After 2 h, the reaction was diluted with EtOAc and poured into water. The organic layer was washed with NaHCO3. The combined organic layers were dried (MgSO₄) and concentrated in vacuo to afford 0.103 g (53%) of I-234 as a white solid.

EXAMPLE 56

2-[4-Chloro-3-(4-cyano-6-methyl-pyridin-2-yloxy)-2-fluoro-phenyl]-N-(2-methyl-4-sulfamoyl-phenyl)-acetamide (I-233)

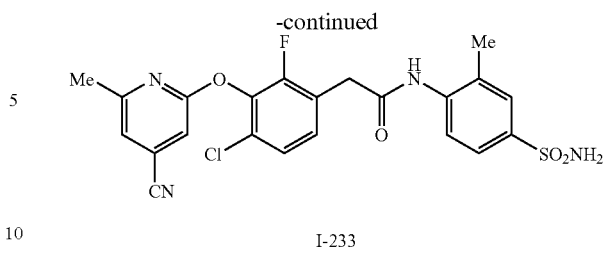

I-233 step 1 To a stirred mixture containing 2,6-dichloro-isonicotinonitrile (224, 0.95 g, 5.49 mmol), Cs₂CO₃ (1.97 g, 6.04 mmol) in dimethylacetarmide (20 mL) was added (4-chloro-2-fluoro-3-hydroxy-phenyl)-acetic acid ethyl ester (1.20 g, 5.16 mmol). The flask was flushed with argon and heated at 100° C. After stirring for 3 h the reaction mixture was cooled to RT and diluted with EtOAc/hexanes (3:1). The organic phase was washed with saturated NH₄Cl solution and brine solution, dried (MgSO₄) and concentrated in vacuo. The crude product was purified by SiO₂ chromatography eluting with a EtOAc/hexane gradient (0 to 20%) to afford 0.78 g (39%) of 226a as a white solid.

step 2—Me₂Zn solution (1.58 mL, 3.17 mmol, 2 M in PhMe) was added to a mixture (0° C.) containing 226a (0.78 g, 2.11 mmol), (Ph₃P)₂Pd(II)Cl₂ (0.15 g, 0.211 mmol), N,N-dimethylethanolamine (43 mL, 0.422 mmol) cooled to 0° C. After stirring for 20 min the reaction mixture was warmed to RT and stirred for 2 h then poured onto ice/aqueous saturated ammonium chloride solution. The organics were extracted with EtOAc, washed with brine, dried (MgSO₄) and concentrated in vacuo. The crude product was purified by SiO₂ chromatography eluting with a EtOAc/hexane gradient (0 to 15%) to afford 0.67 g (91%) of 226b as a white solid.

The phenyl acetic acid ester 226b was converted to I-124 (steps 24) utilizing the procedures described in steps 7-9 of Example 1 except in the final step 4-amino-3-methyl-benzenesulfonamide replaced 4-aminobenzenesulfonamide.

EXAMPLE 57

2-[7-(4-Chloro-benzoyl)-2,3-dihydro-benzofuran-5-yl]-N-(4-sulfamoyl-phenyl)-acetamide (I-241)

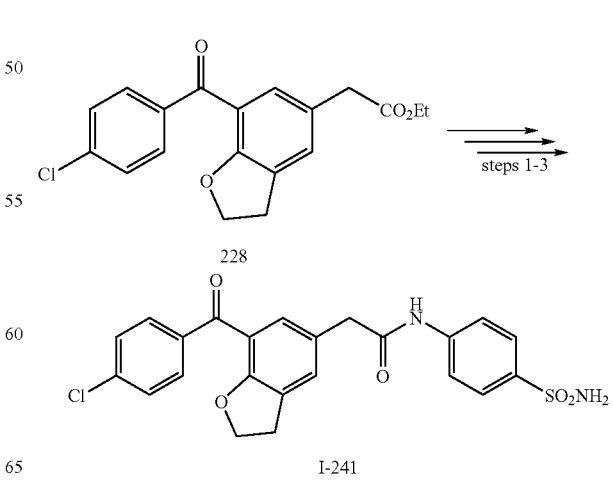

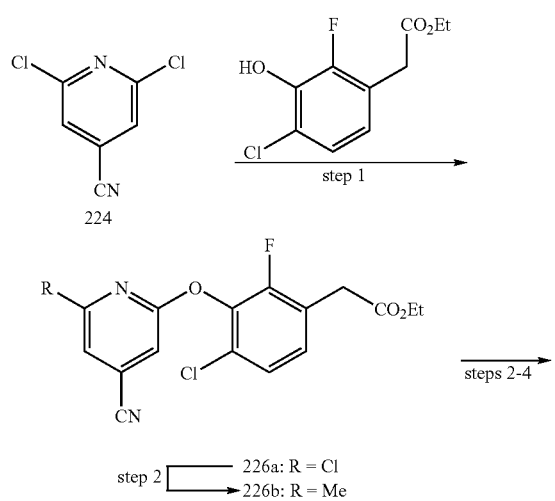

step 2
226a: R = Cl
226b: R = Me

The dihydrobenzoftiran 228 was prepared as described by J. Dunn et al. *J. Med Chem* 1986 29:2326. Steps 1-3 were carried out as described in steps 7-9 of example 1 to afford I-241.

Compound I-240 was prepared as described for I-241 except in step 3, 2-chloro-phenylamine was used in place of 2-amino-benzenesulfonamide

EXAMPLE 58

2-[4-Chloro-3-(2,5-dichloro-benzyl)-phenyl]-N-(2-chloro-4-sulfamoyl-phenyl)-acetamide (I-209)

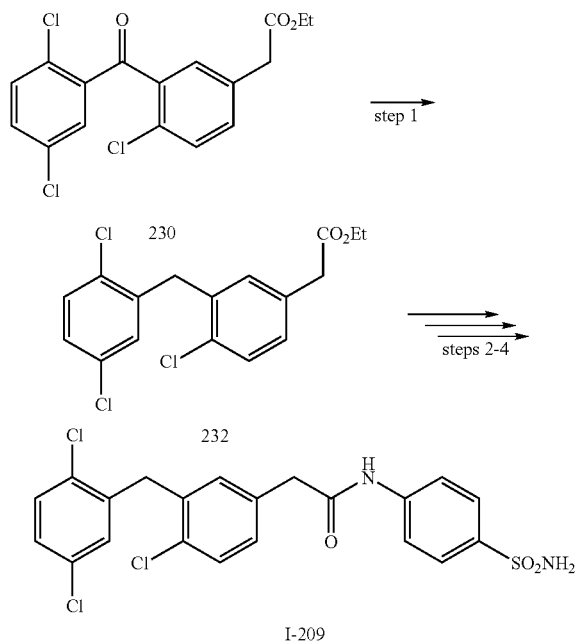

step 1—A solution of 230 (0.521 g, 1.47 mmol) and triethylsilane (0.64 mL, 3.98 mmol) and TFA (10 mL) were stirred overnight at RT. The reaction mixture was diluted with $H_2O$ (20 mL) and extracted twice with EtOAc. The combine extracts were dried, filtered and evaporated to afford 232. Steps 2-4 were carried out as described in steps 7-9 of example 1 except in the final step 4-amino-benzenesulfonamide was replaced by 4-amino-3-chloro-benzenesulfonamide to afford I-209.

EXAMPLE 59

2-[3-(5-Cyano-2-ethyl-benzoyl)-4-ethyl-phenyl]-N-(2-methyl4-sulfamoyl-phenyl)-acetamide (I-268)

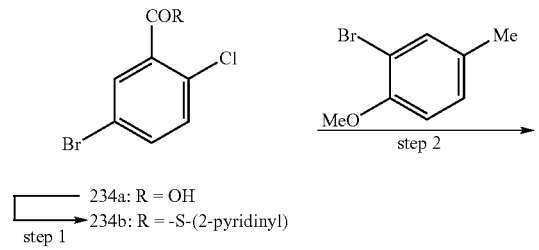

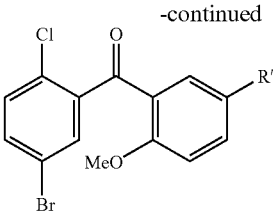

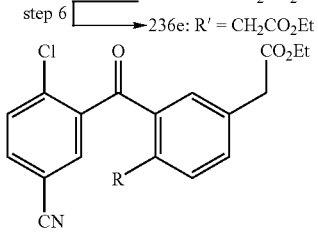

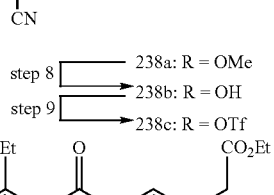

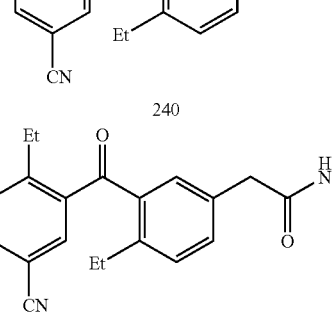

I-268

Steps 1 to 5 were carried out as described in steps 1 to 5 Example 52 except in the present example 5-15 chloro-2-bromo-benzoic acid was used in place of 3,5-dimethylbenzoic acid.

step6—A solution of 236d (6.09 g, 15.9 mmol), EtOH (75 mL) and con $H_2SO_4$ were heated at 80° C. overnight. Approximately 75% of the EtOH was evaporated and the residue diluted with $H_2O$ and twice extracted with EtOAc. The combined extracts were washed with saturated $NaHCO_3$, dried ($MgSO_4$), filtered and evaporated to yield 5.54 g of 236e as a white solid.

step7—A flask was charged with 236e (5.54 g, 13.4 mmol), $Zn(CN)_2$ (1.57 g, 13.4 mmol), $Pd[P(Ph)_3]_4$ (1.55 g, 13.34 mmol) and dry DMF (70 mL) and the flask thrice evacuated and flushed with Ar. The reaction mixture was heated at 80° C. for 1.5 h. The reaction was cooled to RT and diluted with EtOAc/hexane (300 mL 1: 1) and twice extracted with EtOAc/hexane. The EtOAc extracts were washed once with $H_2O$, dried ($MgSO_4$), filtered and evaporated. The resulting orange oil was purified by SiO$_2$ chromatography eluting with an EtOAc/hexane gradient (20 to 30% EtOAc) to afford 1.1 g of 238a as white solid.

step 8—To a solution of 238a (3.1 g, 8.66 mmol) and DME (40 mL) cooled to −78° C. was added dropwise over 5 min, a solution of BBr$_3$ and DCM (43.3 mL of a 1.0 M solution in DMC, 43.3 mmol). After the addition was complete the reaction mixture was stirred at RT for 2 h, poured onto ice. The aqueous layer was separated and extracted with DCM and the combined DCM solutions washed with brine, dried (MgSO$_4$), filtered and evaporated. The crude product was purified by SiO$_2$ chromatography eluting with 20% EtOAc/hexane to afford 2.63 g of 238b as a white solid.

step 9—The conversion of 238b to the triflate 238c was carried out as described in step 1 of example 6.

step 10—A flask was charged with 238c (1.2 g, 2.52 mmol), Pd(dppf).CH$_2$Cl$_2$ (0.103 g, 0.126 mmol), TEA (3.4 mL, 3.78 mmol). DIBAL-H (75 µL, 0.113 mmol) was added at 0° C., warmed to RT and Et$_2$Zn was added as described in step 2 of example 6 to afford 0.86 g of 240.

Steps 11-13 were carried out as described for steps 7-9 of example 1 except in the present example 4-amino-3-methyl-benzenesulfonamide was used in place of 4-amino-benzene-sulfonamide which afford I-268.

EXAMPLE 60

HIV Reverse Transcriptase Assay: Inhibitor IC$_{50}$ Determination

HIV-1 RT assay was carried out in 96-well Millipore MultiScreen MADVNOB50 plates using purified recombinant enzyme and a poly(rA)/oligo(dT)$_{16}$ template-primer in a total volume of 50 µL. The assay constituents were 50 mM Tris/HCl, 50 mM NaCl, 1 mM EDTA, 6 mM MgCl$_2$, 5 µM dTTP, 0.15 µCi [$^3$H] dTTP, 5 µg/ml poly (rA) pre annealed to 2.5 µg/ml oligo (dT)$_{16}$ and a range of inhibitor concentrations in a final concentration of 10% DMSO. Reactions were initiated by adding 4 nM HIV-1 RT and after incubation at 37° C. for 30 min, they were stopped by the addition of 50 µl ice cold 20% TCA and allowed to precipitate at 4° C. for 30 min. The precipitates were collected by applying vacuum to the plate and sequentially washing with 3×200 µl of 10% TCA and 2×200 µl 70% ethanol. Finally, the plates were dried and radioactivity counted in a Packard TopCounter after the addition of 25 µl scintillation fluid per well. IC$_{50}$'s were calculated by plotting % inhibition versus log$_{10}$ inhibitor concentrations.

EXAMPLE 61

Anti-Viral Assay

Anti-viral assays were carried out by the method described by R. E. Pauwels et al. *J. Virol. Methods* 1988 20(4):309-322.

TABLE 2

| Compound # | RT inhibition IC$_{50}$ (µM) | Anti-Viral Assay EC$_{50}$ (µM) |
| --- | --- | --- |
| I-138 | 0.0045 | — |
| I-63 | 0.0058 | — |
| I-127 | 0.0059 | — |
| I-179 | 0.0074 | 0.0004 |
| I-83 | 0.0081 | 0.0009 |
| I-109 | 0.0136 | 0.0013 |
| I-180 | 0.0091 | — |
| I-84 | 0.014 | 0.0004 |

TABLE 2-continued

| Compound # | RT inhibition IC$_{50}$ (µM) | Anti-Viral Assay EC$_{50}$ (µM) |
| --- | --- | --- |
| I-140 | 0.021 | 0.0004 |
| I-165 | 0.021 | 0.0004 |
| I-169 | 0.027 | 0.0004 |

EXAMPLE 62

Pharmaceutical Compositions

Pharmaceutical compositions of the subject Compounds for administration via several routes were prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. | |
| --- | --- | --- |
| Active compound | 1.0 | g |
| Fumaric acid | 0.5 | g |
| Sodium chloride | 2.0 | g |
| Methyl paraben | 0.15 | g |
| Propyl paraben | 0.05 | g |
| Granulated sugar | 25.5 | g |
| Sorbitol (70% solution) | 12.85 | g |
| Veegum K (Vanderbilt Co.) | 1.0 | g |
| Flavoring | 0.035 | ml |
| Colorings | 0.5 | mg |
| Distilled water | q.s. to 100 | ml |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A method for treating an HIV infection comprising: administering to a host in need thereof a therapeutically effective amount of a compound according to formula I

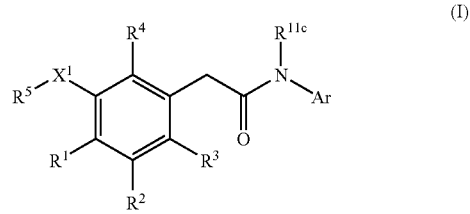

wherein
X$^1$ is —O—;
R$^1$ and R$^2$ are (i) each independently selected from the group consisting of hydrogen, C$_{1-6}$ alkyl, C$_{1-6}$ haloalkyl, C$_{3-8}$ cycloalkyl, C$_{1-6}$ alkoxy, C$_{1-6}$ alkylthio, C$_{1-6}$ alkylsulfinyl, C$_{1-6}$ sulfonyl, C$_{1-6}$ haloalkoxy, C$_{1-6}$ haloalkylthio, halogen, amino, C$_{1-6}$ alkylamino, C$_{1-6}$ dialkylamino, C$_{1-6}$ acylamino, intro and cyano; or, (ii) together R$^1$ and R$^2$ are —O—CH═CH— or —O—CH$_2$CH$_2$—
R$^3$ and R$^4$ are independently selected from the group consisting of hydrogen, C$_{1-6}$ alkyl, C$_{1-6}$ haloalkyl, C$_{1-6}$ alkoxy, C$_{1-6}$ haloalkoxy C$_{1-6}$ alkylthio, C$_{1-6}$ haloalkylthio, halogen, amino, nitro and cyano;
R$^5$ is aryl optionally substituted with one to three substituents independently selected from the group consisting of C$_{1-6}$ alkyl, C$_{2-6}$ alkenyl, C$_{1-6}$ haloalkyl, C$_{3-8}$ cycloalkyl, C$_{1-6}$ haloalkoxy, and cyano,
Ar is (i) phenyl optionally substituted with 1 to 3 substituents independently selected in each incidence is from the group consisting of C$_{1-6}$ alkyl, C$_{3-8}$ cycloalkyl, C$_{1-3}$ haloalkyl, C$_{1-6}$ alkoxy, halogen, cyano, C$_{1-6}$ sulfonyl, amino C$_{1-6}$ alkylsulfonyl, C$_{1-6}$ haloalkoxy, C$_{1-6}$ heteroalkyl, —X$^2$(CH$_2$)$_p$S(O)$_n$NR$^8$R$^9$; —(CH$_2$)$_p$COOR$^{11}$, —X$^2$(CH$_2$)$_p$NHC(O)NHR$^8$R$^9$, X$^2$(CH$_2$)$_p$CONR$^8$R$^9$, —SO$_2$R$^{13}$, —NR$^{8a}$R$^{9a}$, —X$^6$(CH$_2$)$_p$COOR$^{10}$, —X$^2$(CH$_2$)$_p$CN, and C(═O)CH$_2$N[(CH$_2$)$_2$]$_2$X$^4$; or,
(ii) a heteroaryl ring selected from the group consisting of pyridinyl, pyrazolyl and triazolyl said heteroaryl ring optionally substituted with one to three substituents selected from the group consisting of C$_{1-6}$ alkyl, C$_{1-6}$ alkoxy, C$_{1-6}$ alkylthio, halogen, C$_{1-6}$ aminoacyl and NR$^{8b}$R$^{9b}$;
R$^8$ and R$^9$ (i) taken independently, one of R$^8$ and R$^9$ is hydrogen or C$_{1-6}$ alkyl and the other of R$^8$ and R$^9$ is selected from the group consisting of hydrogen, —C(═O)R$^{14}$, —C(═O)CHR$^{12}$NH$_2$,—(CH$_2$)$_2$N[(CH$_2$)$_2$]$_2$O, COCO$_2$Me, C$_{3-8}$ cycloalkyl said cycloalkyl optionally substituted with one or two hydroxyl substituents, pyranyl, C$_{1-6}$ alkyl and aryl said alkyl and said aryl groups optionally substituted with one or two substituents independently selected from the group consisting of hydroxy, $C_{1-6}$ alkoxy, thiol, $C_{1-6}$ alkylthio, $C_{1-6}$ alkylsulfinyl, $C_{1-6}$ sulfonyl, and halogen; or, (ii) $R^8$ and $R^9$ taken together are $(CH_2)_2-X^5-(CH_2)_2$ or $-(CH_2)_o-$ optionally substituted with one or two substituents selected from the group consisting of halogen, hydroxyl and $NR^{11a}R^{11b}$;

$R^{8a}$ and $R^{9a}$ (i) taken independently are selected from the group consisting of hydrogen, $C_{1-6}$ alkyl, $C(=O)CO_2R^{11}$ and $SO_2R^{10}$, or (ii) taken together are $(CH_2)_rSO_2,(CH_2)_2S(O)_p(CH_2)_2$;

$R^{10}$ is $C_{1-6}$ alkyl;

$R^{11}$ is hydrogen or $C_{1-6}$ alkyl;

$R^{11a}$, $R^{11b}$ and $R^{11c}$ are independently $R^{11}$;

$R^{12}$ is the side chain of a naturally occurring α-amino acid;

$R^{13}$ is $C_{1-6}$ alkyl; $-(CH_2)_sCO_2R^{11}$, $-(CH_2)_2CN$, $-(CH_2)_2NH_2$, $-(CH_2)_uOH$;

$R^{14}$ is $C_{1-6}$ alkyl, $-(CH_2)_sNHR^{11a}R^{11b}$, $(CH_2)_sOR^{11}$, $-CH_2CH(OH)CH_3$, $CH_2N[(CH_2)_2]_2O$, $-(CH_2)_2CO_2R^{11}$, optionally substituted phenyl or pyridinyl;

$R^{15}$ is $C_{1-6}$ alkyl optionally substituted with one to three hydroxyl groups;

$X^2$ is $-O-$ or a bond;

$X^4$ is $-O-$ or $-NMe-$;

$X^5$ is $-O-$, $-S(O)_n-$ or $NR^{11}$;

$X^6$ is $O-$ or $-S(O)_n-$;

n is an integer from 0 to 2;

o is an integer from 4 to 6;

p is an integer from 0 to 6;

r is an integer from 3 to 4;

s is an integer from 1 to 2;

u is an integer from 2 to 3; and, hydrates, solvates and salts thereof.

2. A method according to claim 1 wherein:
$X^1$ is O and $X^2$ is a bond;
$R^3$ is hydrogen or halogen;
$R^4$ is hydrogen, halogen or $C_{1-6}$ alkyl;
$R^5$ is optionally substituted aryl;
$R^{11c}$ is hydrogen; and,
p is O.

3. A method according to claim 2 wherein:
Ar is optionally substituted aryl;
$R^1$ and $R^2$ are each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ haloalkoxy, $C_{1-6}$ haloalkylthio, halogen, nitro and cyano; and,
$R^3$ is hydrogen or fluoro; and,
$R^4$ is hydrogen, fluoro, chloro or $C_{1-6}$ alkyl.

4. A method according to claim 2 wherein $R^5$ is 2,4-disubstituted phenyl, 2,5-disubstituted phenyl, 3,5-disubstituted phenyl or 2,3,5-trisubstituted phenyl.

5. A method according to claim 4 wherein $R^1$ is chloro, bromo, $C_{1-6}$ alkyl or $C_{1-6}$ alkoxy, $R^2$ is hydrogen, $C_{1-6}$ alkyl or bromo, $R^3$ is H, $R^4$ is hydrogen or fluoro, $X^1$ is O, $R^5$ is di- or trisubstituted phenyl optionally substituted in each incidence with a substituents selected from the group consisting of halogen, cyano, $C_{1-6}$ alkyl, $C_{1-6}$ haloalkyl and Ar is phenyl substituted according to formula II

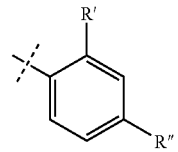

(II)

wherein R' is hydrogen $C_{1-6}$ alkyl, or chloro and R" is hydrogen, $X^2(CH_2)_pS(O)_nNR^8R^9$, $X^2$ is a bond, p is 0 and n is 2.

6. A method according to claim 5 wherein $R^8$ is hydrogen, $R^9$ is hydrogen, $C(=O)R^{14}$ or $C(=O)CR^{12}NH_2$; and, $^{14}$ is $C_{1-6}$ alkyl.

7. A method according to claim 1 wherein:
$X^1$ and $X^2$ are O;
$R^3$ is hydrogen or halogen;
$R^4$ is hydrogen, halogen or C1-6 alkyl;
$R^5$ is optionally substituted phenyl;
$R^{11c}$ is hydrogen; and,
p is 1 to 6.

8. A method according to claim 1 where the compound is selected from the group consisting of:
2-[4-chloro-3-(3-chloro-5-cyano-phenoxy)-2-fluoro-phenyl]-N-(2-chloro4-sulfamoyl-phenyl)-acetamide;
2-[4-chloro-3-(3-chloro-5-cyano-phenoxy)-2-fluoro-phenyl]-N-(2-chloro-4-propionylsulfamoyl-phenyl)-acetamide; sodium salt;
2-[3-(3-chloro-5-cyano-phenoxy)-2-fluoro4-methyl-phenyl]-N-(2-chloro-4-sulfamoyl-phenyl)-acetamide;
2-[4-bromo-3-(3-chloro-5-cyano-phenoxy)-2-fluoro-phenyl]-N-(2-chloro4-sulfamoyl-phenyl)-acetamide;
2-[4-bromo-3-(3-chloro-5-cyano-phenoxy)-2-fluoro-phenyl]-N-(2-chloro-4-propionylsulfamoyl-phenyl)-acetamide; sodium salt;
N-(4-butyrylsulfamoyl-2-chloro-phenyl)-2-[4-chloro-3-(3-chloro-5-cyano-phenoxy)-2-fluoro-phenyl]-acetamide; sodium salt;
N-[4-((S)-2-amino-3-methyl-butyrylsulfamoyl)-2-chloro-phenyl]-2-[4chloro-3-(3-chloro-5-cyano-phenoxy)-2-fluoro-phenyl]-acetamide; sodium salt;
N-(2-chloro4-sulfamoyl-phenyl)-2-[3-(3-cyano-5-difluoromethyl-phenoxy)4-ethyl-2-fluoro-phenyl]-acetamide;
2-[3-(3-cyano-5-difluoromethyl-phenoxy)4-ethyl-2-fluoro-phenyl]-N-(2-methyl4-sulfamoyl-phenyl)-acetamide;
2-[4-bromo-3-(3-chloro-5-cyano-phenoxy)-2-fluoro-phenyl]-N-(2-methyl4-sulfamoyl-phenyl)-acetamide;
2-[4-bromo-3-(3-cyano-5-difluoromethyl-phenoxy)-2-fluoro-phenyl]-N-(2-methyl-4-sulfamoyl-phenyl)-acetamide;
2-[4-bromo-3-(3-cyano-5-difluoromethyl-phenoxy)-2-fluoro-phenyl]-N-(2-chloro-4-sulfamoyl-phenyl)-acetamide;
2-[4-chloro-3-(3-cyano-5-difluoromethyl-phenoxy)-2-fluoro-phenyl]-N-(2-methyl-4-sulfamoyl-phenyl)-acetamide;
2-[3-(3-chloro-5-cyano-phenoxy)-2-fluoro4-methoxy-phenyl]-N-(2-chloro-4-sulfamoyl-phenyl)-acetamide;
2-[3-(3-chloro-5-cyano-phenoxy)-2-fluoro-4-methoxy-phenyl]-N-(2-methyl-4-sulfamoyl-phenyl)-acetamide; and,
2-[3-(3-chloro-5-cyano-phenoxy)-2-fluoro4-methyl-phenyl]-N-(2-chloro-4-propionylsulfamoyl-phenyl)-acetamide; sodium salt.

9. A method for treating HIV infection according to claim 1 further comprising co-administering at least one compound selected from the group consisting of HIV protease inhibitors, nucleoside reverse transcriptase inhibitors, non-nucleoside reverse transcriptase inhibitors, CCR5 antagonists and viral fusion inhibitors.

10. A method according to claim 9 wherein the reverse transcriptase inhibitor is selected from the group consisting of zidovudine, lamivudine, didanosine, zalcitabine, stavudine, rescriptor, sustiva and viramune, efavirenz, nevirapine or delavirdine and/or the protease inhibitor is selected from the group consisting of saquinavir, ritonavir, nelfinavir, indinavir, amprenavir, lopinavir.

11. A method for inhibiting HIV reverse transcriptase comprising administering to a host a compound according to claim 1.

12. A method according to claim 11 wherein the host is infected with a strain of HIV expressing a reverse transcriptase with at least one mutation compared to wild type HIV.

13. A method according to claim 12 wherein said strain of HIV exhibits reduced susceptibility to efavirenz, nevirapine or delavirdine.

* * * * *